US011512133B2

(12) United States Patent
Herting et al.

(10) Patent No.: US 11,512,133 B2
(45) Date of Patent: Nov. 29, 2022

(54) METHODS FOR TREATING COLON CANCER OR INHIBITING CELL PROLIFERATION BY ADMINISTERING A COMBINATION OF ANTIBODIES AGAINST HUMAN CSF-1R AND ANTIBODIES AGAINST HUMAN PD-L1

(71) Applicant: HOFFMANN-LA ROCHE INC., Little Falls, NJ (US)

(72) Inventors: Frank Herting, Penzberg (DE); Sabine Hoves, Habach (DE); Carola Ries, Penzberg (DE); Katharina Wartha, Germering (DE)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 0 days.

(21) Appl. No.: 16/784,203

(22) Filed: Feb. 6, 2020

(65) Prior Publication Data

US 2020/0392234 A1 Dec. 17, 2020

Related U.S. Application Data

(63) Continuation of application No. 15/957,387, filed on Apr. 19, 2018, now abandoned, which is a continuation of application No. 15/223,897, filed on Jul. 29, 2016, now abandoned, which is a continuation of application No. 14/485,140, filed on Sep. 12, 2014, now abandoned.

(30) Foreign Application Priority Data

Sep. 12, 2013 (EP) .................................... 13184120

(51) Int. Cl.
*C07K 16/28* (2006.01)
*A61P 35/00* (2006.01)
*C07K 16/30* (2006.01)
*A61K 39/00* (2006.01)
*A61P 35/04* (2006.01)
*A61K 39/395* (2006.01)

(52) U.S. Cl.
CPC .......... *C07K 16/2866* (2013.01); *A61P 35/00* (2018.01); *A61P 35/04* (2018.01); *C07K 16/2809* (2013.01); *C07K 16/2827* (2013.01); *C07K 16/30* (2013.01); *A61K 39/395* (2013.01); *A61K 2039/505* (2013.01); *A61K 2039/507* (2013.01); *C07K 2317/52* (2013.01); *C07K 2317/565* (2013.01); *C07K 2317/76* (2013.01)

(58) Field of Classification Search
CPC ........................ C07K 16/2827; C07K 16/2866; C07K 16/30; C07K 2317/52; C07K 2317/565; C07K 2317/76; A61P 35/00; A61K 2039/505; A61K 2039/507
See application file for complete search history.

(56) References Cited

U.S. PATENT DOCUMENTS

| | | |
|---|---|---|
| 5,202,238 A | 4/1993 | Fell, Jr. et al. |
| 5,204,244 A | 4/1993 | Fell et al. |
| 5,208,020 A | 5/1993 | Chari et al. |
| 5,416,064 A | 5/1995 | Chari et al. |
| 5,635,483 A | 6/1997 | Pettit et al. |
| 5,712,374 A | 1/1998 | Kuntsmann et al. |
| 5,714,586 A | 2/1998 | Kuntsmann et al. |
| 5,739,116 A | 4/1998 | Hamann et al. |
| 5,767,285 A | 6/1998 | Hamann et al. |
| 5,770,701 A | 6/1998 | McGahren et al. |
| 5,770,710 A | 6/1998 | McGahren et al. |
| 5,773,001 A | 6/1998 | Hamann et al. |
| 5,780,588 A | 7/1998 | Pettit et al. |
| 5,798,299 A | 8/1998 | Strittmater et al. |
| 5,866,114 A | 2/1999 | Pandit et al. |
| 5,877,296 A | 3/1999 | Hamann et al. |
| 5,961,974 A | 10/1999 | Armitage et al. |
| 5,981,724 A | 11/1999 | Armitage et al. |
| 6,184,354 B1 | 2/2001 | Koths et al. |
| 6,391,637 B1 | 5/2002 | Armitage et al. |
| 6,410,711 B1 | 6/2002 | Armitage et al. |
| 6,630,579 B2 | 10/2003 | Chari et al. |
| 6,946,129 B1 | 9/2005 | Siegall et al. |
| 7,108,852 B2 | 9/2006 | Devalaraja et al. |
| 7,223,741 B2 | 5/2007 | Krieg |
| 7,288,251 B2 | 10/2007 | Bedian |
| 7,338,660 B2 | 3/2008 | Bedian |
| 7,498,298 B2 | 3/2009 | Doronina et al. |
| 8,182,813 B2 | 5/2012 | Brasel et al. |
| 8,217,149 B2 | 7/2012 | Irving et al. |
| 8,263,079 B2 | 9/2012 | Doody |
| 8,303,955 B2 | 11/2012 | Presta et al. |
| 8,470,977 B2 | 6/2013 | Haegel et al. |

(Continued)

FOREIGN PATENT DOCUMENTS

| | | |
|---|---|---|
| CN | 101636412 A | 1/2010 |
| CN | 102791738 A | 11/2012 |

(Continued)

OTHER PUBLICATIONS

Abu-Duhier et al. "Mutational Analysis Of Class III Receptor Tyrosine Kinases (C-KIT, C-FMS, FLT3) In Idiopathic Myelofibrosis," Br. J. Haematol. 120(3):464-470, (2003).

(Continued)

*Primary Examiner* — Robert S Landsman

(74) *Attorney, Agent, or Firm* — Morrison & Foerster LLP

(57) ABSTRACT

The present invention relates to the combination therapy of specific antibodies which bind human CSF-1R with specific antibodies which bind human PD-L1.

14 Claims, 9 Drawing Sheets

Specification includes a Sequence Listing.

(56) References Cited

U.S. PATENT DOCUMENTS

| | | |
|---|---|---|
| 8,604,170 B2 | 12/2013 | Haegel et al. |
| 8,993,614 B2 | 3/2015 | Bartkovitz et al. |
| 8,999,327 B2 | 4/2015 | Dimoudis et al. |
| 9,169,323 B2 | 10/2015 | Fertig et al. |
| 9,192,667 B2 | 11/2015 | Hoves et al. |
| 9,221,910 B2 | 12/2015 | Fertig et al. |
| 9,499,624 B2 | 11/2016 | Dimoudis et al. |
| 9,499,625 B2 | 11/2016 | Dimoudis et al. |
| 9,499,626 B2 | 11/2016 | Dimoudis et al. |
| 9,617,342 B2 | 4/2017 | Fertig et al. |
| 9,624,302 B2 | 4/2017 | Fertig et al. |
| 9,663,580 B2 | 5/2017 | Dimoudis et al. |
| 9,879,085 B2 | 1/2018 | Dimoudis et al. |
| 9,988,458 B2 | 6/2018 | Fertig et al. |
| 10,023,643 B2 | 7/2018 | Fertig et al. |
| 10,030,073 B2 | 7/2018 | Fertig et al. |
| 10,072,087 B2 | 9/2018 | Dimoudis et al. |
| 10,077,314 B1 | 9/2018 | Dimoudis et al. |
| 10,287,358 B2 | 5/2019 | Dimoudis et al. |
| 10,336,830 B2 | 7/2019 | Fertig et al. |
| 2002/0141994 A1 | 10/2002 | Devalaraja et al. |
| 2003/0211100 A1 | 11/2003 | Bedian |
| 2004/0006006 A9 | 1/2004 | Armitage et al. |
| 2007/0122378 A1 | 5/2007 | Freeman |
| 2007/0280935 A1 | 12/2007 | Bohrmann et al. |
| 2009/0155164 A1 | 6/2009 | Brasel et al. |
| 2009/0304687 A1 | 12/2009 | Drachman |
| 2009/0317403 A1 | 12/2009 | Aharinejad et al. |
| 2010/0040614 A1 | 2/2010 | Ahmed |
| 2010/0203056 A1 | 8/2010 | Irving et al. |
| 2011/0081353 A1 | 4/2011 | Haegel et al. |
| 2011/0165156 A1 | 7/2011 | Dimoudis et al. |
| 2011/0178278 A1 | 7/2011 | Haegel et al. |
| 2011/0274683 A1 | 11/2011 | Wong et al. |
| 2012/0251531 A1 | 10/2012 | Baehner |
| 2012/0329997 A1 | 12/2012 | Fertig et al. |
| 2013/0005949 A1 | 1/2013 | Fertig et al. |
| 2013/0045200 A1 | 2/2013 | Irving et al. |
| 2013/0045201 A1 | 2/2013 | Irving et al. |
| 2013/0045202 A1 | 2/2013 | Irving et al. |
| 2013/0289250 A1 | 10/2013 | Haegel et al. |
| 2013/0302322 A1 | 11/2013 | Wong et al. |
| 2014/0057972 A1 | 2/2014 | Haegel et al. |
| 2014/0065135 A1 | 3/2014 | Irving et al. |
| 2014/0079699 A1 | 3/2014 | Wong et al. |
| 2014/0079706 A1 | 3/2014 | Cannarile et al. |
| 2014/0120088 A1 | 5/2014 | Carpentier et al. |
| 2014/0205608 A1 | 7/2014 | Steidl et al. |
| 2014/0255417 A1 | 9/2014 | Haegel et al. |
| 2014/0314771 A1 | 10/2014 | Hoves et al. |
| 2014/0336363 A1 | 11/2014 | Fertig et al. |
| 2014/0341902 A1 | 11/2014 | Maecker et al. |
| 2015/0073129 A1 | 3/2015 | Herting et al. |
| 2015/0080556 A1 | 3/2015 | Fertig et al. |
| 2015/0158950 A1 | 6/2015 | Dimoudis et al. |
| 2015/0175696 A1 | 6/2015 | Fertig et al. |
| 2015/0274830 A1 | 10/2015 | Dimoudis et al. |
| 2015/0274831 A1 | 10/2015 | Dimoudis et al. |
| 2015/0322153 A1 | 11/2015 | Irving et al. |
| 2016/0053015 A1 | 2/2016 | Fertig et al. |
| 2016/0220669 A1 | 8/2016 | Hoves et al. |
| 2017/0015752 A1 | 1/2017 | Fertig et al. |
| 2017/0029517 A1 | 2/2017 | Dimoudis et al. |
| 2017/0114139 A1 | 4/2017 | Fertig et al. |
| 2017/0247459 A1 | 8/2017 | Cannarile et al. |
| 2017/0275368 A1 | 9/2017 | Fertig et al. |
| 2017/0320953 A1 | 11/2017 | Dimoudis et al. |
| 2018/0186883 A1 | 7/2018 | Papadopoulos et al. |
| 2018/0208662 A1 | 7/2018 | Dimoudis et al. |
| 2018/0244788 A1 | 8/2018 | Dimoudis et al. |
| 2018/0346581 A1 | 12/2018 | Herting et al. |
| 2018/0346582 A1 | 12/2018 | Fertig et al. |
| 2019/0071507 A1 | 3/2019 | Dimoudis et al. |
| 2019/0185572 A1 | 6/2019 | Cannarile et al. |
| 2019/0218296 A1 | 7/2019 | Björck et al. |
| 2019/0284284 A1 | 9/2019 | Hoves et al. |
| 2019/0300614 A1 | 10/2019 | Dimoudis et al. |
| 2019/0309078 A1 | 10/2019 | Cannarile et al. |
| 2021/0205453 A1 | 7/2021 | Ravauri et al. |

FOREIGN PATENT DOCUMENTS

| | | |
|---|---|---|
| CN | 110636861 A | 12/2019 |
| EP | 0307434 B2 | 3/1989 |
| EP | 0668914 B1 | 8/1995 |
| EP | 0307434 B2 | 7/1996 |
| EP | 0425235 B1 | 9/1996 |
| EP | 1476185 A2 | 11/2004 |
| EP | 2423228 A1 | 2/2012 |
| EP | 2423288 A2 | 2/2012 |
| EP | 2510010 A1 | 10/2012 |
| JP | H0967400 A | 3/1997 |
| JP | 2001-523956 A | 11/2001 |
| JP | 2006-519163 A | 8/2006 |
| JP | 2008-013566 A | 1/2008 |
| JP | 2010-512421 A | 4/2010 |
| JP | 2010-536378 A | 12/2010 |
| JP | 2011-512851 A | 4/2011 |
| JP | 2013-513367 A | 4/2013 |
| JP | 2015516369 A | 6/2015 |
| JP | 2016516798 A | 6/2016 |
| JP | 2016-531150 A | 10/2016 |
| KR | 20080079301 A | 8/2008 |
| RU | 94028282 A | 7/1996 |
| RU | 2008132150 A | 2/2010 |
| RU | 2434641 C2 | 11/2011 |
| RU | 2010141584 A | 4/2012 |
| RU | 2478400 C2 | 4/2013 |
| WO | 198807089 A1 | 9/1988 |
| WO | WO-93/025687 A1 | 12/1993 |
| WO | WO-94/11026 A2 | 5/1994 |
| WO | 199818810 A1 | 5/1998 |
| WO | WO-1998/43089 A1 | 10/1998 |
| WO | WO-98/52976 A1 | 11/1998 |
| WO | WO-99/017798 A1 | 4/1999 |
| WO | 200107055 A1 | 2/2001 |
| WO | WO-01/30381 A2 | 5/2001 |
| WO | 2003040170 A2 | 5/2003 |
| WO | 2003040170 A3 | 10/2003 |
| WO | WO-2004/045532 A2 | 6/2004 |
| WO | WO-2005/046657 A2 | 5/2005 |
| WO | WO-2006/012451 A2 | 2/2006 |
| WO | WO-2006/096489 A2 | 9/2006 |
| WO | WO-2006/133396 A2 | 12/2006 |
| WO | WO-2006/133396 A3 | 12/2006 |
| WO | WO-2007/075326 A2 | 7/2007 |
| WO | WO-2007/081879 A2 | 7/2007 |
| WO | WO-2008/073959 A2 | 6/2008 |
| WO | WO-2008/083174 A2 | 7/2008 |
| WO | WO-2008/083174 A3 | 7/2008 |
| WO | WO-2008/119493 A1 | 10/2008 |
| WO | WO-2008/153926 A2 | 12/2008 |
| WO | WO-2008/153926 A3 | 12/2008 |
| WO | WO-2008/153926 A4 | 12/2008 |
| WO | WO-2009/026303 A1 | 2/2009 |
| WO | WO-2009/112245 A1 | 9/2009 |
| WO | WO-2009/120903 A2 | 10/2009 |
| WO | WO-2010/077634 A1 | 7/2010 |
| WO | 2010088395 A2 | 8/2010 |
| WO | 2010088395 A3 | 11/2010 |
| WO | WO-2011/066389 A1 | 6/2011 |
| WO | WO-2011/070024 A1 | 6/2011 |
| WO | WO-2011/107553 A1 | 9/2011 |
| WO | WO-2011/117329 A1 | 9/2011 |
| WO | WO-2011/123381 A1 | 10/2011 |
| WO | WO-2011/131407 A1 | 10/2011 |
| WO | WO-2011/140249 A2 | 11/2011 |
| WO | 2012068470 A2 | 5/2012 |
| WO | 2012085291 A1 | 6/2012 |
| WO | WO-2012/110360 A1 | 8/2012 |
| WO | WO-2013/011021 A1 | 1/2013 |
| WO | WO-2013/019906 A1 | 2/2013 |
| WO | WO-2013/057281 A2 | 4/2013 |
| WO | WO-2013/079174 A1 | 6/2013 |

(56) References Cited

FOREIGN PATENT DOCUMENTS

| | | |
|---|---|---|
| WO | WO-2013/087699 A1 | 6/2013 |
| WO | WO-2013/119716 A1 | 8/2013 |
| WO | 2012068470 A3 | 9/2013 |
| WO | WO-2013/132044 A1 | 9/2013 |
| WO | WO-2013/135648 A1 | 9/2013 |
| WO | WO-2013/169264 A1 | 11/2013 |
| WO | WO-2014/072441 A1 | 5/2014 |
| WO | WO-2014/173814 A1 | 10/2014 |
| WO | 2015036511 A1 | 3/2015 |
| WO | WO-2015/036511 A1 | 3/2015 |
| WO | 2016001160 A1 | 1/2016 |
| WO | 2016023960 A1 | 2/2016 |
| WO | 2016069727 A1 | 5/2016 |
| WO | 2016081384 A1 | 5/2016 |
| WO | 2016109310 A1 | 7/2016 |
| WO | 2016196935 A1 | 12/2016 |
| WO | 2018036852 A1 | 3/2018 |
| WO | 2018115051 A1 | 6/2018 |
| WO | 2018160917 A1 | 9/2018 |

OTHER PUBLICATIONS

Affymetrix Ebioscience. (2000-2014). "Anti-Mouse CD115 (c-fms) Purified," located at <http://www.ebioscience.com/mouse-cd115-antibody-purified-afs98.htm>, last visited on Mar. 26, 2015, 1 page.
Aharinejad et al. "Colony-Stimulating Factor-1 Blockade By Antisense Oligonucleotides And Small Interfering RNAs Suppresses Growth Of Human Mammary Tumor Xenografts In Mice," Cancer Res. 64(15):5378-5384, (2004).
Anonymous "MCSF Receptor Antibody (ab 10676)," 2 pages, (1988).
Anonymous (1988). "MCSF Receptor antibody (ab 10676)" 38 pages.
Ashmun et al. "Monoclonal Antibodies To The Human CSF-1 Receptor (c-fms Proto-Oncogene Product) Detect Epitopes On Normal Mononuclear Phagocytes And On Human Myeloid Leukemic Blast Cells," Blood 73(3):827-837, (1989).
Baker et al. "Expression Of The Colony-Stimulating Factor 1 Receptor In B Lymphocytes," Oncogene 8(2):371-378, (1993).
Balkwill et al. "Smoldering and Polarized Inflammation In The Initiation and Promotion Of Malignant Disease," Cancer Cell 7(3):211-217, (2005).
Balkwill. "TNF-Alpha In Promotion And Progression Of Cancer," Cancer Metastasis Rev. 25(3):409-416, (2006).
Barnes et al. "Advances In Animal Cell Recombinant Protein Production: GS-NSO Expression System," Cytotechnology 32(2): 109-123, (2000).
Barnes et al. "Characterization Of The Stability Of Recombinant Protein Production In The GS-NSO Expression System," Biotechnol Bioeng. 73(4):261-270, (2001).
Beiboer et al. "Guided Selection Of A Pan Carcinoma Specific Antibody Reveals Similar Binding Characteristics Yet Structural Divergence Between The Original Murine Antibody and Its Human Equivalent," J. Mol. Biol. 296(3):833-849, (2000).
Bingle et al. The Role Of Tumour-Associated Macrophages In Tumour Progression: Implications For New Anticancer Therapies, J. Pathol. 196(3):254-265, (2002).
Boackle et al. "An IgG Primary Sequence Exposure Theory For Complement Activation Using Synthetic Peptides," Nature 282(5740):742-743, (1979).
Boerner et al. "Production Of Antigen-Specific Human Monoclonal Antibodies From In Vitro-Primed Human Splenocytes," J. Immunol. 147(1):86-95, (1991).
Bonham et al. "Antagonistic Antibodies To c-fms block c-fms-Mediated Activities Reduce Tumor-Associated Macrophages and Decrease Tumor Growth In Preclinical Models," Proc. Am. Assoc. Cancer. Res. 50:503. Abstract #2077, (2009).
Bourette et al. "Early Events In M-CSF Receptor Signaling," Growth Factors 17(3): 155-166, (2000).

Brahmer et al. "Safety and ActivityOf Anti-PD-L1 Antibody In Patients With Advanced Cancer," N. Engl. J. Med. 336(26):2455-2465, (2012), 16 pages.
Bristol-Myers Squibb Cinical Trial, retrieved from <https://clinicaltrials.gov/ct2/show/NCT00729664> lasted visited on Oct. 20, 2017, 7 pages.
Bruggemann et al. "Designer Mice: The Production Of Human Antibody Repertoires In Transgenic Animals," Year Immunol. 7:33-40, (1993).
Brunhouse et al. "Isotypes of IgG: Comparison Of The Primary Structures Of Three Pairs Of Isotypes Which Differ In Their Ability To Activate Complement," Mol. Immunol. 16(11):907-917, (1979).
Burmester et al. "Mavrilimumab, A Human Monoclonal Antibody Targeting GM-CSF receptor[alpha], in Subjects With Rheumatoid Arthritis: A Randomised, Double-Blind, Placebo-Controlled, Phase 1, First-In-Human Study," Ann. Rheum. Dis. 70(9):1542-1549, (2011).
Burton et al. "The C1q Receptor Site On Immunoglobulin G," Nature 288:338-344, (1980).
Caldas et al. "Humanization Of The Anti-CD18 Antibody 6.7: An Unexpected Effect Of a Framework Residue In Binding To Antigen," Mol. Immunol. 39:941-952, (2003).
Campbell et al. "The Colony-Stimulating Factors And Collagen-Induced Arthritis: Exacerbation Of Disease By M-CSF and G-CSF and Requirement For Endogenous M-CSF," J. Leukoc. Biol. 68(1):144-150, (2000).
Carter et al. "Humanization Of An Anti-p185HER2 Antibody For Human Cancer Therapy," Proc. Natl. Acad. Sci. USA 89(10):4285-4289, (1992).
Casset et al. "A Peptide Mimetic Of An Anti-CD4 Monoclonal Antibody By Rational Design," Biochem. Biophys. Res. Commun. 307:198-205, (2003).
Cenci et al. "M-CSF Neutralization and Egr-1 deficiency Prevent Ovariectomy-Induced Bone Loss," J. Clin. Invest. 105(9):1279-1287, (2000).
Chari et al. "Immunoconjugates Containing Novel Maytansinoids: Promising Anticancer Drugs," Cancer Res. 52(1):127-131, (1992).
Chase et al. "Imatinib Sensitivity As A Consequence Of A CSF1 R-Y571 D Mutation and CSF1/CSF1 R Signaling Abnormalities In The Cell Line GDM1," Leukemia 23(2):358-364, (2009).
Choueiri et al. "The Central Role Of Osteoblasts In The Metastasis Of Prostate Cancer," Cancer Metastasis Rev. 25(4):601-609, (2006).
Cole et al. "The EBV-Hybridoma Technique And Its Application To Human Lung Cancer," Monoclonal Antibodies and Cancer Therapy Alan R. Liss, Inc. 77-96, (1985).
Coussens et al. "Structural alteration Of Viral Homologue Of Receptor Proto-Oncogene fms At Carboxyl Terminus," Nature 320(6059):277-280, (1986).
Da Costa et al. "Presence Of Osteoclast-Like Multinucleated Giant Cells In The Bone And Nonostotic Lesions Of Langerhans Cell Histiocytosis," J. Exp. Med. 201(5):687-693, (2005).
Dai et al. "Targeted Disruption Of The Mouse Colony-Stimulating Factor 1 Receptor Gene Results In Osteopetrosis, Mononuclear Phagocyte Deficiency, Increased Primitive Progenitor Cell Frequencies, And Reproductive Defects," Blood 99(1):111-120, (2002).
Daroszewska et al. "Mechanisms Of Disease: Genetics Of Paget's Disease Of Bone and Related Disorders," Nat. Clin. Pract. Rheumatol. 2(5):270-277, (2006).
Davies et al. "Affinity improvement Of Single Antibody VH Domains: Residues In All Three Hypervariable Regions Affect Antigen Binding," Immunotechnology 2(3):169-179 (1996).
De Palma et al. "Macrophage Regulation of Tumor Responses to Anticancer Therapies," Cancer Cell 23(3):277-286, (Mar. 18, 2013).
Denardo et al. "Leukocyte Complexity Predicts Breast Cancer Survival An Dfunctionally Regulates Response To Chemotherapy," Cancer Research 1(1) pp. 1-15, (Apr. 2011).
Dewar et al. "Macrophage Colony-Stimulating Factor Receptor c-fms Is A Novel Target Of Imatinib," Blood 105(8):3127-3132, (2005).
Drees et al. "Mechanisms Of Disease: Molecular Insights Into Aseptic Loosening Of Orthopedic Implants," Nat. Clin. Pract. Rheumatol. 3(3):165-171, (2007).

(56) References Cited

OTHER PUBLICATIONS

Dubowchik et al. "Doxorubicin immunoconjugates Containing Bivalent, Lysosomally-Cleavable Dipeptide Linkages," Bioorg, Med, Chem, Lett. 12(11): 1529-1532, (2002).
Durocher et al. "High-Level And High-Throughput Recombinant Protein Production By Transient Transfection Of Suspension-Growing Human 293-EBNA1 Cells," Nucleic Acids Res. 30(2):E9, (2002).
English Translation of Notification of Reasons for Rejection for Japanese Patent Application No. 2012-542522, dated Feb. 25, 2014 (3 pages}.
European Search Report for Application No. EP 09007224.0 pp. 1-9 (dated Nov. 24, 2009).
European Search Report for Application No. EP 09015310 pp. 1-8 (dated Sep. 9, 2010).
Extended European Search Report for European Patent Application No. EP 12158519.4, dated Aug. 2, 2012 (8 pages).
Feldstein et al. "Practice Patterns In Patients At Risk For Glucocorticoid-Induced Osteoporosis," Osteoporos Int. 16(12):2168-2174, (2005).
Flatman et al. "Process Analytics For Purification Of Monoclonal Antibodies," J. Chromatogr. B Analyt. Technol. Biomed. Life Sci. 848{1):79-87, (2007).
Flick et al. "Recognition Of Activated CSF-1 receptor In Breast Carcinomas By A Tyrosine 723 Phosphospecific Antibody," Oncogene 14:2553-2561, (1997).
Geisse et al. "Eukaryotic Expression Systems: A Comparison," Protein Expr. Purif. 8(3):271-282, (1996).
Genentech. "Our Pipeline," retrieved from <https://www.gene.com/medical-professionals/pipeline, last visited Oct. 20, 2017, 7 pages.
Gordon et al. "Abstract LB-288: A Phase I Study of MPDL3280A, An Engineered PD-L1 Antibody In Patients With Locally Advanced Or Metastatic Tumors," Proceedings. AACR 104th Annual Meeting 2013, (Apr. 2013), 2 pages.
Guzman-Clark et al. "Barriers In The Management Of Glucocorticoid-Induced Osteoporosis," Arthritis Rheum. 57(1):140-146, (2007).
Hamilton. "Colony-Stimulating Factors In Inflammation And Autoimmunity," Nat. Rev. Immunol. 8 (7):533-544, (2008).
Hao et al. "Expression Of Macrophage Colony-Stimulating Factor and Its Receptor In Microglia Activation Is Linked To Teratogen-Induced Neuronal Damage," Neuroscience 112(4):889-900, (2002).
Haran-Gehera et al. "Increased Circulating Colony-Stimulating Factor-1 (CSF-1) in SJL/J Mice With Radiation-Induced Acute Myeloid Leukemia (AML) Is Associated With Autocrine Regulation Of AML Cells By CSF-1," The American Society of Hematology 89(7):2537-2545, (1997).
Hayashi et al. "Osteoclast Precursors In Bone Marrow and Peritoneal Cavity," J. Cell Physiol. 170(3):241-247, (1997).
Hezareh et al. "Effector Function Activities Of A Panel Of Mutants Of A Broadly Neutralizing Antibody Against Human Immunodeficiency Virus Type 1," J. Virol. 75(24):12161-12168, (2001).
Hinman et al. "Preparation and Characterization Of Monoclonal Antibody Conjugates Of The Calicheamicins: A Novel and Potent Family Of Antitumor Antibiotics," Cancer Res. 53(14):3336-3342, (1993).
Holt et al. "Domain Antibodies: Proteins For Therapy," Trends in Biotechnology 21(11):484-490, (2003).
Hoogenboom et al. "By-Passing Immunisation. Human Antibodies From Synthetic Repertoires Of Germline VH Gene Segments Rearranged In Vitro," J. Mol. Biol. 227(2):381-388, (1992).
Hume et al. "Therapeutic Applications Of Macrophage Colony-Stimulating Factor-1 (CSF-1) and Antagonists Of CSF-1 Receptor (CSF-1R) Signaling," Blood 119(8):1810-1820, (2012, e-pub. Dec. 20, 2011).
Huston et al. "Protein Engineering Of Single-Chain Fv Analogs and Fusion Proteins," Methods Enzymol. 203:46-88, (1991).
Ide et al. "Expression Of Colony-Stimulating Factor 1 Receptor During Prostrate Development and Prostate Cancer Progression," Proc. Natl. Acad. Sci. U.S.A. 99(22):14404-14409, (2002, e-pub. Oct. 15, 2002).

Idusogie et al. "Mapping Of The C1q Binding Site On Rituxan, A Chimeric Antibody With A Human lgG1 Fc," J. Immunol. 164(8):4178-4184, (2000).
Ikonomidis et al. "Increased Circulating C-Reactive Protein And Macrophage-Colony Stimulating Factor Are Complementary Predictors Of Long-Term Outcome In Patients With Chronic Coronary Artery Disease," Eur. Heart. J. 26(16):1618-1624, (2005).
Inaba et al. "Expression Of M-CSF Receptor Encoded By c-fms on Smooth Muscle Cells Derived From Arteriosclerotic Lesion," J. Biol. Chem. 267(8):5693-5699, (1992).
International Search Report for International Patent Application No. PCT/EP2011/053214, dated Apr. 28, 2011 (6 pages).
International Search Report for International Patent Application No. PCT/EP2013/054676, dated May 7, 2013 (7 pages).
International Search Report for International Patent Application No. PCT/EP2012/075241, dated Feb. 22, 2013 (7 pages).
International Search Report for PCT Application No. PCT/EP2011/053213, dated Sep. 1, 2011, filed on Mar. 3, 2011, 6 pages.
International Search Report for PCT Application No. PCT/EP2014/057909, dated Sep. 1, 2014, filed on Apr. 17, 2014, 6 pages.
International Search Report dated Nov. 18, 2014, for PCT Patent Application No. PCT/EP2014/069451, filed on Sep. 11, 2014, 7 pages.
Iwai et al. "Involvement of PD-L1 on tumor cells in the escape from host immune system and tumor immunotherapy by PD-L1 blockade," Proc. Natl. Acad. Sci. USA 99(19):12293-12297 (2002).
Jakobovits et al. "Analysis Of Homozygous Mutant Chimeric Mice: Deletion Of The Immunoglobulin Heavy-Chain Joining Region Blocks B-Cell Development and Antibody Production," Proc. Natl. Acad. Sci. USA 90(6):2551-2555, (1993).
Jakobovits et al. "Germ-line Transmission And Expression Of A Human-Derived Yeast Artificial Chromosome," Nature 362(6417):255-258, (1993).
Jeffrey et al. "Dipeptide-Based Highly Potent Doxorubicin Antibody Conjugates," Bioorg. Med. Chem. Lett. 16(2):358-362,(2006).
Johnson et al. "Kabat Database and Its Applications: 30 Years After The First Variability Plot," Nucleic Acids Res. 28(1):214-218, (2000).
Jose et al. "Blockade Of Macrophage Colony-Stimulating Factor Reduces Macrophage Proliferation and Accumulation In Renal Allograft Rejection," American Journal of Transplantation 3:294-300, (2003).
Kabat et al. "Tabulation and Analysis Of Amino Acid And Nucleic Acid Sequences Of Precursors, V-Regions, C-Regions, J-Chain, Beta2-Microglobulins, Major Histocompatibility Antigens, Thy-1, Complement, C-Reactive Protein, Thymopoietin, Post-Gamma Globulin, and Alpha2macroglobulin," Sequences of Proteins of Immunological Interest. U.S. Department of Health and Human Services, 10L, (1983).
Kacinski et al. "Ovarian Adenocarcinomas Express fms-Complementary Transcripts and fms Antigen, Often With Coexpression Of CSF-1," American Journal of Pathology 137(1):135-147, (1990).
Kacinski. "CSF-1 and Its Receptor In Breast Carcinomas and Neoplasms Of The Female Reproductive Tract," Mol. Reprod. Dev. 46(1):71-74, (1997).
Kaku et al. "Amyloid β Protein Deposition and Neuron Loss In Osteopetrotic (Op/Op) Mice," Brain Res. Protoc. 12(2):1 04-108, (2003).
Kaufman. "Overview Of Vector Design For Mammalian Gene Expression," Mol. Biotechnol. 16(2):151-160, (2000).
Kawakami et al. "Macophage-colony Stimulating Factor Inhibits The Growth Of Human Ovarian Cancer Cells In Vitro," European Journal of Cancer 36:1991-1997, (2000).
King et al. "Monoclonal Antibody Conjugates Of Doxorubicin Prepared With Branched Peptide Linkers: Inhibition Of Aggregation By Methoxytriethyleneglycol Chains," J. Med. Chem. 45(19):4336-4343, (2002).
Kirma et al. "Elevated Expression Of The Oncogene c-fms and its Ligand, The Macrophage Colony-Stimulating Factor-1, In Cervical Cancer And The Role Of Transforming Growth Factor-Beta1 In Inducing c-fms Expression," Cancer Res. 67(5):1918-1926 ,(2007).

(56) References Cited

OTHER PUBLICATIONS

Kitaura et al. "An Anti-c-fms Antibody Inhibits Orthodontic Tooth Movement," Journal of Dental Research 87(4):396-400, (2008).
Kitaura et al. "M-CSF Mediates TNF-Induced Inflammatory Osteolysis," J. Clin. Invest. 115(12):3418-3427, (2005).
Kommoss et al. "Co-Expression of M-CSF Transcripts And Protein, FMS (M-CSF Receptor) Transcripts and Protein, and Steroid Receptor Content In Adenocarcinomas Of The Ovary," Journal of Pathology 174:111-119, (1994).
Kratz et al. "Prodrugs Of Anthracyclines In Cancer Chemotherapy," Curr. Med .Chem. 13(5):477-523, (2006).
Krieg. "Toll-like receptor 9 (TLR9) agonists in the treatment of cancer," Oncogene 27(2):161-167, (2008).
Lee et al. "Functional Dissection Of Structural Domains In The Receptor For Colony-Stimulating Factor-1," The Journal of Biological Chemistry 267(23):16472-16483, (1992).
Lee et al. "The Cbl Protooncoprotein Stimulates CSF-1 Receptor Multiubiquitination and Endocytosis, and Attenuates Macrophage Proliferation," EMBO J. 18(13):3616-3628, (1999).
Lenda et al. "Reduced Macrophage Recruitment, Proliferation, and Activation In Colony-Stimulating Factor-1-Deficient Mice Results In Decreased Tubular Apoptosis During Renal Inflammation," J. Immunol. 170(6):3254-3262,(2003).
Lester et al. "Current Management Of Treatment-Induced Bone Loss In Women With Breast Cancer Treated In The United Kingdom," Br. J. Cancer 94(1):30-35 ,(2006).
Lewis et al. "Distinct Apoptotic Signaling Characteristics Of The Anti-CD40 Monoclonal Antibody Dacetuzumab And Rituximab Produce Enhanced Antitumor Activity In Non-Hodgkin Lymphoma," Clin Cancer Res. 17(14):4672-4681, (2011).
Li et al. "Role Of Dimerization And Modification Of The CSF-1 Receptor In Its Activation and internalization During The CSF-1 Response," The EMBO Journal 10(2):277-288, (1991).
Lin et al. "Discovery Of A Cytokine And Its Receptor By Functional Screening Of The Extracellular Proteome," Science 320:807-811, (2008).
Lode et al. "Targeted Therapy With A Novel Enediyne Antibiotic Calicheamicin θIl Effectively Suppresses Growth and Dissemination Of Liver Metastases In A Syngeneic Model Of Murine Neuroblastoma," Cancer Res. 58(14):2925-2928, (1998).
Lukas et al. "Inhibition of C1-Mediated Immune Hemolysis By Monomeric And Dimeric Peprides From The Second Constant Domain Of Human Immunoglobulin G," J. Immunol. 127(6):2555-2560, (1981).
MacCallum et al. "Antibody-Antigen Interactions: Contact Analysis And Binding Site Topography," J. Mol. Biol. 262:732-745, (1996).
MacDonald et al. "An Antibody Against The Colony-Stimulating Factor 1 Receptor Depletes The Resident Subset Of Monocytes and Tissue- and Tumor-Associated Macrophages But Does Not Inhibit Inflammation," Blood 116(19):3955-3963, (2010).
Makrides. "Components Of Vectors For Gene Transfer and Expression In Mammalian Cells," Protein Expr. Purif. 17(2):183-202, (1999).
Mancino et al. "Breast Cancer Increases Osteoclastogenesis By Secreting M-CSF and Upregulating RANKL In Stromal Cells," Journal of Surgical Research 100:18-24, (2001, e-pub. Jul. 24, 2001).
Mantovani et al. "The Chemokine System In Diverse Forms Of Macrophage Activation and Polarization," Trends Immunol. 25(12):677-686, (2004).
Marks et al. "By-Passing Immunization. Human Antibodies From V-gene Libraries Displayed On Phage," J. Mol. Biol. 222(3):581-597, (1991).
Martin et al. "Growth and Angiogenesis Of Human Breast Cancer In A Nude Mouse Tumour Model Is Reduced By NK4, A HGF/SF Antagonist," Carcinogenesis 24(8):1317-1323, (2003).
Morgan et al. "The N-Terminal End Of The CH2 Domain Of Chimeric Human lgG1 Anti-HLA-DR Is Necessary For C1q, FcγR1 and FcγRill Binding," Immunology 86(2):319-324, (1995).

Morrison et al. "Chimeric Human Antibody Molecules: Mouse Antigen-Binding Domains With Human Constant Region Domains," Proc. Natl. Acad. Sci. USA 81(21):6851-6855, (1984).
Murayama et al., "Intraperitoneal Administration Of Anti-c-fms Monoclonal Antibody Prevents Initial Events Of Atherogenesis But Does Not Reduce The Size Of Advanced Lesions In Apolipoprotein E-Deficient Mice," Circulation 99(13):1740-1746, (Apr. 6, 1999).
Murphy et al. "Expression Of Macrophage Colony-Stimulating Factor Receptor Is Increased In The AβPP(V717F) Transgenic Mouse Model Of Alzheimer's Disease," Am. J. Pathol. 157(3):895-904, (2000).
Murphy et al. "Macrophage Colony-Stimulating Factor Augments Beta-Amyloid-Induced Interleukin-1, Interleukin-6, and Nitric Oxide Production By Microglial Cells," J. Biol. Chem. 273(33):20967-20971, (1998).
Nagy et al. "Stability Of Cytotoxic Luteinizing Hormone-Releasing Hormone Conjugate (AN-152) Containing Doxorubicin 14-0-Hemiglutarate In Mouse and Human Serum In Vitro: Implications For The Design Of Preclinical Studies," Proc. Natl. Acad. Sci. USA 97(2):829-834, (2000).
Neuberger et al. "A Hapten-Specific Chimaeric lgE Antibody With Human Physiological Effector Function," Nature 314(6008):268-270, (1985).
Ngan et al. "Proto-oncogenes and p53 protein expression in normal cervical stratified squamous epithelium and cervical intra-epithelial neoplasia," Eur. J. Cancer 35(10):1546-1550, (1999).
Nicola et al. "Neutralizing and Nonneutralizing Monoclonal Antibodies To The Human Granulocyte-Macrophage Colony-Stimulating Factor Receptor Alpha-Chain," Blood 82(6):1724-1731, (1993).
Norderhaug et al. "Versatile Vectors For Transient and Stable Expression Of Recombinant Antibody Molecules In Mammalian Cells," J. Immunol. Methods 204(1):77-87, (1997).
Orlandi et al. "Cloning immunoglobulin Variable Domains For Expression By The Polymerase Chain Reaction," Proc. Natl. Acad. Sci. USA 86(10):3833-3837, (1989).
Patel et al. "Colony-stimulating Factor-1 Receptor Inhibitors For The Treatment Of Cancer and Inflammatory Disease," Curr. Top. Med. Chem. 9(7):599-610, (2009).
Paul. Structure and Function Of Immunoglobulins, Fundamental Immunology, 3rd Ed., Raven Press, 292-295, (1993).
Paulus et al. "Colony-Stimulating Factor-1 Antibody Reverses Chemoresistance In Human MCF7 Breast Cancer Xenografts," Cancer Res. 66(8):4349-4356, (2006).
Pixley et al. "CSF-1 Regulation Of The Wandering Macrophage: Complexity In Action," Trends Cell Biol. 14(11):628-638, (2004).
Pollard. "Role Of Colony-Stimulating Factor-1 In Reproduction and Development," Mol. Reprod. Dev. 46(1):54-61, (1997).
Pollard. "Tumour-Educated Macrophages Promote Tumour Progression and Metastasis," Nat. Rev. Cancer 4(1):71-78, (2004).
Queen et al. "A Humanized Antibody That Binds To The Interleukin 2 Receptor," Proc. Natl. Acad. Sci. USA 86(24):10029-10033, (1989).
Rabello et al. "CSF1 gene Associated With Aggressive Periodontitis In The Japanese Population," Biochem. Biophys. Res. Commun. 347(3):791-796, (2006).
Ridge et al. "FMS Mutations In Myelodysplastic, Leukemic, and Normal Subjects," Proc. Natl. Acad Sci USA 87(4):1377-1380, (1990).
Riechmann et al. "Reshaping human antibodies for therapy," Nature 332(6162): 323-327, (1988).
Ries et al. "Targeting Tumor-Associated Macrophages With Anti-CSF-1R Antibody Reveals A Strategy For Cancer Therapy," Cancer Cell 25(6):846-859, (2014).
Ritchlin et al. "Mechanisms Of TNF-Alpha- and RANKL-Mediated Osteoclastogenesis And Bone Resorption In Psoriatic Arthritis," J. Clin. Invest. 111(6):821-831, (2003).
Roggia et al. "Role Of TNF-Alpha Producing T-Cells In Bone Loss Induced By Estrogen Deficiency," Minerva Med. 95(2):125-132, (2004).
Roth et al. "The Biology Of CSF-1 and Its Receptor," Curr. Top. Microbiol .Immunol. 181:141-167, (1992).

(56) References Cited

OTHER PUBLICATIONS

Roussel et al. "Mouse NIH 3T3 cells Expressing Human Colony-Stimulating Factor 1 (CSF-1) Receptors Overgrow In Serum-Free Medium Containing Human CSF-1 As Their Only Growth Factor," Proc. Natl. Acad. Sci. USA 86(20):7924-7927, (1989).
Roussel et al. "Transforming Potential Of The c-fms Proto-Oncogene (CSF-1 Receptor)," Nature 325(6104):549-552, (1987).
Saitoh et al. "Clinical Significance Of Increased Plasma Concentration Of Macrophage Colony-Stimulating Factor In Patients With Angina Pectoris," J. Am. Coll. Cardiol. 35(3):655-665, (2000).
Sapi et. al. "Effect of All-trans-Retinoic Acid on c-fms Proto-Oncogene [Colony-Stimulating Factor 1 (CSF-1) Receptor] Expression and CSF-1-Induced Invasion and Anchorage-Independent Growth of Human Breast Carcinoma Cells," Cancer Res. 59:5578-5585, (1999).
Sawada et al. "Activation and Proliferation Of The Isolated Microglia By Colony Stimulating Factor-1 And Possible Involvement Of Protein Kinase C," Brain Res. 509(1):119-124, (1990).
Schlaeger et al. "Transient Gene Expression In Mammalian Cells Grown In Serum-Free Suspension Culture," Cytotechnology 30(1-3):71-83, (1999).
Schlaeger. "The Protein Hydrolysate, Primatone RL, Is A Cost-Effective Multiple Growth Promoter Of Mammalian Cell Culture In Serum-Containing And Serum-Free Media And Displays Anti-Apoptosis Properties," J. Immunol. Methods 194(2):191-199, (1996).
Scholl et al. "Anti-colony-Stimulating Factor-1 Antibody Staining In Primary Breast Adenocarcinomas Correlates With Marked Inflammatory Cell Infiltrates and Prognosis," J. Natl. Cancer Inst. 86(2):120-126, (1994).
Shadduck et al. "Paradoxical Stimulation Of Normal And Leukemic Rat Hematopoiesis By Monoclonal Antibody To CSF-1 Receptor," Experimental Hematology 24:314-317, (1996).
Sherr et al. "Inhibition Of Colony-Stimulating Factor-1 Activity By Monoclonal Antibodies To The Human CSF-1 Receptor," Blood 73(7):1786-1793, (1989).
Sherr et al. "The c-fms Proto-Oncogene Product Is Related To The Receptor For The Mononuclear Phagocyte Growth Factor, CSF-1," Cell 41(3):665-676, (1985).
Shulman, et al. "An Antibody Reactive With Domain 4 Of The Platelet-Derived Growth Factor β Receptor Allows BB Binding While Inhibiting Proliferation By Impairing Receptor Dimerization," The Journal Of Biological Chemistry 272(28):17400-17404, (1997).
Stanley et al. "Biology and Action Of Colony-Stimulating Factor-1," Mol. Reprod. Dev. 46(1):4-10, (1997).
Stanley et al. "The Biology and Action Of Colony Stimulating Factor-1," Stem Cells 12(Suppl 1):15-25, (1994).
Stanley et al. "CSF-1-A Monoclonal Phagocyte Lineage-Specific Hemopoietic Growth Factor," Journal of Cellular Biochemistry 21(2):151-159, (1983).
Stoch et al. "Bone loss In Men With Prostate Cancer Treated With Gonadotropin-Releasing Hormone Agonists," J. Clin. Endocrinol. Metab. 86(6):2787-2791, (2001).
Strausberg et al. CSF1R Colony Stimulating Factor 1 Receptor [Homo sapiens] Accession No. AAH47521 (Aug. 7, 2008, updated Apr. 14, 2018), 17 pages.
Sudo et al. "Functional Hierarchy of c-kit and c-fms In Intramarrow Production Of CFU-M," Oncogene 11(12):2469-2476, (Dec. 21, 1995).
Sundberg, E.J. "Structural Basis Of Antibody-Antigen Interactions," Methods Mol Biol. 524:23-36, (2009, e-pub. Feb. 24, 2009).
Tanaka et al. "Macrophage Colony-Stimulating Factor Is Indispensable For Both Proliferation and Differentiation Of Osteoclast Progenitors," J. Clin. Invest. 91(1):257-263, (1993).
Taylor et al. "FMS Receptor For M-CSF (CSF-1) Is Sensitive To The Kinase Inhibitor Imatinib and Mutation Of Asp-802 To Val Confers Resistance," Oncogene pp. 1-5, (2005).
Thommesen et al. "Lysine 322 In The Human lgG3 C(H)2 Domain Is Crucial For Antibody Dependent Complement Activation," Mol. Immunol. 37(16):995-1004, (2000).

Torgov et al. "Generation Of An Intensely Potent Anthracycline By A Monoclonal Antibody-Beta-Qalactosidase Conjuqate," Bioconjugate Chem. 16(3):717-721, (2005).
Tortora et al., "Novel toll-like Receptor 9 (TLR9) agonists IMO inhibits tumor growth an cooperates with cetuximab in K-Ras mutant colon pancreatic cancers," Proceedings of the American Association for Cancer Research. 51:146 (2010).
Tortora, G. et al. "Novel Toll-Like Receptor 9 (TLR9) Agonists IMO Inhibits Tumor Growth An Cooperates With Cetuximab In K-Ras Mutant Colon Pancreatic Cancers," Proceedings of the American Association for Cancer Research. 51:146, (Apr. 2010).
U.S. Appl. No. 14/825,779, filed Aug. 13, 2015, for Irving et al.
U.S. Appl. No. 14/846,457, filed Sep. 4, 2015, for Irving et al.
U.S. Appl. No. 15/043,846, filed Feb. 15, 2016, for Irving et al.
U.S. Appl. No. 15/075,616, filed Mar. 21, 2016, for Irving et al.
U.S. Appl. No. 15/404,987, filed Jan. 12, 2017, for Hoves et al.
U.S. Appl. No. 15/686,834, filed Aug. 25, 2017, 2017, for Hoves et al.
U.S. Appl. No. 15/875,530, filed Jan. 19, 2018, for Dimoudis et al.
U.S. Appl. No. 15/934,686, filed Mar. 23, 2018, for Fertig et al.
U.S. Appl. No. 15/947,647, filed Apr. 6, 2018, for Hoves et al.
Van Dijk et al. "Human Antibodies As Next Generation Therapeutices," Curr. Opin. Chem. Biol. 5(4):368-374, (2001).
Vessella et al. "Targeting Factors Involved In Bone Remodeling As Treatment Strategies In Prostate Cancer Bone Metastasis," Clin. Cancer Res. 12(20 Pt 2):6285s-6290s, (2006).
Vitetta et al. "Redesigning Nature's Poisons To Create Anti-Tumor Reagents," Science 238(4830):1098-1104, (1987).
Wang et al. "Identification Of The Ligand-Binding Regions In The Macrophage Colony-Stimulating Factor Receptor Extracellular Domain," Mol, Cell, Biol. 13(9):5348-5359 (1993).
Weir et al. "Colony Stimulating Factor-1 Plays A Role In Osteoclast Formation And Function In Bone Resorption Induced By Parathyroid Hormone and Parathyroid Hormone-Related Protein," Journal of Bone and Mineral 11(10):1474-1481, (1996).
Werner et al. "Appropriate Mammalian Expression Systems For Biopharmaceuticals," Arzneimittelforschung 48(8):870-880, (1998).
West et al. "A Landscape Effect In Tenosynovial Giant-Cell Tumor From Activation Of CSF1 EK Expression By A Translocation In A Minority Of Tumor Cells," Proc. Natl. Acad. Sci. USA 103(3):690-695, (2006).
Written Opinion dated Nov. 18, 2014, for PCT Application No. PCT/EP2014/069451, filed on Sep. 11, 2014, six pages.
Written Opinion dated Sep. 1, 2011, for PCT Application No. PCT/EP2011/053213, filed on Mar. 3, 2011, seven pages.
Yang et al. "The Relationship Between Point Mutation And Abnormal Expression Of c-fms Oncogene In Hepatocellular Carcinoma," Hepatobiliary Pancreat. Dis. Int. 3(1):86-89, (2004).
Yeung et al. "Proteomic approaches to the analysis of early events in colony-stimulating factor-1 signal transduction," Mol Cell Proteomics. 2(11):1143-1155 (2003).
Yuzawa, et al. "Structural Basis For Activation Of The Receptor Tyrosine Kinase KIT By Stem Cell Factor," Cell 130(2):323-334, (Jul. 27, 2007).
Zheng et al. "Membrane-Bound Macrophage Colony-Stimulating Factor and its Receptor Play Adhesion Molecule-Like Roles In Leukemic Cells," Leuk. Res. 24(5):375-383, (2000).
Zins et al. "Colon Cancer Cell-Derived Tumor Necrosis Factor-Alpha Mediates The Tumor Growth-Promoting Response In Macrophages By Up-Regulating The Colony-Stimulating Factor-1 Pathway," Cancer Res. 67(3):1038-1045, (2007).
US 9,951,139, 10/2016, Dimoudis et al. (withdrawn)
US 9,951,140, 10/2016, Dimoudis et al. (withdrawn)
Agrawal, S. et al. (Dec. 2007) "Synthetic Agonists Of Toll-Like Receptors 7, 8 and 9," Biochemical Society Transactions 35(Pt. 6):1461-1467.
Albert, M.L. et al. (Mar. 5, 1998). "Dendritic Cells Acquire Antigen From Apoptotic Cells and Induce Class I-Restricted CTLs," Nature 392(6671):86-89.
Alderson, M.R. et al. (Aug. 1, 1993). "CD40 Expression By Human Monocytes: Regulation By Cytokines and Activation Of Monocytes By The Ligand For CD40," J. Exp. Med. 178:669-674.

(56) References Cited

OTHER PUBLICATIONS

Altenburg, A. et al. (Apr. 1, 1999). "CD40 Ligand-CD40 Interaction Induces Chemokines In Cervical Carcinoma Cells In Synergism With IFN-γ," J. Immmol. 162(7):4140-4147.
Anonymous (Dec. 18, 2016). "NCT02452424: A Combination Clinical Study of PLX3397 and Pembrolizumab To Treat Advanced Melanoma and Other Solid Tumors," pp. 1-7.
Anonymous. (Oct. 3, 2016). "NCT02323191: A Study of Emactuzumab (RO5509554) and (MPDL3280A) Administered in Combination in Patients With Advanced Solid Tumors," pp. 1-5. MPDL3280A Administered in Combination in Patients With Advanced Solid Tumors, pp. 1-5.
Armant, M. et al. (Jul. 1996). "Functional CD40 Ligand Expression On T Lymphocytes In The Absence Of T Cell Receptor Engagement: Involvement In Interleukin-2-Induced Interleukin-12 and Interferon-Gamma Production," Eur. J. Immunol. 26(7):1430-1434.
ATCC CCL 87—"Jiyoye,", retrieved from https//www.atcc.org/Products/All/CCL-87.aspx, last visited Jul. 12, 2019, 3 pages.
Ausubel, F. et al. (1987). Current Protocols in Molecular Biology, Greene Publishing and Wiley Interscience, New York, TOC, 7 pages.
Banchereau, J. et al. (1995). "Functional CD40 Antigen On B Cells, Dendritic Cells and Fibroblasts," Adv. Exp. Med. & Biol. 378:79-83.
Bauer, S. et al. (Jul. 31, 2001). "Human TLR9 Confers Responsiveness To Bacterial DNA Via Species-Specific CpG Motif Recognition," Proc. Natl. Acad. Sci. USA 98(16):9237-9242.
Bauer, S. et al. (2002). "Bacterial CpG-DNA Licenses TLR9," Current Topics in Microbiology and Immunology 270:145-154.
Beatty, G.L. et al. (Mar. 25, 2011). "CD40 Agonists Alter Tumor Stroma and Show Efficacy Against Pancreatic Carcinoma In Mice and Humans," Science 331(6024):1612-1616, 9 pages.
Bellovin, D. I. et al. (2015). "Tumor Weight (mean g SEM) Tumor Weight (mean g SEM) cmFPA008, an Anti-Mouse CSF-IR Antibody, Combines with Multiple Immunotherapies to Reduce Tumor Growth in Nonclinical Models", Poster, 1 page.
Bennett, S.R. et al. (Jul. 7, 1997). "Induction of a CD8+ Cytotoxic T Lymphocyte Response By Cross-Priming Requires Cognate CD4+ T Cell Help," J. Exp. Med. 186(1):65-70.
Bennett, S.R. et al. (Jun. 4, 1998). "Help For Cytotoxic-T-Cell Responses Is Mediated By CD40 Signalling," Nature 393(6684):478-480.
Boettler, T. et al. (Apr. 2006). "Expression of the Interleukin-7 Receptor Alpha Chain (CD127) on Virus-Specific CD8+ T Cells Identifies Functionally and Phenotypically Defined Memory T Cells during Acute Resolving Hepatitis B Virus Infection," J. Virol. 80(7):3532-3540.
Bonelli, S. et al. (Feb. 2017). "Beyond the M-CSF Receptor—Novel Therapeutic Targets in Tumor-Associated Macrophages," FEBS J. 285(4):777-787.
Brassard, D.L. et al. (Apr. 2002). "Interferon-α As An Immunotherapeutic Protein," J Leukoc. Biol. 71(4):565-581.
Bretscher, P. (1970). et al. "A Theory of Self-Nonself Discrimination," Science 169:1042-1049.
Bretscher, P.A. (Jan. 1999). "A Two-Step, Two-Signal Model for the Primary Activation of Precursor Helper T Cells," Proc. Natl. Acad. Sci. USA, 96:185-190.
Brodská, B. et al. (Oct. 2016, e-pub. Aug. 19, 2016). "Correlation of PD-L1 Surface Expression on Leukemia Cells With the Ratio of PD-L1 mRNA Variants and With Electrophoretic Mobility," Cancer Immunol. Res. 4(10):815-819.
Brossart, P. et al. (Dec. 1998). "Generation of Functional Human Dendritic Cells From Adherent Peripheral Blood Monocytes by CD40 Ligation in the Absence of Granulocyte-Macrophage Colony-Stimulating Factor," Blood 92(11):4238-4247.
Brown, M. et al. (1996) "Tolerance to Single, but Not Multiple, Amino Acid Replacements in Antibody VH CDR2," J. Immunol. 156:3285-3291.

Bryne, K.T. et al. (Jul. 1, 2016). "CSF-IR-Dependent Lethal Hepatotoxicity When Agonistic CD40 Antibody Is Given before but Not after Chemotherapy", The Journal Immunology 197(1):179-187, 20 pages.
Buhlmann J.E. et al. (Jun. 1995). "In the Absence of a CD40 Signal, B Cells Are Tolerogenic," Immunity 2:645-653.
Butte, M.J. et al. (Jul. 2007). "Programmed Death-1 Ligand 1 Interacts Specifically with the B7-1 Costimulatory Molecule to Inhibit T Cell Responses," Immunity 27:111-122, 12 pages.
Callahan, M.K. et al. (Jul. 2013). "At the Bedside: CTLA-4- and PD-1-Blocking Antibodies in Cancer Immunotherapy," J. Leukoc. Biol. 94:41-53.
Carbone, E. et al. (Jun. 16, 1997). "A New Mechanism of NK Cell Cytotoxicity Activation: The CD40-CD40 Ligand Interaction," J. Exp. Med. 185(12):2053-2060.
Carpentier, A.F. et al. (Jan. 2006). "Phase 1 Trial Of A CpG Oligodeoxynucleotide For Patients With Recurrent Glioblastoma," Neuro-Oncology 8(1):60-66.
Carter, L. et al. (Mar. 2002). "PD-1: PD-L Inhibitory Pathway Affects Both CD4(+) and CD8(+) T Cells And Is Overcome By IL-2," Eur. J. Immunol. 32(3):634-643.
CAS No. 880486-59-9, retrieved from https:pubchem.ncbi.nlm.nih.gov/substance/135323347, last visited Jul. 12, 2019. 3 pages.
Caux, C. et al. (Oct. 1, 1994). "Activation of Human Dendritic Cells Through CD40 Cross-Linking," Journal Exp. Med. 180(4):1263-1272.
Cella, M. et al. (Feb. 2009, e-pub. Nov. 2, 2008). "A Human Natural Killer Cell Subset Provides an Innate Source of IL-22 for Mucosal Immunity," Nature 457:722-725.
Chambers, S.K. (Nov. 2009). "Role of CSF-1 In Progression Of Epithelial Ovarian Cancer," Future Oncol 5(9):1429-1440, 18 pages.
Chaussabel, D. et al. (Apr. 1999). "CD40 Ligation Prevents Trypanosoma cruzi Infection through Interleukin-12 Upregulation," Infection & Immunity 67(4):1929-1934.
Chin, L.-T. et al. (Jan.-Feb. 2008). "Immune Intervention With Monoclonal Antibodies Targeting CD152 (CTLA-4) for Autoimmune and Malignant Diseases," Chang Gung Med. J. 31(1):1-15.
Clinicaltrials.gov NCT02323191 (Dec. 23, 2014). "A Study of Emactuzumab and Atezolizumab Administered in Combination in Participants With Advanced Solid Tumors," 10 pages.
Coffman, R.L. et al. (Oct. 29, 2010) "Vaccine Adjuvants: Putting Innate Immunity to Work," Immunity 33(4):492-503, 21 pages.
CP-870,893—"CD40 Agonist Monoclonal Antibody CP-870,893,", retrieved from https://www.ncbi.nlm.nih.gov/medgen/?term=CP-870,893, last visited Jul. 12, 2019, 2 pages.
Dalpke, A.H. et al. (May 2002). "Phosphodiester CpG Oligonucleotides As Adjuvants: Polyguanosine Runs Enhance Cellular Uptake And Improve Immunostimulative Activity Of Phosphodiester CpG Oligonucleotides in vitro and in vivo," Immunology 106(1):102-112.
Damiano, V. et al. (Jan. 15, 2006). "Novel Toll-Like Receptor 9 Agonist Induces Epidermal Growth Factor Receptor (EGFR) Inhibition and Synergistic Antitumor Activity With EGFR Inhibitors," Clin. Cancer Res. 12(2):577-583.
Deckers, J.G.M. et al. (1998). "IL-4 and IL-13 Augment Cytokine- and CD40-Induced RANTES Production By Human Renal Tubular Epithelial Cells in vitro," J. The Am Society of Nephrology 9:1187-1193.
Denardo, D.G. et al. (Jun. 1, 2011). "Leukocyte Complexity Predicts Breast Cancer Survival and Functionally Regulates Response to Chemotherapy," Cancer Discovery 1:54-67, 30 pages.
Denardo, D.G. et al. (Aug. 4, 2009) "CD4+ T Cells Regulate Pulmonary Metastasis of Mammary Carcinomas by Enhancing Protumor Properties of Macrophages," Cancer Cell 16(2):91-102, 24 pages.
Denfeld, R. W. et al. (Oct. 1996). "CD40 Is Functionally Expressed On Human Keratinocytes," Eur. J. Imrmmol. 26(10):2329-2334.
Dhupkar, P. et al. (Jun. 2018). "Anti-PD-1 Therapy Redirects Macrophages From an M2 to An M1 Phenotype Inducting Regression of OS Lung Metastases," Cancer Med. 7(6):2654-2664.
Diehl, L. et al. (Jul. 1999). "CD40 Activation In Vivo Overcomes Peptide-Induced Peripheral Cytotoxic T-Lymphocyte Tolerance And Augments Anti-Tumor Vaccine Efficacy," Nature Medicine 5(7):774-779.

(56) References Cited

OTHER PUBLICATIONS

Donepudi, M. et al. (May-Jun. 1999). "Signaling Through CD40 Enhances Cytotoxic T Lymphocyte Generation By CD8+ T Cells From Mice Bearing Large Tumors," Cancer Immunol. Immunother. 48(2-3):153-164.
Dong, H. et al. (Dec. 1999). "B7-H1, A Third Member Of The B7 Family, Co-Stimulates T-Cell Proliferation and Interleukin-10 Secretion," Nature Med. 5(12):1365-1369.
Eppihimer, M.J. et al. (Apr. 2002). "Expression and Regulation of the PD-L1 Immunoinhibitory Molecule on Microvascular Endothelial Cells," Microcirculation 9(2):133-145, 20 pages.
Espinosa, I. et al. (Jun. 2009). "Coordinate Expression of Colony-Stimulating Factor-1 and Colony-Stimulating Factor-1-Related Proteins Is Associated with Poor Prognosis in Gynecological and Nongynecological Leiomyosarcoma," Am. J. Pathol. 174(6):2347-2356.
Ferlin, W.G. et al. (Feb. 1998). "The Induction Of A Protective Response In Leishmania major-Infected BALB/c Mice With Anti-CD40 mAb," Eur. J. Immunol. 28(2):525-531.
Flores-Romo, L. et al. (Jan. 1997). "CD40 Ligation on Human Cord Blood CD34+ Hematopoietic Progenitors Induces Their Proliferation and Differentiation into Functional Dendritic Cells," J. Exp. Med. 185(2):341-349.
Flores-Romo, L. et al. (Jul. 1993). "Anti-CD40 Antibody Stimulates The VLA-4-Dependent Adhesion Of Normal and LFA-1-Deficient B Cells To Endothelium," Immunol. 79(3):445-451.
Foy, T.M. et al. (1996). "Immune Regulation By CD40 and Its Ligand GP39," Ann. Rev. of Immunol. 14:591-617.
Freeman, G.J. et al. (2000, e-pub. Oct. 2, 2000). "Engagement of the PD-1 Immunoinhibitory Receptor by a Novel B7 Family Member Leads to Negative Regulation of Lymphocyte Activation," J. Exp. Med. 192:1027-1034.
French, R.R. et al. (May 1999). "CD40 Antibody Evokes A Cytotoxic T-Cell Response That Eradicates Lymphoma and Bypasses T-Cell Help," Nature Medicine 5(5):548-553.
Funakoshi, S. et al. (Mar. 1996). "Differential in vitro and in vivo Antitumor Effects Mediated By Anti-CD40 and Anti-CD20 Monoclonal Antibodies Against Human B-Cell Lymphomas," J. Immunotherapy with Emphasis on Tumor Immunol. 19(2):93-101.
Galluzzi, L. et al. (2012). "Trial Watch: Experimental Toll-like Receptor Agonists For Cancer Therapy," OncoImmunology 1(5):699-716.
Grammar, A.C. et al. (1998). "TNF Receptor-Associated Factor-3 Signaling Mediates Activation of p38 and Jun N-Terminal Kinase, Cytokine Secretion, and Ig Production Following Ligation of CD40 on Human B Cells," J. Immunol. 161:1183-1193.
Grewal, I.S. et al. (1998). "CD40 and CD154 In Cell-Mediated Immunity," Ann. Rev. of Imrmmol. 16:111-135.
Grewal, I.S. et al. (Sep. 27, 1996). "Requirement For CD40 Ligand In Costimulation Induction, T Cell Activation, and Experimental Allergic Encephalomyelitis," Science 273(5283):1864-1867.
Grewal, I.S. et al. (Dec. 7, 1995). "Impairment Of Antigen-Specific T-Cell Priming In Mice Lacking CD40 Ligand," Nature 378(6557):617-620.
Grousson, J. et al. (Jun. 1998). "Effects Of CD40 Ligation On Human Keratinocyte Accessory Function," Archives of Dermatol. Res. 290(6):325-330.
Gruss, H.J. et al. (Oct. 1, 1994). "Expression and Function of CD40 on Hodgkin and Reed-Sternberg Cells and the Possible Relevance for Hodgkin's Disease," Blood 84(7):2305-2314.
Guo, Z. et al. (Jul. 29, 2015). "Combined Trabectedin and Anti-PD1 Antibody Produces a Synergistic Antitumor Effect in a Murine Model of Ovarian Cancer," J. Transl. Med. 13(247):1-13.
Guzman-Montes, G.Y. et al. (2009). "Indirect Patient Expenses For Antituberculosis Treatment In Tijuana, Mexico: Is Treatment Really Free?" Clin. Cancer Res. 3(10):778-787.
Haegel, H. et al. (2013, e-pub. Jul. 15, 2013). "A Unique Anti-CD115 Monoclonal Antibody Which Inhibits Osteolysis and Skews Human Monocyte Differentiation From M2-Polarized Macrophages Toward Dendritic Cells," mAbs 5 (5):736-747.

Heath, A.W. et al. (Aug. 1994). "Monoclonal Antibodies To Murine CD40 Define Two Distinct Functional Epitopes," Eur. J Immunol. 24(8):1828-1834.
Heckman, K.L. et al. (2007). "Fast-Tracked CTL: Rapid Induction Of Potent Anti-Tumor Killer T Cells in situ," Eur. J. Immunol. 37:1827-1835.
Hemmi, H. et al. (Dec. 7, 2000). "A Toll-Like Receptor Recognizes Bacterial DNA," Nature 408(6813):740-745.
Hirano, A. et al. (May 1, 1999). "Inhibition of Human Breast Carcinoma Growth by a Soluble Recombinant Human CD40 Ligand," Blood 93(9):2999-3007.
Hollenbaugh, D. et al. (Jul. 1995). "Expression Of Functional CD40 By Vascular Endothelial Cells," J. Exp. Med. 182:33-40.
Hoves, S. et al. (2006). "Monocyte-Derived Human Macrophages Mediate Anergy In Allogeneic T Cells and Induce Regulatory T Cells," J. Immunol. 177:2691-2698.
Hu-Lieskovan, S. et al. (Nov. 1, 2015). "Phase 1/2a Study of Double Immune Suppression Blockade by Combing a CSF1R Inhibitor (pexidartinlb/PLX3397) With an Anti PD-1 Antibody (pembrolizumab) to Treat Advance Melanoma and Other Solid Tumors," Ann. Oncol. 26(Suppl. 8):viii5-viii14 Abstract #18TiP, 1 pages.
Huang, A.Y. et al. (1994). "Bone Marrow-Derived Cells Present MHC Class I-Restricted Tumour Antigens In Priming Of Antitumour Immune Responses," Ciba Foundation Symp. 187:229-244.
Ingram, J.R. et al. (Apr. 10, 2018). "Anti-CTLA-4 Therapy Requires an Fc Domain For Efficacy," Proc. Natl. Acad. Sci. USA 115(15):3912-3917.
International Preliminary Report on Patentability dated Feb. 26, 2019, for PCT Application No. PCT/EP2017/070570, filed Aug. 14, 2017, 9 pages.
International Preliminary Report on Patentability, dated Jun. 25, 2019, for PCT Application No. PCT/EP2017/083696, filed Dec. 20, 2017.
International Search Report and Written Opinion for PCT Application No. PCT/EP2014/069451, dated Nov. 18, 2014, filed on Sep. 11, 2014, 13 pages.
International Search Report and Written Opinion dated Oct. 9, 2017, for PCT Application No. PCT/EP2017/070570, filed Aug. 14, 2017, 12 pages.
International Search Report and Written Opinion, dated Feb. 19, 2018, for PCT Application No. PCT/EP2017/083696, filed Dec. 20, 2017.
Ishida, T.K. et al. (Sep. 3, 1996). "TRAF5, a Novel Tumor Necrosis Factor Receptor-Associated Factor Family Protein, Mediates CD40 Signaling," Proc. Natl. Acad. Sci. USA 93(18):9437-9442.
Jenkins, M.K. et al. (Feb. 1, 1987). "Antigen Presentation By Chemically Modified Splenocytes Induces Antigen-Specific T Cell Unresponsiveness in vitro and in vivo," J. Exp. Med. 165:302-319.
Jeppson, J.D. et al. (1998). "Requirement for Dual Signals by Anti-CD40 and IL-4 for the Induction of Nuclear Factor-κB, IL-6, and IgE in Human B Lymphocytes," J. Immunol. 161:1738-1742.
Jiang, B. et al. (Feb. 11, 2005). "A Novel Peptide Isolated From a Phage Display Peptide Library With Trastuzumab Can Mimic Antigen Epitope of HER-2," J. Biol. Chem. 280(6):4656-4662.
Jones, K.W. et al. (Nov. 25, 1996). "Activated T Hybridomas Induce Upregulation Of B7-1 On Bystander B Lymphoma Cells By A Contact-Dependent Interaction Utilizing CD40 Ligand," Cellular Immunol. 174(1):42-53.
Kabat, E.A. et al. (1991). Sequences of Proteins of Immunological Interest, 5th Ed. Public Health Service, National Institutes of Health, Bethesda MD., Table of Contents, 21 pages.
Kandimalla, E.R. et al. (May 1, 2003). "Divergent Synthetic Nucleotide Motif Recognition Pattern: Design And Development Of Potent Immunomodulatory Oligodeoxyribonucleotide Agents With Distinct Cytokine Induction Profiles," Nucleic Acids Res. 31(9):2393-2400.
Kandimalla, E.R. et al. (Mar. 2001). "Effect Of Chemical Modifications Of Cytosine And Guanine In A CpG-Motif Of Oligonucleotides: Structure-Immunostimulatory Activity Relationships," Bioorg. Med. Chem. 9(3):807-813.
Kandimalla, E.R. et al. (May 10, 2005). "Immunomodulatory Oligonucleotides Containing A Cytosine-Phosphate-2'-Deoxy-7-

(56) References Cited

OTHER PUBLICATIONS

Deazaguanosine Motif As Potent Toll-Like Receptor 9 Agonists," Proc. Natl. Acad. Sci. USA. 102(19):6925-6930.
Kandimalla, E.R. et al. (Nov. 25, 2003). "A Dinucleotide Motif In Oligonucleotides Shows Potent Immunomodulatory Activity and Overrides Species-Specific Recognition Observed With CpG Motif," Proc. Natl. Acad. Sci. USA. 100(24):14303-14308.
Katada, Y. et al. (Jan. 1996). "B Cell-B Cell Interaction Through Intercellular Adhesion Molecule-1 And Lymphocyte Functional Antigen-1 Regulates Immunoglobulin E Synthesis By B Cells Stimulated With Interleukin-4 and Anti-CD40 Antibody," Eur. J. Immunol. 26(1):192-200.
Kawai, O. et al. (2008, e-pub. Jul. 31, 2008). "Predominant Infiltration of Macrophages and CD8+ T Cells in Cancer Nests Is a Significant Predictor of Survival in Stage IV Nonsmall Cell Lung Cancer," Cancer 6:1387-1395.
Kawai, T. et al. (May 2010, e-pub. Apr. 20, 2010). "The Role Of Pattern-Recognition Receptors In Innate Immunity: Update On Toll-Like Receptors," Nature Immunol. 11(5):373-384.
Kawamura, K. et al. (May 2009). "Detection of M2 Macrophages and Colony-Stimulating Factor 1 Expression In Serous and Mucinous Ovarian Epithelial Tumors," Pathol. Int. 59(5):300-305.
Keir et al. "PD-1 and Its Ligands in Tolerance and Immunity," Annu. Rev. Immunol. 26:677-704, (2008, e-pub. Jan. 2, 2008).
Keir, M.E. et al. (2008, e-pub. Jan. 2, 2008). "PD-1 and Its Ligands in Tolerance and Immunity," Annu. Rev. Immunol. 26:677-704.
Khalil, M. et al. (Jun. 1, 2007). "Anti-CD40 Agonist Antibodies: Preclinical and Clinical Experience," Update Cancer Ther.; 2(2):61-65, 9 pages.
Kiener, P.A. et al. (Nov. 15, 1995). "Stimulation of CD40 With Purified Soluble gp39 Induces Proinflammatory Responses In Human Monocytes," J. Immunol. 155(10):4917-4925.
Kim, K. et al. (Aug. 12, 2014). Eradication of Metastatic Mouse Cancers Resistant to Immune Checkpoint Blockade by Suppression of Myeloid-Derived Cells, Proc. Natl. Acad. Sci. USA 111(32):11774-11779.
Kipps, T.J. et al. (Jan. 1, 1985). "Importance of Immunoglobulin Isotype in Human Antibody-Dependent, Cell-Mediated Cytotoxicity Directed by Murine Monoclonal Antibodies," J. Exp. Med. 161(1):1-17.
Koch, F. et al. (Aug. 1, 1996). "High Level IL-12 Production By Murine Dendritic Cells: Upregulation Via MHC Class II and CD40 Molecules and Downregulation By IL-4 and IL-10," J. Exp. Med. 184(2):741-746.
Krug, A. et al. (Jul. 2001). "Identification of CpG Oligonucleotide Sequences With High Induction Of IFN-α/β In Plasmacytoid Dendritic Cells," Eur J Immunol, 31(7):2154-2163.
Kuester, K. et al. (2006). "Pharmacokinetics of Monoclonal Antibodies," Chapter 3 in "Pharmacokinetics and Pharmacodynamics of Biotech Drugs," Meibohm (Ed.), Wiley-VCH, pp. 45-91.
Kuipers, H. et al. (Sep. 2006). "Contribution Of The PD-1 Ligands/PD-1 Signaling Pathway To Dendritic Cell-Mediated CD4+ T Cell Activation," Eur. J. Immunol. 36(9):2472-2482.
Kuniyoshi, J.S. et al. (Apr. 10, 1999). "Dendritic Cell Secretion Of IL-15 Is Induced By Recombinant huCD40LT and Augments The Stimulation Of Antigen-Specific Cytolytic T Cells," Cellular Immunol. 193(1):48-58.
Lafferty, K.J. et al. (1975) "A New Analysis Of Allogeneic Interactions," Aust. J. Exp. Biol. Med. Sci. 53(pt. 1):27-42.
Langmead, B. et al. (Mar. 2012) "Fast Gapped-Read Alignment With Bowtie 2," Nat Methods 9(4):357-359, 8 pages.
Laoui, D. et al. (Oct. 7, 2014). "Functional Relationship Between Tumor-Associated Macrophages and Macrophage Colony-Stimulation Factor s Contributors to Cancer Progression," Front. Immunol 5:489, 15 pages.
Latchman, Y. et al. (Mar. 2001). "PD-L2 Is A Second Ligand For PD-1 and Inhibits T Cell Activation," Nature Immunol. 2(3):261-268.

Latchman, Y.E. et al. (Jul. 20, 2004). "PD-L1-Deficient Mice Show That PD-L1 on T Cells, Antigen-Presenting Cells, and Host Tissues Negatively Regulates T Cells," Proc. Natl. Acad. Sci. USA 101(29):10691-10696.
Lazaar, A.L. et al. (1998). "CD40-Mediated Signal Transduction in Human Airway Smooth Muscle," J. Immunol. 161:3120-3127.
Lee, H.H et al. (Feb. 16, 1999). "Specificities of CD40 Signaling: Involvement Of TRAF2 In CD40-Induced NF-κB Activation and Intercellular Adhesion Molecule-1 Up-Regulation," Proc. Natl Acad. Sci USA 96(4):1421-1426.
Lee, S.J. et al. (Feb. 6, 2006, e-pub. Jan. 9, 2006). "Interferon Regulatory Factor-1 Is Prerequisite To The Constitutive Expression and IFN-γ-Induced Upregulation of B7-H1 (CD274)," FEBS Lett. 580(3):755-762.
Lenschow, D.J. et al. (1996). "CD28/B7 System of T Cell Costimulation," Ann. Rev. Immunol. 14:233-258.
Li, F. et al. (Aug. 19, 2011). "Inhibitory Fcγ Receptor Engagement Drives Adjuvant and Anti-Tumor Activities Of Agonistic CD40 Antibodies," Science 333(6045):1030-1034, 13 pages.
Li, J. et al. (Dec. 2012). "Abstract P4-04-01: Combination Of Intratumoral CpG With Systemic Anti-OX40 and Anti-CTLA4 mAbs Eradicates Established Triple Negative Breast Tumors In Mice," Cancer Research (retrieved Mar. 26, 2015 from http://cancerres.aacrjournals.org/content/72/24_Supplement/P4-04-01.short), 4 pages.
Liang, S.C. et al. (Oct. 2003). "Regulation of PD-1, PD-L1, and PD-L2 Expression During Normal and Autoimmune Responses," Eur. J. Immunol. 33(10): 2706-2716.
Liang, X. et al. (Jun. 17, 2010, e-pub. Mar. 25, 2010). "Toll-like Receptor 9 Signaling By CpG-B Oligodeoxynucleotides Induces An Apoptotic Pathway In Human Chronic Lymphocytic Leukemia B Cells," Blood 115(24):5041-5052.
Lin, E.Y. et al. (Mar. 19, 2001). "Colony-Stimulating Factor 1 Promotes Progression of Mammary Tumors to Malignancy," J. Exp. Med. 193(6):727-740.
Liu, J. et al. (Jul. 1, 2007). "Plasma Cells From Multiple Myeloma Patients Express B7-H1 (PD-L1) and Increase Expression After Stimulation With IFN-γ and TLR Ligands Via A MyD88-, TRAF6-, and MEK-Dependent Pathway," Blood 110(1):296-304.
Loke, P. et al. (Apr. 29, 2003). "PD-L1 and PD-L2 Are Differentially Regulated By Th1 and Th2 Cells," Proc. Natl Acad. Sci. USA 100(9):5336-5341.
Longhi, M.P. et al. (Jul. 6, 2009). "Dendritic Cells Require A Systemic Type 1 Interferon Response To Mature and Induce CD4+ Th1 Immunity With Poly IC As Adjuvant," J Exp Med 206(7):1589-1602.
Mackey, M.F. et al. (1998). "Cutting Edge: Dendritic Cells Require Maturation via CD40 to Generate Protective Antitumor Immunity," J. Immunol. 161:2094-2098.
Mackey, M.F. et al. (Apr. 1998). "The Role Of CD40/CD154 Interactions In The Priming, Differentiation, and Effector Function Of Helper and Cytotoxic T Cell," J. Leukocyte Biol. 63(4):418-428.
Mackey, M.F. et al. (Jul. 1, 1997). "Protective Immunity Induced by Tumor Vaccines Requires Interaction between CD4Oandits Ligand, CD154," Cancer Research 57:2569-2574.
Magiera-Mularz, K. et al. (Jan. 22, 2021). "Human and Mouse PD-L1: Similar Molecular Structure, But Different Druggability Profiles," iScience 24(101960):1-26, Supplemental Information.
Mahl, R.S. et al. (2013, e-pub. Sep. 2, 2013). "Sweeten PAMPs: Role of Sugar Complexed PAMPs in Innate Immunity and Vaccine Biology," Front Immunol 4:248.
Mantovani, A et al. (2004, e-pub. May 19, 2004). "Tumour-Associated Macrophages As A Prototypic Type II Polarised Phagocyte Population: Role In Tumour Progression," Eur. J. Cancer 40(11):1660-1667.
Mantovani, A. et al. (Apr. 2010, e-pub. Feb. 9, 2010). "Macrophages, Innate Immunity and Cancer: Balance, Tolerance, and Diversity," Curr. Opin. Immunol. 22(2):231-237.
Martin-Fontecha, A. et al. (1999). "Triggering of Murine NK Cells by CD40 and CD86 (B7-2)," J. Immunol. 162:5910-5916.
Martinez, F.O. et al. (Feb. 28, 2013). "Genetic Programs Expressed In Resting and IL-4 Alternatively Activated Mouse and Human Macrophages: Similarities and Differences," Blood 21(9):e57-e69.

(56) References Cited

OTHER PUBLICATIONS

Matsusaki, M. et al. (2019). "Three-Dimensional Cell Culture Technique and Pathophysiology," Advanced Drug Delivery Reviews, 74:95-103, 36 pages.

Mayumi, M. et al. (Dec. 1995). "Session II: Allergy and Intracellular Signal Transmission Mechanisms: Role of LFA-1/ICAM-1-Dependent Cell Adhesion In CD40-Mediated Inhibition Of Anti-IgM Antibody-Induced B-Cell Death," J. Allergy & Clin. Immunol. 96(6 Pt. 2):1136-1144.

McDyer, J.F. et al. (1999). "Differential Effects of CD40 Ligand/Trimer Stimulation on the Ability of Dendritic Cells to Replicate and Transmit HIV Infection: Evidence for CC-Chemokine-Dependent and -Independent Mechanisms," J. Immunol. 162:3711-3717.

Meng, Y. et al. (Oct. 10, 2005). "Successful Combination Of Local CpG-ODN and Radiotherapy In Malignant Glioma," Int J Cancer 116(6):992-997.

Mitchem, J.B. et al. (Feb. 1, 2013, e-pub. Dec. 5, 2012). "Targeting Tumor-Infiltrating Macrophages Decreases Tumor-Initiating Cells, Relieves Immunosuppression, and Improves Chemotherapeutic Responses," Cancer Res. 73(3):1128-1141.

Mortazavi, A. et al. (Jul. 2008, e-pub. May 30, 2008). "Mapping and Quantifying Mammalian Transcriptomes By RNA-Seq," Nat Methods 5(7):621-628.

Murad, Y.M. et al. (2009). "CpG Oligodeoxynucleotides As TLR9 Agonists: Therapeutic Applications In Cancer," BioDrugs. 23(6):361-375.

Ngan, H.Y. et al. (1999). "Proto-oncogenes and p53 Protein Expression in Normal Cervical Stratified Squamous Epithelium and Cervical Intra-Epithelial Neoplasia," Eur J. Cancer 35(10):1546-1550.

Nielsen, C. et al. (Jun. 2005. e-pub. Sep. 19, 2005). "Alternative Splice Variants Of The Human PD-1 Gene," Cell. Immunol. 235(2): 109-116.

Nishimura, H. et al. (Jan. 12, 2001). "Autoimmune Dilated Cardiomyopathy In PD-1 Receptor-Deficient Mice," Science 291(5502):319-322.

Nishimura, H. et al. (1999). "Development Of Lupus-Like Autoimmune Diseases By Disruption Of The PD-1 Gene Encoding An ITIM Motif-Carrying Immunoreceptor," Immunity 11(2):141-151.

Nishimura, H. et al. (May 1996). "Developmentally Regulated Expression Of The PD-1 Protein On The Surface Of Double-Negative (CD4-CD8-) Thymocytes," Int. Immunol. 8(5):773-780.

Noelle, R.J (1998). "CD40 and Its Ligand In Cell-Mediated Immunity," Agents & Actions Suppl. 49:17-22.

Orre, M. et al. (Apr. 1999). "Macrophages and Microvessel Density In Tumors Of The Ovary," Gynecol. Oncol. 73(1):47-50.

Parsa, A.T. et al. (Jan. 2007, e-pub. Dec. 20, 2006). "Loss of Tumor Suppressor PTEN Function Increases B7-H1 Expression and Immunoresistance In Glioma," Nat. Med. 13(1):84-88.

Paulie, S. et al. (1985). "A p50 Surface Antigen Restricted To Human Urinary Bladder Carcinomas and B LYMphocytes," Cancer Immunol. Immunother. 20(1):23-28.

Price, F. et al. (Feb. 1993). "Colony-Stimulating Factor-1 In Primary Ascites Of Ovarian Cancer Is A Significant Predictor Of Survival," Am J. Obstet. Gynecol. 168(2):520-527.

Pullen S.S. et al. (May 14, 1999). "CD40 Signaling through Tumor Necrosis Factor Receptor-associated Factors (TRAFs)," J. Biol Chem 274(20):14246-14254.

Pullen, S.S. et al. (Aug. 25, 1998). "CD40-Tumor Necrosis Factor Receptor-Associated Factor (TRAF) Interactions: Regulation Of CD40 Signaling Through Multiple TRAF Binding Sites and TRAF Hetero-Oligomerization," Biochemistry 37(34):11836-11845.

Putta, M.R. et al. (2006, e-pub. Jun. 23, 2006). "Novel Oligodeoxynucleotide Agonists of TLR9 Containing N3-Me-dC or N1-Me-dG Modifications," Nucleic Acids Res 34(11):3231-3238.

Richman, L.P. et al. (2013, e-pub. Nov. 5, 2013). "Role of Crossliniking for Agonistic CD40 Monoclonal Antibodies as Immune Therapy of Cancer," Cancer Immunology Research, 2(1):19-26, 12 pages.

Riemer, A.B. et al. (2005). "Matching of Trastuzumab (Herceptin®) Epitope Mimics onto the Surface of Her-2/neu—A New Method of Epitope Definition," Molecular Immunology 42:1121-1124.

Ries, C.H. et al. (Jun. 16, 2014, e-pub. Jun. 2, 2014). "Targeting Tumor-Associated Macrophages With Anti-CSF-1R Antibody Reveals A Strategy For Cancer Therapy," Cancer Cell 25(6):846-859.

Rothenfusser, S. et al. (Dec. 2002). "Plasmacytoid Dendritic Cells: The Key To CpG," Human Immunology 63(12):1111-1119.

Roy, M. et al. (Feb. 1995). "Studies On The Interdependence Of gp39 and B7 Expression and Function During Antigen-Specific Immune Responses," Eur. J. Immunol. 25(2):596-603.

Ruggiero, G. et al. (May 15, 1996). "CD40 Expressed On Thymic Epithelial Cells Provides Costimulation For Proliferation But Not For Apoptosis Of Human Thymocytes," J. Immunol. 156(10):3737-3746.

Sandmann, T. et al. (Jan. 1, 2014, e-pub. Oct. 15, 2013). "gCMAP: User-Friendly Connectivity Mapping With R," Bioinformatics 30(1):127-128.

Santos-Argumedo, L. et al. (Jul. 1994). "Antibodies To Murine CD40 Protect Normal and Malignant B Cells From Induced Growth Arrest," Cellular Immunol. 156(2):272-285.

Schaniel, C. et al. (Aug. 3, 1998). "Activated Murine B Lymphocytes and Dendritic Cells Produce a Novel CC Chemokine which Acts Selectively on Activated T Cells," J. Exp. Med. 188(3):451-463.

Schmieder, A. et al. (Aug. 2012, e-pub. Feb. 13, 2012). "Differentiation and Gene Expression Profile Of Tumor-Associated Macrophages," Semin Cancer Biol. 22(4):289-297.

Schoenberger, S.P. et al. (Jun. 4, 1998). "T-Cell Help For Cytotoxic T Lymphocytes Is Mediated By CD40-CD40L Interactions," Nature 393(6684):480-483.

Scholl, S. et al. (1994). "Circulating Levels Of Colony-Stimulating Factor 1 As A Prognostic Indicator In 82 Patients With Epithelial Ovarian Cancer," Br. J. Cancer 62:342-346.

Schreiner, B. et al. (Oct. 2004). "Interferon-Beta Enhances Monocyte and Dendritic Cell Expression Of B7-H1 (PD-L1), A Strong Inhibitor Of Autologous T-Cell Activation: Relevance For The Immune Modulatory Effect In Multiple Sclerosis," J. Neuroimmunol. 155(1-2):172-182.

Schroder, K. et al. (Jun. 2007). "PU.1 and ICSBP control constitutive and IFN-γ-regulated Tlr9 Gene Expression In Mouse Macrophages," J. Leukoc. Biol. 81(6):1577-1590.

Sherr, C.J. et al. (Jul. 1985). "The c-fms Proto-Oncogene Product Is Related To The Receptor For The Mononuclear Phagocyte Growth Factor, CSF-1," Cell 41(3):665-676.

Sherr, C.J. et al. (May 15, 1989). "Inhibition of Colony-Stimulating Factor-i Activity By Monoclonal Antibodies To The human CSF-1 Receptor," Blood 73(7):1786-1793.

Sloan-Lancaster et al. (May 13, 1993) "Induction of T-Cell Anergy by Altered T-Cell-Receptor Ligand on Live Antigen-Presenting Cells," Nature 363:156-159.

Sotomayor, E.M. et al. (Jul. 1999). "Conversion Of Tumor-Specific CD4+ T-Cell Tolerance To T-Cell Priming Through in vivo Ligation Of CD40," Nature Medicine 5(7):780-787.

Stanley, E.R. et al. (Jun. 2014). "CSF-1 Receptor Signaling in Myeloid Cells," Cold Spring Harb. Prespect. Biolo. 6(6):a021857, 21 pages.

Steidl, C. et al. (Mar. 11, 2010). "Tumor-Associated Macrophages and Survival in Classic Hodgkins's Lymphoma," N. Engl. J.Med. 362(10):875-885.

Steinhagen, F. et al. (Apr. 2011, e-pub. Aug. 14, 2011). "TLR-Based Immune Adjuvants," Vaccine 29(17):3341-3355, 33 pages.

Su, H. et al. (Jun. 2014). "Identification of an Isoform of Colony-Stimulationg Factor 1 Receptor mRNA in the Rat Testis," Biochem. Genet. 52(5-6):310-319.

Subramanian, A. et al. (Oct. 25, 2005). "Gene Set Enrichment Analysis: A Knowledge-Based Approach For Interpreting Genome-Wide Expression Profiles," Proc. Natl. Acad. Sci. USA 102(43):15545-15550.

Sutherland, C.L. et al. (1999). "An 11-Amino Acid Sequence in the Cytoplasmic Domain of CD40 Is Sufficient for Activation of c-Jun N-Terminal Kinase, Activation of MAPKAP Kinase-2, Phosphorylation

(56) References Cited

OTHER PUBLICATIONS of IkBa, and Protection of WEHI-231 Cells from Anti-IgM-lnduced Growth Arrest," J. Immunol. 162:4720-4730.
Swierczak, A. et al. (Aug. 2014, e-pub. Apr. 29, 2014). "The Promotion of Breast Cancer Metastasis Caused by Inhibition of CSF-1R Signaling Is Blocked by Targeting the G-CSF Receptor," Cancer Immunol. Res. 2(8):765-766.
Séguin, R. et al. (Feb. 1999). "Sensitized Lymphocytes and CD40 Ligation Augment Interleukin-12 Production By Human Dendritic Cells In Response To Toxoplasma gondii," J. Infect. Diseases 179(2):467-474.
Toes, R.E.M. et al. (Dec. 1998). "CD40-CD40 Ligand Interactions and Their Role In Cytotoxic T Lymphocyte Priming and Anti-Tumor Immunity," Seminars in Immunol. 10(6):443-448.
Tseng, S.-Y. et al. (Apr. 2, 2001). "B7-Dc, A New Dendritic Cell Molecule with Potent Costimulatory Properties for T Cells," J. Exp. Med. 193(7):839-846.
Tsukamoto, N. et al. (Feb. 16, 1999). "Two Differently Regulated Nuclear Factor κB Activation Pathways Triggered By The Cytoplasmic Tail Of CD40," Proc. Natl. Acad. Sci. USA 96(4):1234-1239.
Tutt, A.L. et al. (1998). "Monoclonal Antibody Therapy of B Cell Lymphoma: Signaling Activity on Tumor Cells Appears More Important Than Recruitment of Effectors," J. Immunol. 161:3176-3185.
Ueda, H. et al. (May 29, 2003, e-pub. Apr. 30, 2003). "Association Of The T-Cell Regulatory Gene CTLA4 With Susceptibility To Autoimmune Disease," Nature 423(6939):506-511.
Uejima, Y. et al. (Jul. 1996). "Effect Of Interleukin-10 On Anti-CD40- and Interleukin-4-Induced Immunoglobulin E Production By Human Lymphocytes," Int. Arch. of Allergy & Immunol. 110(3):225-232.
Vajdos, F. et al. (2002) "Comprehensive Functional Maps of the Antigen Binding Site of an Anti-ErbB2 Antibody Obtained with Shotgun Scanning Mutagenesis," J. Mol. Biol. 320:415-428.
Viola, A. et al. (Jul. 5, 1996). "T Cell Activation Determined by T Cell Receptor Number and Tunable Thresholds," Science 273:104-106.
Von Leoprechting, A. et al. (Mar. 15, 1999). "Stimulation of CD40 on Immunogenic Human Malignant Melanomas Augments Their Cytotoxic T Lymphocyte-mediated Lysis and Induces Apoptosis," Cancer Res. 59:1287-1294.
Vonderheide, R.H. et al. (Mar. 1, 2007). "Clinical Activity and Immune Modulation In Cancer Patients Treated With CP-870,893, A Novel CD40 Agonist Monoclonal Antibody," J Clin Oncol 25(7):876-883.
Waltenbaugh, C. et al. (2008). Immunology Lippincott's Illustrated Reviews. Philadelphia: Wolters Kluwer Health/Lippincott's Williams & Wilkins, p. 17, 5 pages.
Wan, B. et al. (2006). "Aberrant Regulation of Synovial T Cell Activation by Soluble Costimulatory Molecules in Rheumatoid Arthritis," J Immunol. 177:8844-8850.
Weiner, G.J. et al. (Sep. 30, 1997). "Immunostimulatory Oligodeoxynucleotides Containing The CpG Motif Are Effective As Immune Adjuvants In Tumor Antigen Immunization," Proc. Natl. Acad. Sci. USA 94(20):10833-10837.
White A.L. et al. (Aug. 15, 2011, e-pub. Jul. 8, 2011). "Interaction with FcgammaRIIB is Critical for the Agonistic Activity of Anti-CD40 Monoclonal Antibody," J Immunol. 187(4):1754-1763.
White, C.A. et al. (2001). "Antibody-Targeted Immunotherapy For Treatment of Malignancy," Annual Review of Medicine 52:125-145.
WHO Drug Information (2014). "International Nonproprietary Names for Pharmaceutical Substances (INN)," 28(2):111, 84 pages.
Wyckoff, J.B. et al. (Mar. 15, 2007). "Direct Visualization of Macrophage-Assisted Tumor Cell Intravasation in Mammary Tumors," Cancer Res. 67(6):2649-2656.
Xiong, Y. et al. (Jan. 14, 2011). "A CSF-1 Receptor Phosphotyrosine 559 Signaling Pathway Regulates Receptor Ubiquitination and Tyrosine Phosphorylation," J. Biol. Chem. 286(2):952-960.
Yamazaki, T. et al. (2002). "Expression of Programmed Death 1 Ligands by Murine T Cells and APC1," J. Immunol. 169:5538-5545.
Yellin, M.J. et al. (Aug. 1995). "Ligation Of CD40 On Fibroblasts Induces CD54 (ICAM-1) and CD106 (VCAM-1) Up-Regulation And IL-6 Production and Proliferation," J. Leukocyte Biol. 58(2):209-216.
Zhang, L. et al. (Apr. 16, 2020). "Single-Cell Analyses Inform Mechanisms of Myeloid-Targeted Therapies in Colon Cancer," Cell 181(2):442-459, and Supplemental Information, 47 pages.
Zhong, X. et al. (Sep. 2007). "PD-L2 Expression Extends Beyond Dendritic Cells/Macrophages To B1 Cells Enriched For VH11/VH12 and Phosphatidylcholine Binding," Eur. J. Immunol. 37(9):2405-2410.
Zhu, Y. et al. (Sep. 15, 2014, e-pub. Jul. 31, 2014). "CSF1/CSF1R Blockade Reprograms Tumor-Inflitrating Macrophages and Improves Response to T-Cell Checkpoint Immunotherapy in Pancreatic Cancer Models," Cancer Res. 74(18):5057-5069.
Clinical Trials.Gov (Sep. 14, 2021). NCT03336216—"A Study of Cabiralizumab Given With Nivolumab With and Without Chemotherapy in Patients With Advanced Pancreatic Cancer," 9 pages.
Columbus, G. (Feb. 18, 2020). "Nivolumab/Cabiralizumab Combo Misses PFS Endpoint In Pancreatic Cancer," OncLive®, 3 pages.
Fares, C.M. et al., (Jan. 2019). "Mechanisms of Resistance to Immune Checkpoint Blockage: Why Does Checkpoint inhibitor immunotherapy Not Work For all Patients?," Am. Soc. Clin. Oncol. Educ. Book 39:147-164.
Lianfang, Q. et al. (Jan. 1, 1997). Biological Effect of Monoclonal Antibodies Against CSF1 & CSF1R on Human Hepatic Cancer Cells Transplanted I Nude Mice,: Tumor 4:207-208, Chinese with English translation, 4 pages.
Ruffell, B. et al. (Apr. 13, 2015). "Macrophages and Therapeutic Resistance in Cancer," Cancer Cell 27 (4):462-472.
Anonymous (Apr. 1, 1988). "Macrophage Colony-Stimulating Factor 1 Receptor (P07333),", 36 pages.
Ries, C.H. et al. (2015). "CSF-1/CSF-1 R Targeting Agents in Clinical Development For Cancer Therapy," Current Opinion in Pharmacology, 23:45-51.
Sica, A. et al. (2014) "Macrophage Plasticity and Polarization in Liver Homeostasis and Pathology," Hepatology, 59:2035-2043.

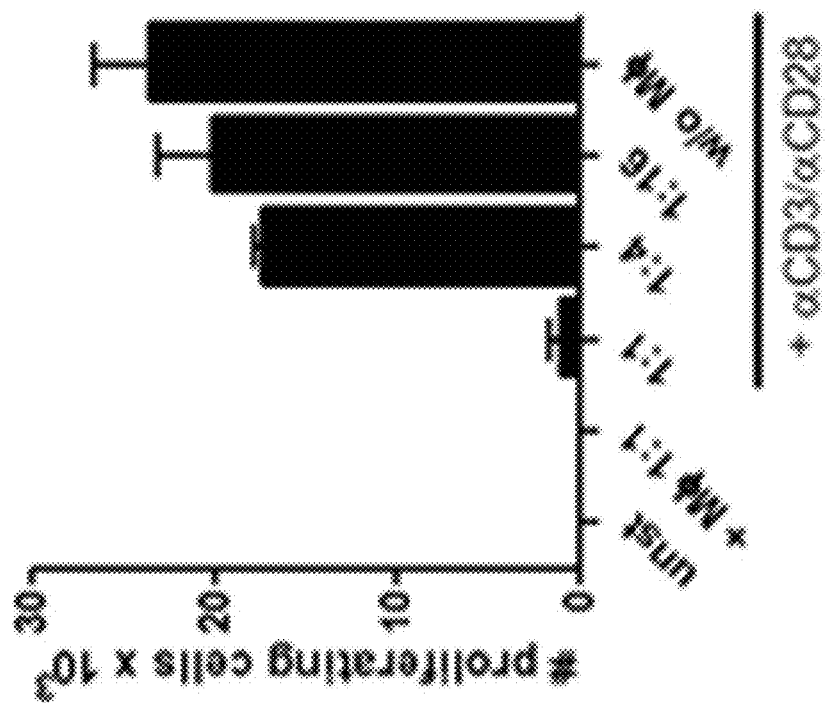

METHODS FOR TREATING COLON CANCER OR INHIBITING CELL PROLIFERATION BY ADMINISTERING A COMBINATION OF ANTIBODIES AGAINST HUMAN CSF-1R AND ANTIBODIES AGAINST HUMAN PD-L1

CROSS REFERENCES TO RELATED APPLICATIONS

This application is a continuation of U.S. application Ser. No. 15/957,387 filed Apr. 19, 2018, now abandoned, which is a continuation of U.S. application Ser. No. 15/223,897, filed Jul. 29, 2016, now abandoned, which is a continuation of U.S. application Ser. No. 14/485,140, filed Sep. 12, 2014, now abandoned, which claims priority to European Application No. 13184120.7, filed Sep. 12, 2013.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 146392030203SEQLIST.TXT, date recorded: Jun. 4, 2020, size: 99 KB).

The present invention relates to the combination therapy of specific antibodies which bind human CSF-1R with specific antibodies which bind human PD-L1.

BACKGROUND OF THE INVENTION

CSF-1R and CSF-1R Antibodies

The human CSF-1 receptor (CSF-1R; colony stimulating factor 1 receptor; synonyms: M-CSF receptor; Macrophage colony-stimulating factor 1 receptor, Fms proto-oncogene, c-fms, SEQ ID NO: 62) is known since 1986 (Coussens, L., et al., Nature 320 (1986) 277-280). CSF-1R is a growth factor and encoded by the c-fms proto-oncogene (reviewed e.g. in Roth, P., and Stanley, E. R., Curr. Top. Microbiol. Immunol. 181 (1992) 141-167).

CSF-1R is the receptor for CSF-1 (colony stimulating factor 1, also called M-CSF, macrophage colony-stimulating factor) and mediates the biological effects of this cytokine (Sherr, C. J., et al., Cell 41 (1985) 665-676). The cloning of the colony stimulating factor-1 receptor (CSF-1R) (also called c-fms) was described for the first time in Roussel, M. F., et al., Nature 325 (1987) 549-552. In that publication, it was shown that CSF-1R had transforming potential dependent on changes in the C-terminal tail of the protein including the loss of the inhibitory tyrosine 969 phosphorylation which binds Cbl and thereby regulates receptor down regulation (Lee, P. S., et al., Embo J. 18 (1999) 3616-3628). Recently a second ligand for CSF-1R termed interleukin-34 (IL-34) was identified (Lin, H., et al, Science 320 (2008) 807-811).

Currently two CSF-1R ligands that bind to the extracellular domain of CSF-1R are known. The first one is CSF-1 (colony stimulating factor 1, also called M-CSF, macrophage; SEQ ID NO: 86) and is found extracellularly as a disulfide-linked homodimer (Stanley, E. R. et al., Journal of Cellular Biochemistry 21 (1983) 151-159; Stanley, E. R. et al., Stem Cells 12 Suppl. 1 (1995) 15-24). The second one is IL-34 (Human IL-34; SEQ ID NO: 87) (Hume, D. A., et al, Blood 119 (2012) 1810-1820). The main biological effects of CSF-1R signaling are the differentiation, proliferation, migration, and survival of hematopoietic precursor cells to the macrophage lineage (including osteoclast). Activation of CSF-1R is mediated by its CSF-1R ligands, CSF-1 (M-CSF) and IL-34. Binding of CSF-1 (M-CSF) to CSF-1R induces the formation of homodimers and activation of the kinase by tyrosine phosphorylation (Li, W. et al, EMBO Journal. 10 (1991) 277-288; Stanley, E. R., et al., Mol. Reprod. Dev. 46 (1997) 4-10).

The biologically active homodimer CSF-1 binds to the CSF-1R within the subdomains D1 to D3 of the extracellular domain of the CSF-1 receptor (CSF-1R-ECD). The CSF-1R-ECD comprises five immunoglobulin-like subdomains (designated D1 to D5). The subdomains D4 to D5 of the extracellular domain (CSF-1R-ECD) are not involved in the CSF-1 binding (Wang, Z., et al Molecular and Cellular Biology 13 (1993) 5348-5359). The subdomain D4 is involved in dimerization (Yeung, Y-G., et al Molecular & Cellular Protcomics 2 (2003) 1143-1155; Pixley, F. J., et al., Trends Cell Biol. 14 (2004) 628-638).

Further signaling is mediated by the p85 subunit of P3K and Grb2 connecting to the PI3K/AKT and Ras/MAPK pathways, respectively. These two important signaling pathways can regulate proliferation, survival and apoptosis. Other signaling molecules that bind the phosphorylated intracellular domain of CSF-1R include STAT, STAT3, PLCy, and Cbl (Bourette, R. P. and Rohrschneider, L. R., Growth Factors 17 (2000) 155-166).

CSF-1R signaling has a physiological role in immune responses, in bone remodeling and in the reproductive system. The knockout animals for either CSF-1 (Pollard, J. W., Mol. Reprod. Dev. 46 (1997) 54-61) or CSF-1R (Dai, X. M., et al., Blood 99 (2002) 111-120) have been shown to have osteopetrotic, hematopoietic, tissue macrophage, and reproductive phenotypes consistent with a role for CSF-1R in the respective cell types.

Sherr, C. J., et al., Blood 73 (1989) 1786-1793 relates to some antibodies against CSF-1R that inhibit the CSF-1 activity. Ashmun, R. A., et al., Blood 73 (1989) 827-837 relates to CSF-1R antibodies. Lenda, D., et al., Journal of Immunology 170 (2003) 3254-3262 relates to reduced macrophage recruitment, proliferation, and activation in CSF-1-deficient mice results in decreased tubular apoptosis during renal inflammation. Kitaura, H., et al., Journal of Dental Research 87 (2008) 396-400 refers to an anti-CSF-1 antibody which inhibits orthodontic tooth movement. WO 2001/030381 mentions CSF-1 activity inhibitors including antisense nucleotides and antibodies while disclosing only CSF-1 antisense nucleotides. WO 2004/045532 relates to metastases and bone loss prevention and treatment of metastatic cancer by a CSF-1 antagonist disclosing as antagonist anti-CSF-1-antibodies only. WO 2005/046657 relates to the treatment of inflammatory bowel disease by anti-CSF-1-antibodies. US 2002/0141994 relates to inhibitors of colony stimulating factors. WO 2006/096489 relates to the treatment of rheumatoid arthritis by anti-CSF-1-antibodies. WO 2009/026303 and WO 2009/112245 relate to certain anti-CSF-1R antibodies binding to CSF-AR within the first three subdomains (D1 to D3) of the Extracellular Domain (CSF-1R-ECD). WO2011/123381(A1) relates to antibodies against CSF-1R. WO2011/070024 relate to certain anti-CSF-1R antibodies binding to CSF-1R within the dimerization domain (D4 to D5).

PD-L1 and PD-L1 Antibodies

Co-stimulation or the provision of two distinct signals to T-cells is a widely accepted model of lymphocyte activation of resting T lymphocytes by antigen-presenting cells (APCs). Lafferty et al., *Aust. J. Exp. Biol. Med. Sci.* 53: 27-42 (1975).

This model further provides for the discrimination of self from non-self and immune tolerance. Bretscher et al., *Science* 169: 1042-1049 (1970); Bretscher, P. A., *P.N.A.S. USA* 96: 185-190 (1999); Jenkins et al., *J. Exp. Med.* 165: 302-319 (1987). The primary signal, or antigen specific signal, is transduced through the T-cell receptor (TCR) following recognition of foreign antigen peptide presented in the context of the major histocompatibility-complex (MHC). The second or co-stimulatory signal is delivered to T-cells by co-stimulatory molecules expressed on antigen-presenting cells (APCs), and induce T-cells to promote clonal expansion, cytokine secretion and effector function. Lenschow et al., *Ann. Rev. Immunol.* 14:233 (1996). In the absence of co-stimulation, T-cells can become refractory to antigen stimulation, do not mount an effective immune response, and further may result in exhaustion or tolerance to foreign antigens.

The simple two-signal model can be an oversimplification because the strength of the TCR signal actually has a quantitative influence on T-cell activation and differentiation. Viola et al., *Science* 273: 104-106 (1996); Sloan-Lancaster, *Nature* 363: 156-159 (1993). Moreover, T-cell activation can occur even in the absence of co-stimulatory signal if the TCR signal strength is high. More importantly, T-cells receive both positive and negative secondary co-stimulatory signals. The regulation of such positive and negative signals is critical to maximize the host's protective immune responses, while maintaining immune tolerance and preventing autoimmnunity.

Negative secondary signals seem necessary for induction of T-cell tolerance, while positive signals promote T-cell activation. While the simple two-signal model still provides a valid explanation for naive lymphocytes, a host's immune response is a dynamic process, and co-stimulatory signals can also be provided to antigen-exposed T-cells.

The mechanism of co-stimulation is of therapeutic interest because the manipulation of co-stimulatory signals has shown to provide a means to either enhance or terminate cell-based immune response. Recently, it has been discovered that T cell dysfunction or anergy occurs concurrently with an induced and sustained expression of the inhibitory receptor, programmed death 1 polypeptide (PD-1). As a result, therapeutic targeting PD-1 and other molecules which signal through interactions with PD-1, such as programmed death ligand 1 (PD-L1) and programmed death ligand 2 (PD-L2) are an area of intense interest. The inhibition of PD-L1 signaling has been proposed as a means to enhance T cell immunity for the treatment of cancer (e.g., tumor immunity) and infection, including both acute and chronic (e.g., persistent) infection. However, as an optimal therapeutic directed to a target in this pathway has yet to be commercialized, a significant unmet medical need exists. Antibodies against PD-L1 are described e.g. in WO 2010/077634.

SUMMARY OF THE INVENTION

The invention comprises the combination therapy of an antibody which binds to human CSF-1R with an antibody which binds to human PD-L1 for use in the treatment of cancer, for use in the prevention or treatment of metastasis, for use in the treatment inflammatory diseases, for use in the treatment of bone loss, for use in treating or delaying progression of an immune related disease such as tumor immunity, or for use in stimulating an immune response or function, such as T cell activity.

The invention further comprises the use of antibody which binds to human CSF-1R for the manufacture of a medicament for use in the treatment of cancer, for use in the treatment inflammatory diseases, for use in the treatment of bone loss, for use in treating or delaying progression of an immune related disease such as tumor immunity, or for use in stimulating an immune response or function, such as T cell activity, wherein the antibody is administered in combination with an antibody which binds to human PD-L1.

The antibody which binds to human CSF-1R used in the combination therapy is characterized in comprising
  a) a heavy chain variable domain VH of SEQ ID NO:23 and a light chain variable domain VL of SEQ ID NO:24, or
  b) a heavy chain variable domain VH of SEQ ID NO:31 and a light chain variable domain VL of SEQ ID NO:32, or
  c) a heavy chain variable domain VH of SEQ ID NO:39 and a light chain variable domain VL of SEQ ID NO:40, or
  d) a heavy chain variable domain VH of SEQ ID NO:47 and a light chain variable domain VL of SEQ ID NO:48, or
  e) a heavy chain variable domain VH of SEQ ID NO:55 and a light chain variable domain VL of SEQ ID NO:56;
and the antibody which binds to human PD-L1 used in the combination therapy is characterized in comprising
  a) a heavy chain variable domain VH of SEQ ID NO:89 and a light chain variable domain VL of SEQ ID NO:92, or
  b) a heavy chain variable domain VH of SEQ ID NO:90 and a light chain variable domain VL of SEQ ID NO:93, or
  c) a heavy chain variable domain VI of SEQ ID NO:90 and a light chain variable domain VL of SEQ ID NO:94, or
  d) a heavy chain variable domain VH of SEQ ID NO:90 and a light chain variable domain VL of SEQ ID NO:95, or
  e) a heavy chain variable domain VH of SEQ ID NO:90 and a light chain variable domain VL of SEQ ID NO:96, or
  f) a heavy chain variable domain VH of SEQ ID NO:90 and a light chain variable domain VL of SEQ ID NO:97, or
  g) a heavy chain variable domain VH of SEQ ID NO:90 and a light chain variable domain VL of SEQ ID NO:98, or
  h) a heavy chain variable domain VH of SEQ ID NO:90 and a light chain variable domain VL of SEQ ID NO:99, or
  i) a heavy chain variable domain VH of SEQ ID NO:90 and a light chain variable domain VL of SEQ ID NO:100, or
  j) a heavy chain variable domain VH of SEQ ID NO:90 and a light chain variable domain VL of SEQ ID NO:101, or
  k) a heavy chain variable domain VH of SEQ ID NO:90 and a light chain variable domain VL of SEQ ID NO:102, or
  l) a heavy chain variable domain VH of SEQ ID NO:90 and a light chain variable domain VL of SEQ ID NO:103, or m) a heavy chain variable domain VH of SEQ ID NO:90 and a light chain variable domain VL of SEQ ID NO:104, or
n) a heavy chain variable domain VH of SEQ ID NO:90 and a light chain variable domain VL of SEQ ID NO:105, or
o) a heavy chain variable domain VH of SEQ ID NO:90 and a light chain variable domain VL of SEQ ID NO:106, or
p) a heavy chain variable domain VH of SEQ ID NO:91 and a light chain variable domain VL of SEQ ID NO:107.

In one embodiment the antibody is for use in the treatment of cancer.

In one embodiment the antibody is for use in the prevention or treatment of metastasis.

In one embodiment the antibody is, for use in the treatment of bone loss.

In one embodiment the antibody is for use in the treatment of inflammatory diseases.

In one embodiment the antibody is for use in treating or delaying progression of an immune related disease such as tumor immunity.

In one embodiment the antibody is for use in stimulating an immune response or function, such as T cell activity.

The invention further comprises antibody which binds to human CSF-1R wherein the antibody is administered in combination with an antibody which binds to human PD-L1 for use in
  i) the inhibition of cell proliferation in CSF-1R ligand-dependent and/or CSF-1 ligand-independent CSF-1R expressing tumor cells;
  ii) the inhibition of cell proliferation of tumors with CSF-1R ligand-dependent and/or CSF-1R ligand-independent CSF-1R expressing macrophage infiltrate;
  iii) the inhibition of cell survival (in CSF-1R ligand-dependent and/or CSF-1R ligand-independent) CSF-1R expressing monocytes and macrophages; and/or
  iv) the inhibition of cell differentiation (in CSF-1R ligand-dependent and/or CSF-1R ligand-independent) CSF-1R expressing monocytes into macrophages;
  wherein the antibody is administered in combination with an antibody which binds to human PD-L1;
    wherein the antibody which binds to human CSF-1R used in the combination therapy is characterized in comprising
      a) a heavy chain variable domain VH of SEQ ID NO:23 and a light chain variable domain VL of SEQ ID NO:24, or
      b) a heavy chain variable domain VH of SEQ ID NO:31 and a light chain variable domain VL of SEQ ID NO:32, or
      c) a heavy chain variable domain VH of SEQ ID NO:39 and a light chain variable domain VL of SEQ ID NO:40, or
      d) a heavy chain variable domain VH of SEQ ID NO:47 and a light chain variable domain VL of SEQ ID NO:48, or
      e) a heavy chain variable domain VH of SEQ ID NO:55 and a light chain variable domain VL of SEQ ID NO:56;
    and the antibody which binds to human PD-L1 used in the combination therapy is characterized in comprising
      a) a heavy chain variable domain VH of SEQ ID NO:89 and a light chain variable domain VL of SEQ ID NO:92, or
      b) a heavy chain variable domain VH of SEQ ID NO:90 and a light chain variable domain VL of SEQ ID NO:93, or
      c) a heavy chain variable domain VH of SEQ ID NO:90 and a light chain variable domain VL of SEQ ID NO:94, or
      d) a heavy chain variable domain VH of SEQ ID NO:90 and a light chain variable domain VL of SEQ ID NO:95, or
      e) a heavy chain variable domain VH of SEQ ID NO:90 and a light chain variable domain VL of SEQ ID NO:96, or
      f) a heavy chain variable domain VH of SEQ ID NO:90 and a light chain variable domain VL of SEQ ID NO:97, or
      g) a heavy chain variable domain VH of SEQ ID NO:90 and a light chain variable domain VL of SEQ ID NO:98, or
      h) a heavy chain variable domain VH of SEQ ID NO:90 and a light chain variable domain VL of SEQ ID NO:99, or
      i) a heavy chain variable domain VH of SEQ ID NO:90 and a light chain variable domain VL of SEQ ID NO:100, or
      j) a heavy chain variable domain VH of SEQ ID NO:90 and a light chain variable domain VL of SEQ ID NO:101, or
      k) a heavy chain variable domain VH of SEQ ID NO:90 and a light chain variable domain VL of SEQ ID NO:102, or
      l) a heavy chain variable domain VH of SEQ ID NO:90 and a light chain variable domain VL of SEQ ID NO:103, or
      m) a heavy chain variable domain VH of SEQ ID NO:90 and a light chain variable domain VL of SEQ ID NO:104, or
      n) a heavy chain variable domain VH of SEQ ID NO:90 and a light chain variable domain VL of SEQ ID NO:105, or
      o) a heavy chain variable domain VH of SEQ ID NO:90 and a light chain variable domain VL of SEQ ID NO:106, or
      p) a heavy chain variable domain VH of SEQ ID NO:91 and a light chain variable domain VL of SEQ ID NO:107.

The invention further comprised an antibody which binds to human CSF-1R, for use in the treatment of a patient having a CSF-1R expressing tumor or having a tumor with CSF-1R expressing macrophage infiltrate, wherein the tumor is characterized by an increase of CSF-1R ligand and wherein the anti-CSF-1R antibody is administered in combination with an antibody which binds to human PD-L1,
  wherein the antibody which binds to human CSF-1R used in the combination therapy is characterized in comprising
    a) a heavy chain variable domain VH of SEQ ID NO:23 and a light chain variable domain VL of SEQ ID NO:24, or
    b) a heavy chain variable domain VH of SEQ ID NO:31 and a light chain variable domain VL of SEQ ID NO:32, or
    c) a heavy chain variable domain VH of SEQ ID NO:39 and a light chain variable domain V L of SEQ ID NO:40, or d) a heavy chain variable domain VH of SEQ ID NO:47 and a light chain variable domain VL of SEQ ID NO:48, or
e) a heavy chain variable domain VH of SEQ ID NO:55 and a light chain variable domain VL of SEQ ID NO:56;
and the antibody which binds to human PD-L1 used in the combination therapy is characterized in comprising
a) a heavy chain variable domain VH of SEQ ID NO:89 and a light chain variable domain VL of SEQ ID NO:92, or
b) a heavy chain variable domain VH of SEQ ID NO:90 and a light chain variable domain VL of SEQ ID NO:93, or
c) a heavy chain variable domain VH of SEQ ID NO:90 and a light chain variable domain VL of SEQ ID NO:94, or
d) a heavy chain variable domain VH of SEQ ID NO:90 and a light chain variable domain VL of SEQ ID NO:95, or
e) a heavy chain variable domain VH of SEQ ID NO:90 and a light chain variable domain VL of SEQ ID NO:96, or
f) a heavy chain variable domain VH of SEQ ID NO:90 and a light chain variable domain VL of SEQ ID NO:97, or
g) a heavy chain variable domain VH of SEQ ID NO:90 and a light chain variable domain VL of SEQ ID NO:98, or
h) a heavy chain variable domain VH of SEQ ID NO:90 and a light chain variable domain VL of SEQ ID NO:99, or
i) a heavy chain variable domain VH of SEQ ID NO:90 and a light chain variable domain VL of SEQ ID NO:100, or
j) a heavy chain variable domain VH of SEQ ID NO:90 and a light chain variable domain VL of SEQ ID NO:101, or
k) a heavy chain variable domain VH of SEQ ID NO:90 and a light chain variable domain VL of SEQ ID NO:102, or
l) a heavy chain variable domain VH of SEQ ID NO:90 and a light chain variable domain VL of SEQ ID NO:103, or
m) a heavy chain variable domain VH of SEQ ID NO:90 and a light chain variable domain VL of SEQ ID NO:104, or
n) a heavy chain variable domain VH of SEQ ID NO:90 and a light chain variable domain VL of SEQ ID NO:105, or
o) a heavy chain variable domain VH of SEQ ID NO:90 and a light chain variable domain V L of SEQ ID NO:106, or
p) a heavy chain variable domain VH of SEQ ID NO:91 and a light chain variable domain VL of SEQ ID NO:107.

In one embodiment the antibodies are of human IgG1 subclass or human IgG4 subclass.

The invention further comprises:
A) a method for
i) the inhibition of cell proliferation in CSF-1R ligand-dependent and/or CSF-1R ligand-independent CSF-1R expressing tumor cells;
ii) the inhibition of cell proliferation of tumors with CSF-1R ligand-dependent and/or CSF-1R ligand-independent CSF-1R expressing macrophage infiltrate;
iii) the inhibition of cell survival (in CSF-1R ligand-dependent and/or CSF-1R ligand-independent) CSF-1R expressing monocytes and macrophages; and/or
iv) the inhibition of cell differentiation (in CSF-1R ligand-dependent and/or CSF-1R ligand-independent) CSF-1R expressing monocytes into macrophages;
wherein an antibody which binds to human CSF-1R, is administered in combination with an antibody which binds to human PD-L1,
or
B) a method of treatment of a patient having a CSF-1R expressing tumor or having a tumor with CSF-1R expressing macrophage infiltrate, wherein the tumor is characterized by an increase of CSF-1R ligand and wherein an antibody which binds to human CSF-1R is administered in combination with an antibody which binds to human PD-L1,
wherein the antibody which binds to human CSF-1R used in the combination therapy is characterized in comprising
a) a heavy chain variable domain VH of SEQ ID NO:23 and a light chain variable domain V L of SEQ ID NO:24, or
b) a heavy chain variable domain VH of SEQ ID NO:31 and a light chain variable domain VL of SEQ ID NO:32, or
c) a heavy chain variable domain VH of SEQ ID NO:39 and a light chain variable domain VL of SEQ ID NO:40, or
d) a heavy chain variable domain VH of SEQ ID NO:47 and a light chain variable domain VL of SEQ ID NO:48, or
e) a heavy chain variable domain VH of SEQ ID NO:55 and a light chain variable domain VL of SEQ ID NO:56;
and the antibody which binds to human PD-L1 used in the combination therapy is characterized in comprising
a) a heavy chain variable domain VH of SEQ ID NO:89 and a light chain variable domain VL of SEQ ID NO:92, or
b) a heavy chain variable domain VH of SEQ ID NO:90 and a light chain variable domain VL of SEQ ID NO:93, or
c) a heavy chain variable domain VH of SEQ ID NO:90 and a light chain variable domain VL of SEQ ID NO:94, or
d) a heavy chain variable domain VH of SEQ ID NO:90 and a light chain variable domain VL of SEQ ID NO:95, or
e) a heavy chain variable domain VH of SEQ ID NO:90 and a light chain variable domain VL of SEQ ID NO:96, or
f) a heavy chain variable domain VH of SEQ ID NO:90 and a light chain variable domain VL of SEQ ID NO:97, or
g) a heavy chain variable domain VH of SEQ ID NO:90 and a light chain variable domain VL of SEQ ID NO:98, or
h) a heavy chain variable domain VH of SEQ ID NO:90 and a light chain variable domain VL of SEQ ID NO:99, or i) a heavy chain variable domain VH of SEQ ID NO:90 and a light chain variable domain VL of SEQ ID NO:100, or j) a heavy chain variable domain VH of SEQ ID NO:90 and a light chain variable domain VL of SEQ ID NO:101, or k) a heavy chain variable domain VH of SEQ ID NO:90 and a light chain variable domain V L of SEQ ID NO:102, or l) a heavy chain variable domain VH of SEQ ID NO:90 and a light chain variable domain VL of SEQ ID NO:103, or m) a heavy chain variable domain VH of SEQ ID NO:90 and a light chain variable domain VL of SEQ ID NO:104, or n) a heavy chain variable domain VH of SEQ ID NO:90 and a light chain variable domain VL of SEQ ID NO:105, or o) a heavy chain variable domain VH of SEQ ID NO:90 and a light chain variable domain VL of SEQ ID NO:106, or p) a heavy chain variable domain VH of SEQ ID NO:91 and a light chain variable domain VL of SEQ ID NO:107.

The term "ligand independent" as used herein refers to a ligand-independent signaling through the extracellular ECD (and does not include the ligand independent signaling mediated by activating point mutations in the intracellular kinase domain). In one embodiment CSF-1R ligand in this context refers a CSF-1R ligand selected from human CSF-1 (SEQ ID No: 86) and human IL-34 (SEQ ID No: 87); in one embodiment the CSF-1R ligand is human CSF-1 (SEQ ID No: 86); in one embodiment the CSF-1R ligand is human IL-34 (SEQ ID No: 87)).

The invention comprises the combination treatment of a patient having a CSF-1R expressing tumor or having a tumor with CSF-1R expressing macrophage infiltrate, wherein the tumor is characterized by an increase of CSF-1R ligand (in one embodiment the CSF-1R ligand is selected from human CSF-1 (SEQ ID No: 86) and human IL-34 (SEQ ID No: 87); in one embodiment the CSF-1R ligand is human CSF-1 (SEQ ID No: 86); in one embodiment the CSF-1R ligand is human IL-34 (SEQ ID No: 87)) (detectable in scrum, urine or tumor biopsies), wherein an antibody which binds to human CSF-1R as described herein is administered in combination with an anti-PD-L antibody as described herein. The term "increase of CSF-1R ligand" refers to the overexpression of human CSF-1R ligand (in one embodiment the CSF-1R ligand is selected from human CSF-1 (SEQ ID No: 86) and human IL-34 (SEQ ID No: 87); in one embodiment the CSF-1R ligand is human CSF-1 (SEQ ID No: 86); in one embodiment the CSF-1R ligand is human IL-34 (SEQ ID No: 87)) (compared to normal tissue) before treatment or overexpression of human CSF-1R ligand induced by treatment with anti-CSF-1R antibody (and compared to the expression levels before treatment). In certain embodiments, the term "increase" or "above" refers to a level above the reference level or to an overall increase of 5%, 10%, 20%, 25%, 30%, 40%, 50%, 60%, 70%, 80%, 85%, 90%, 95%, 100% or greater, in CSF-1R ligand level detected by the methods described herein, as compared to the CSF-1R ligand level from a reference sample. In certain embodiments, the term increase refers to the increase in CSF-1R ligand level wherein, the increase is at least about 1.5-, 1.75-, 2-, 3-, 4-, 5-, 6-, 7-, 8-, 9-, 10-, 15-, 20-, 25-, 30-, 40-, 50-, 60-, 70-, 75-, 80-, 90-, or 100-fold higher as compared to the CSF-1R ligand level e.g. predetermined from a reference sample. In one preferred embodiment the term increased level relates to a value at or above a reference level.

The combination therapies of the antibodies described herein show benefits for patients in need of a CSF-1R targeting therapy. The specific anti-CSF-1R antibodies according to the invention show efficient antiproliferative activity against ligand-independent and ligand-dependent proliferation and are especially useful inter alia in the treatment of cancer and metastasis in combination with the specific anti-PD-L1 antibodies described herein.

1b: Human Monocytes differentiated into macrophages with GM-CSF (M1) or M-CSF (M2) for 7 days. Phenotype analyzed by indirect fluorescence analysis-staining with anti CD163-PE, anti CD80-PE or anti HLA-DR/DQ/DP-Zenon-Alexa647 labeled. The number in each histogram corresponds to mean ratio fluorescence intensity (MRFI); calculated ratio between mean fluorescence intensity (MFI) of cells stained with the selected antibody (empty histogram) and of corresponding isotype control (negative control; gray filled histogram) (mean SD; n≥5).

FIG. 2a-d CSF-1 levels in Cynomolgus monkey after application of different dosages of anti-CSF-1R antibody hMab 2F11-e7.

FIG. 3 In the presence of TAMs, T cell expansion induced by activation of CD3 and CD28 was suppressed: TAM were isolated from MC38 tumors and co-cultured at the ratios indicated with CFSE-labeled CD8+ T cells in the presence of CD3/CD28 stimulation. T cell proliferation was analyzed after 3 days using bead quantification of CFSElow dividing cells. One representative experiment out of two is depicted as means+SEM of triplicate wells.

Figure 4:
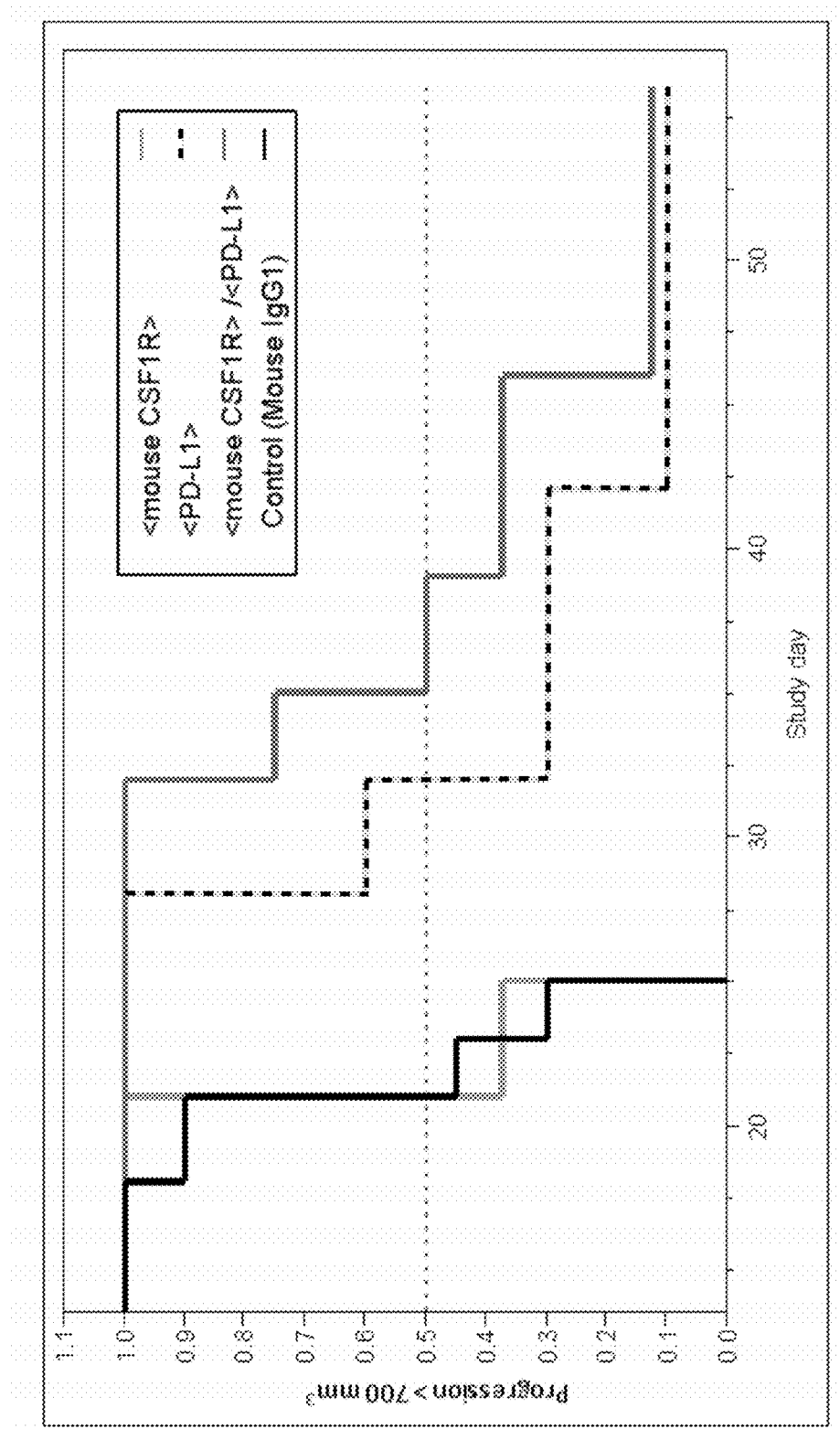

FIG. 4 Anti tumor Efficacy of <mouse CSF1R> antibody/ <PD-L> antibody combination in the MC38 mouse CRC in vivo model (Kaplan-Meier Plot for Progression of tumor volume >700 mm3).

Figure 5:
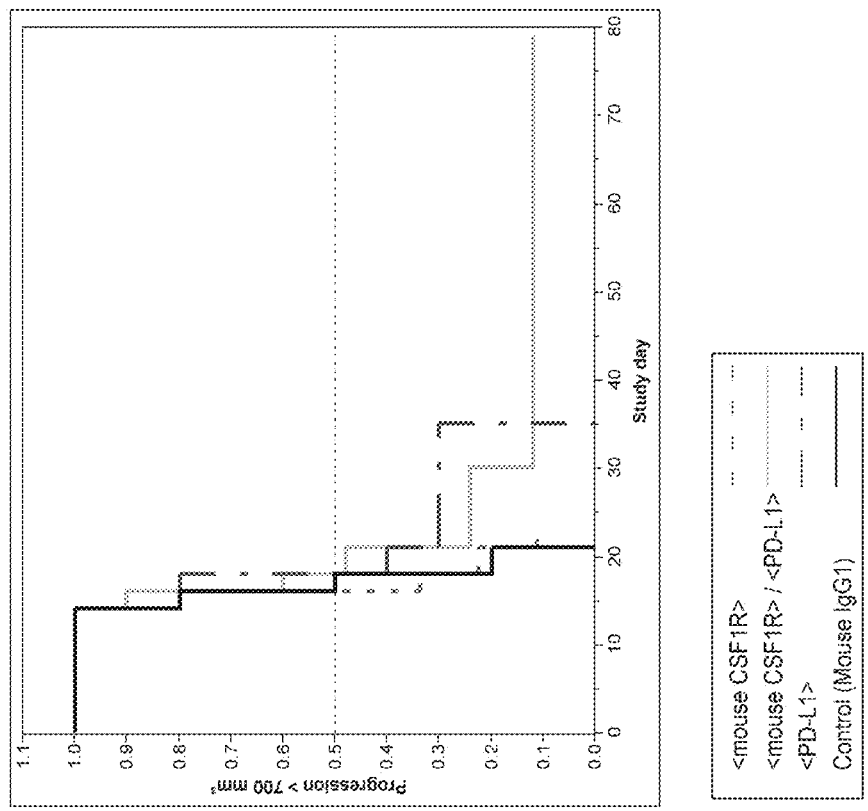

FIG. 5 Anti tumor Efficacy of <mouse CSF1R> antibody/ <PD-L> antibody combination in the subcutaneous syngeneic CT26.WT colon carcinoma in vivo model (Kaplan-Meier Plot for Progression of tumor volume >700 mm3).

DETAILED DESCRIPTION OF THE INVENTION

Many tumors are characterized by a prominent immune cell infiltrate, including macrophages. Initially, the immune cells were thought to be part of a defense mechanism against the tumor, but recent data support the notion that several immune cell populations including macrophages may, in fact, promote tumor progression. Macrophages are characterized by their plasticity. Depending on the cytokine microenvironment, macrophages can exhibit so-called M1 or M2-subtypes. M2 macrophages are engaged in the suppression of tumor immunity. They also play an important role in tissue repair functions such as angiogenesis and tissue remodeling which are coopted by the tumor to support growth. In contrast to tumor promoting M2 macrophages, M1 macrophages exhibit antitumor activity via the secretion of inflammatory cytokines and their engagement in antigen presentation and phagocytosis (Mantovani, A. et al., Curr. Opin. Immunol. 2 (2010) 231-237).

By secreting various cytokines such as colony stimulating factor 1 (CSF-1) and IL-10, tumor cells are able to recruit and shape macrophages into the M2-subtype, whereas cytokines such as granulocyte macrophage colony stimulating factor (GM-CSF), IFN-gamma program macrophages towards the M1 subtype. Using immunohistochemistry, it is possible to distinguish between a macrophage subpopulation co-expressing CD68 and CD163, which is likely to be enriched for M2 Macrophages, and a subset showing the CD68+/MHC II+, or CD68+/CD80+ immunophenotype, likely to include M1 macrophages. Cell shape, size, and spatial distribution of CD68 and CD163 positive macrophages is consistent with published hypotheses on a tumor-promoting role of M2 macrophages, for example by their preferential location in tumor intersecting stroma, and vital tumor areas. In contrast, CD68+/MHC class II+ macrophages are ubiquitously found. Their hypothetical role in phagocytosis is reflected by clusters of the CD68+/MHC class II+, but CD163− immunophenotype near apoptotic cells and necrotic tumor areas.

The subtype and marker expression of different macrophage subpopulations is linked with their functional state. M2 macrophages can support tumorigenesis by:
a) enhancing angiogenesis via the secretion of angiogenic factors such as VEGF or bFGF,
b) supporting metastasis formation via secretion of matrix metalloproteinases (MMPs), growth factors and migratory factors guiding the tumor cells to the blood stream and setting up the metastatic niche (Wyckoff, J. et al., Cancer Res, 67 (2007) 2649-2656),
c) playing a role in building an immunosuppressive milieu by secreting immunosuppressive cytokines such as IL-4, Il-13, IL-1ra and IL-10, which in turn regulate T regulatory cell function. Conversely CD4 positive T cells have been shown to enhance the activity of tumor promoting macrophages in preclinical models (Mantovani, A. et al., Eur. J. Cancer 40 (2004) 1660-1667; DeNardo, D. et al., Cancer Cell 16 (2009) 91-102).

Accordingly, in several types of cancer (e.g. breast, ovarian, Hodgkin's lymphoma) the prevalence of M2 subtype tumor associated macrophages (TAMs) has been associated with poor prognosis (Bingle, L. et al., J. Pathol. 3 (2002) 254-265; Orre, M., and Rogers, P. A., Gynecol. Oncol. 1 (1999) 47-50; Steidl, C. et al., N. Engl. J. Med. 10 (2010) 875-885). Recent data show a correlation of CD63 positive macrophage infiltrate in tumors and tumor grade (Kawamura, K. et al., Pathol. Int. 59 (2009) 300-305). TAMs isolated from patient tumors had a tolerant phenotype and were not cytotoxic to tumor cells (Mantovani, A. et al., Eur. J. Cancer 40 (2004) 1660-1667). However, infiltration of TAMs in the presence of cytotoxic T cells correlates with improved survival in non small cell lung cancer and hence reflects a more prominent M1 macrophage infiltrate in this tumor type (Kawai, O. et al., Cancer 6 (2008) 1387-1395).

Recently, a so-called immune signature comprising high numbers of macrophages and CD4 positive T cells, but low numbers of cytotoxic CD8 positive T cells was shown to correlate with reduced overall survival (OS) in breast cancer patients and to represent an independent prognostic factor (DeNardo, D. et al., Cancer Discovery 1 (2011) 54-67).

Consistent with a role for CSF-1 in driving the pro-tumorigenic function of M2 macrophages, high CSF-1 expression in rare sarcomas or locally aggressive connective tissue tumors, such as pigmented villonodular synovitis (PVNS) and tenosynovial giant cell tumor (TGCT) due in part to a translocation of the CSF-1 gene, leads to the accumulation of monocytes and macrophages expressing the receptor for CSF-1, the colony-stimulating factor 1 receptor (CSF-1R) forming the majority of the tumor mass (West, R. B. et al., Proc. Natl. Acad. Sci. USA 3 (2006) 690-695). These tumors were subsequently used to define a CSF-1 dependent macrophage signature by gene expression profiling. In breast cancer and leiomyosarcoma patient tumors this CSF-1 response gene signature predicts poor prognosis (Espinosa, I. et al., Am. J. Pathol. 6 (2009) 2347-2356; Beck, A. et al., Clin. Cancer Res. 3 (2009) 778-787).

CSF-1R belongs to the class III subfamily of receptor tyrosine kinases and is encoded by the c-fms proto-oncogene. Binding of CSF-1 or IL-34 induces receptor dimerization, followed by autophosphorylation and activation of downstream signaling cascades. Activation of CSF-1R regulates the survival, proliferation and differentiation of monocytes and macrophages (Xiong, Y. et al., J. Biol. Chem. 286 (2011) 952-960).

In addition to cells of the monocytic lineage and osteoclasts, which derive from the same hematopoietic precursor as the macrophage, CSF-1R/c-fms has also been found to be expressed by several human epithelial cancers such as ovarian and breast cancer and in leiomyosarcoma and TGCT/PVNS, albeit at lower expression levels compared to macrophages. As with TGCT/PVNS, elevated levels of CSF-1, the ligand for CSF-1R, in serum as well as ascites of ovarian cancer patients have been correlated with poor prognosis (Scholl, S. et al., Br. J. Cancer 62 (1994) 342-346; Price, F. et al., Am. J. Obstet. Gynecol. 168 (1993) 520-527). Furthermore, a constitutively active mutant form of CSF 1R is able to transform NIH3T3 cells, one of the properties of an oncogene (Chambers, S., Future Oncol 5 (2009) 1429-1440).

Preclinical models provide validation of CSF-1R as an oncology target. Blockade of CSF-1 as well as CSF-1R activity results in reduced recruitment of TAMs. Chemotherapy resulted in elevated CSF-1 expression in tumor cells leading to enhanced TAM recruitment. Blockade of CSF-1R in combination with paclitaxel resulted in activation of CD8 positive cytotoxic T cells leading to reduced tumor growth and metastatic burden in a spontaneous transgenic breast cancer model (DeNardo, D. et al., Cancer Discovery 1 (2011) 54-67).

The human CSF-1R (CSF-1 receptor; synonyms: M-CSF receptor; Macrophage colony-stimulating factor 1 receptor, Fms proto-oncogene, c-fms, SEQ ID NO: 22)) is known since 1986 (Coussens, L., et al., Nature 320 (1986) 277-280). CSF-1R is a growth factor and encoded by the c-fms proto-oncogene (reviewed e.g. in Roth, P. and Stanley, E. R., Curr. Top. Microbiol. Immunol. 181 (1992) 141-167).

CSF-1R is the receptor for the CSF-1R ligands CSF-1 (macrophage colony stimulating factor, also called M-CSF) (SEQ ID No.: 86) and IL-34 (SEQ ID No.: 87) and mediates the biological effects of these cytokines (Sherr, C. J., et al., Cell 41 (1985) 665-676; Lin, H., et al., Science 320 (2008) 807-811). The cloning of the colony stimulating factor-1 receptor (also called c-fms) was described for the first time in Roussel, M. F., et al., Nature 325 (1987) 549-552. In that publication, it was shown that CSF-1R had transforming potential dependent on changes in the C-terminal tail of the protein including the loss of the inhibitory tyrosine 969 phosphorylation which binds Cbl and thereby regulates receptor down regulation (Lee, P. S., et al., Embo J. 18 (1999) 3616-3628).

CSF-1R is a single chain, transmembrane receptor tyrosine kinase (RTK) and a member of the family of immunoglobulin (Ig) motif containing RTKs characterized by 5 repeated Ig-like subdomains D1-D5 in the extracellular domain (ECD) of the receptor (Wang, Z., et al Molecular and Cellular Biology 13 (1993) 5348-5359). The human CSF-1R Extracellular Domain (CSF-1R-ECD) (SEQ ID NO: 64) comprises all five extracellular Ig-like subdomains D1-D5. The human CSF-1R fragment delD4 (SEQ ID NO: 65) comprises the extracellular Ig-like subdomains D1-D3 and D5, but is missing the D4 subdomain. The human CSF-1R fragment D1-D3 (SEQ ID NO: 66) comprises the respective subdomains D1-D3. The sequences are listed without the signal peptide MGSGPGVLLL LLVATAWHGQ G (SEQ ID NO: 67). The human CSF-1R fragment D4-D3 (SEQ ID NO: 85) comprises the respective subdomains D4-D3.

Currently two CSF-1R ligands that bind to the extracellular domain of CSF-1R are known. The first one is CSF-1 (colony stimulating factor 1, also called M-CSF, macrophage; human CSF-1, SEQ ID NO: 86) and is found extracellularly as a disulfide-linked homodimer (Stanley, E. R. et al., Journal of Cellular Biochemistry 21 (1983) 151-159; Stanley, E. R. et al., Stem Cells 12 Suppl. 1 (1995) 15-24). The second one is IL-34 (human IL-34; SEQ ID NO: 87) (Hume, D. A., et al, Blood 119 (2012) 1810-1820). Thus in one embodiment the term "CSF-1R ligand" refers to human CSF-1 (SEQ ID NO: 86) and/or human IL-34 (SEQ ID NO: 87).

For experiments often the active 149 amino acid (aa) fragment of human CSF-1 (aa 33-181 of SEQ ID NO: 86) is used. This active 149 aa fragment of human CSF-1 (aa 33-181 of SEQ ID NO: 86) is contained in all 3 major forms of CSF-1 and is sufficient to mediate binding to CSF-1R (Hume, D. A., et al, Blood 119 (2012) 1810-1820).

The main biological effects of CSF-1R signaling are the differentiation, proliferation, migration, and survival of hematopoietic precursor cells to the macrophage lineage (including osteoclast). Activation of CSF-1R is mediated by its CSF-1R ligands, CSF-1 (M-CSF) and IL-34. Binding of CSF-1 (M-CSF) to CSF-1R induces the formation of homodimers and activation of the kinase by tyrosine phosphorylation (Li, W. et al, EMBO Journal. 10 (1991) 277-288; Stanley, E. R., et al., Mol. Reprod. Dev. 46 (1997) 4-10).

The intracellular protein tyrosine kinase domain is interrupted by a unique insert domain that is also present in the other related RTK class III family members that include the platelet derived growth factor receptors (PDGFR), stem cell growth factor receptor (c-Kit) and fins-like cytokine receptor (FLT3). In spite of the structural homology among this family of growth factor receptors, they have distinct tissue-specific functions.

CSF-1R is mainly expressed on cells of the monocytic lineage and in the female reproductive tract and placenta. In addition expression of CSF-1R has been reported in Langerhans cells in skin, a subset of smooth muscle cells (Inaba, T., et al., J. Biol. Chem. 267 (1992) 5693-5699), B cells (Baker, A. H., et al., Oncogene 8 (1993) 371-378) and microglia (Sawada, M., et al., Brain Res. 509 (1990) 119-124). Cells with mutant human CSF-1R ((SEQ ID NO: 23) are known to proliferate independently of ligand stimulation.

As used herein, "binding to human CSF-1R" or "specifically binding to human CSF-1R" or "which binds to human CSF-1R" or "anti-CSF-1R antibody" refers to an antibody specifically binding to the human CSF-1R antigen with a binding affinity of KD-value of $1.0 \times 10^{-8}$ mol/l or lower, in one embodiment of a KD-value of $1.0 \times 10^{-9}$ mol/l or lower. The binding affinity is determined with a standard binding assay, such as surface plasmon resonance technique (BAcore®, GE-Healthcare Uppsala, Sweden). Thus an "antibody binding to human CSF-1R" as used herein refers to an antibody specifically binding to the human CSF-1R antigen with a binding affinity of KD $1.0 \times 10^{-8}$ mol/1 or lower (in one embodiment $1.0 \times 10^{-8}$ mol/l-$1.0 \times 10^{-13}$ mol/l), in on embodiment of a KD $1.0 \times 10^{-9}$ mol/l or lower (in one embodiment $1.0 \times 10^{-9}$ mol/l-$1.0 \times 10^{-13}$ mol/l).

Pd-1/Pd-L1/Pd-L2 Pathway:

An important negative co-stimulatory signal regulating T cell activation is provided by programmed death—1 receptor (PD-1)(CD279), and its ligand binding partners PD-L1 (B7-H1, CD274; SEQ ID NO: 88) and PD-L2 (B7-DC, CD273). The negative regulatory role of PD-1 was revealed by PD-1 knock outs (Pdcdl-/-), which are prone to autoimmunity. Nishimura et al., Immunity 11: 141-51 (1999); Nishimura et al., Science 291: 319-22 (2001). PD-1 is related to CD28 and CTLA-4, but lacks the membrane proximal cysteine that allows homodimerization. The cytoplasmic domain of PD-1 contains an immunoreceptor tyrosine-based inhibition motif (ITIM, V/IxYxxL/V). PD-1 only binds to PD-L1 and PD-L2. Freeman et al., J. Exp. Med. 192: 1-9 (2000); Dong et al., Nature Med. 5: 1365-1369 (1999); Latchman et al., Nature Immunol. 2: 261-268 (2001); Tseng t al., J. Exp. Med. 193: 839-846 (2001).

PD-1 can be expressed on T cells, B cells, natural killer T cells, activated monocytes and dendritic cells (DCs). PD-1 is expressed by activated, but not by unstimulated human CD4+ and CD8+ T cells, B cells and myeloid cells. This stands in contrast to the more restricted expression of CD28 and CTLA-4. Nishimura et al., Int. Immunol. 8: 773-80 (1996); Boettler et al., J. Virol. 80: 3532-40 (2006). There are at least 4 variants of PD-1 that have been cloned from activated human T cells, including transcripts lacking (i) exon 2, (ii) exon 3, (iii) exons 2 and 3 or (iv) exons 2 through 4. Nielsen et al., Cell. Immunol. 235: 109-16 (2005). With the exception of PD-1 Δex3, all variants are expressed at similar levels as full length PD-1 in resting peripheral blood mononuclear cells (PBMCs). Expression of all variants is significantly induced upon activation of human T cells with anti-CD3 and anti-CD28. The PD-1 Δex3 variants lacks a transmembrane domain, and resembles soluble CTLA-4, which plays an important role in autoimmunity. Ueda et al., Nature 423: 506-11 (2003). This variant is enriched in the synovial fluid and sera of patients with rheumatoid arthritis. Wan et al., J. Immunol. 177: 8844-50 (2006).

The two PD-1 ligands differ in their expression patterns. PD-L1 is constitutively expressed on mouse T and B cells, CDs, macrophages, mesenchymal stem cells and bone marrow-derived mast cells. Yamazaki et al., J. Immunol. 169: 5538-45 (2002). PD-L1 is expressed on a wide range of nonhematopoictic cells (e.g., cornea, lung, vascular epithelium, liver nonparenchymal cells, mesenchymal stem cells, pancreatic islets, placental synctiotrophoblasts, keratinocytes, etc.) [Keir et al., Annu. Rev. Immunol. 26: 677-704 (2008)], and is upregulated on a number of cell types after activation. Both type I and type II interferons IFN's) upregulate PD-L1. Eppihimer et al., Microcirculation 9: 133-45 (2002); Schreiner et al., J. Neuroimmunol. 155: 172-82 (2004). PD-L1 expression in cell lines is decreased when MyD88, TRAF6 and MEK are inhibited. Liu et al., Blood 110: 296-304 (2007). JAK2 has also been implicated in PD-L1 induction. Lee et al., FEBS Lett. 580: 755-62 (2006);

Liu et al., Blood 110: 296-304 (2007). Loss or inhibition of phosphatase and tensin homolog (PTEN), a cellular phosphatase that modified phosphatidylinositol 3-kinase (PI3K) and Akt signaling, increased post-transcriptional PD-L1 expression in cancers. Parsa et al., Nat. Med. 13: 84-88 (2007).

PD-L2 expression is more restricted than PD-L1. PD-L2 is inducibly expressed on DCs, macrophages, and bone marrow-derived mast cells. PD-L2 is also expressed on about half to two-thirds of resting peritoneal B1 cells, but not on conventional B2 B cells. Zhong et al., Eur. J. Immunol. 37: 2405-10 (2007). PD-L2+B1 cells bind phosphatidylcholine and may be important for innate immune responses against bacterial antigens. Induction of PD-L2 by IFN-gamma is partially dependent upon NF-κB. Liang et al., Eur. J. Immunol. 33: 2706-16 (2003). PD-L2 can also be induced on monocytes and macrophages by GM-CF, IL-4 and IFN-gamma. Yamazaki t al., J. Immunol. 169: 5538-45 (2002); Loke et al., PNAS 100:5336-41 (2003).

PD-1 signaling typically has a greater effect on cytokine production than on cellular proliferation, with significant effects on IFN-gamma, TNF-alpha and IL-2 production. PD-1 mediated inhibitory signaling also depends on the strength of the TCR signaling, with greater inhibition delivered at low levels of TCR stimulation. This reduction can be overcome by costimulation through CD28 [Freeman et al., J. Exp. Med. 192: 1027-34 (2000)] or the presence of IL-2 [Carter et al., Eur. J. Immunol. 32: 634-43 (2002)].

Evidence is mounting that signaling through PD-L1 and PD-L2 may be bidirectional. That is, in addition to modifying TCR or BCR signaling, signaling may also be delivered back to the cells expressing PD-L1 and PD-L2. While treatment of dendritic cells with a naturally human anti-PD-L2 antibody isolated from a patient with Waldenstrom's macroglobulinemia was not found to upregulate MHC II or B7 costimulatory molecules, such cells did produce greater amount of proinflammatory cytokines, particularly TNF-alpha and IL-6, and stimulated T cell proliferation. Nguyen et al., J. Exp. Med. 196: 1393-98 (2002). Treatment of mice with this antibody also (1) enhanced resistance to transplanted b16 melanoma and rapidly induced tumor-specific CTL. Radhakrishnan et al., J. Immunol. 170: 1830-38 (2003); Radhakrishnan et al., Cancer Res. 64: 4965-72 (2004); Heckman et al., Eur. J. Immunol. 37: 1827-35 (2007); (2) blocked development of airway inflammatory disease in a mouse model of allergic asthma. Radhakrishnan et al., J. Immunol. 173: 1360-65 (2004); Radhakrishnan et al., J. Allergy Clin. Immunol. 116: 668-74 (2005).

Further evidence of reverse signaling into dendritic cells ("DC's") results from studies of bone marrow derived DC's cultured with soluble PD-1 (PD-1 EC domain fused to Ig constant region—"s-PD-1"). Kuipers et al., Eur. J. Immunol. 36: 2472-82 (2006). This sPD-1 inhibited DC activation and increased IL-10 production, in a manner reversible through administration of anti-PD-1.

Additionally, several studies show a receptor for PD-L1 or PD-L2 that is independent of PD-1. B7.1 has already been identified as a binding partner for PD-L1. Butte et al., Immunity 27: 111-22 (2007). Chemical crosslinking studies suggest that PD-L1 and B7.1 can interact through their IgV-like domains. B7.1:PD-L1 interactions can induce an inhibitory signal into T cells. Ligation of PD-L1 on CD4+ T cells by B7.1 or ligation of B7.1 on CD4+ T cells by PD-L delivers an inhibitory signal. T cells lacking CD28 and CTLA-4 show decreased proliferation and cytokine production when stimulated by anti-CD3 plus B7.1 coated beads. In T cells lacking all the receptors for B7.1 (i.e., CD28, CTLA-4 and PD-L1), T cell proliferation and cytokine production were no longer inhibited by anti-CD3 plus B7.1 coated beads. This indicates that B7.1 acts specifically through PD-L1 on the T-cell in the absence of CD28 and CTLA-4. Similarly, T cells lacking PD-1 showed decreased proliferation and cytokine production when stimulated in the presence of anti-CD3 plus PD-L1 coated beads, demonstrating the inhibitory effect of PD-L1 ligation on B7.1 on T cells. When T cells lacking all known receptors for PD-L1 (i.e., no PD-1 and B7.1), T cell proliferation was no longer impaired by anti-CD3 plus PD-L1 coated beads. Thus, PD-L1 can exert an inhibitory effect on T cells either through B7.1 or PD-1.

The direct interaction between B7.1 and PD-L1 suggests that the current understanding of costimulation is incomplete, and underscores the significance to the expression of these molecules on T cells. Studies of PD-L1-/- T cells indicate that PD-L1 on T cells can downregulate T cell cytokine production. Latchman et al., Proc. Natl. Acad. Sci. USA 101: 10691-96 (2004). Because both PD-L1 and B7.1 are expressed on T cells, B cells, DCs and macrophages, there is the potential for directional interactions between B7.1 and PD-L1 on these cells types. Additionally, PD-1 on non-hematopoitic cells may interact with B7.1 as well as PD-1 on T cells, raising the question of whether PD-L1 is involved in their regulation. One possible explanation for the inhibitory effect of B7.1:PD-L1 interaction is that T cell PD-L1 may trap or segregate away APC B7.1 from interaction with CD28.

As a result, the antagonism of signaling through PD-L, including blocking PD-L1 from interacting with either PD-1, B7.1 or both, thereby preventing PD-L1 from sending a negative co-stimulatory signal to T-cells and other antigen presenting cells is likely to enhance immunity in response to infection (e.g., acute and chronic) and tumor immunity. In addition, the anti-PD-L1 antibodies of the present invention, may be combined with antagonists of other components of PD-1:PD-L1 signaling, for example, antagonist anti-PD-1 and anti-PD-L2 antibodies.

The term "human PD-L" refers to the human protein PD-L1 (SEQ ID NO: 88, PD-1 signaling typically). As used herein, "binding to human PD-L1" or "specifically binding to human PD-L1" or "which binds to human PD-L1" or "anti-PD-L1 antibody" refers to an antibody specifically binding to the human PD-L1 antigen with a binding affinity of KD-value of $1.0 \times 10^{-8}$ mol/l or lower, in one embodiment of a KD-value of $1.0 \times 10^{-9}$ mol/l or lower. The binding affinity is determined with a standard binding assay, such as surface plasmon resonance technique (BIAcore®, GE-Healthcare Uppsala, Sweden). Thus an "antibody binding to human PD-L1" as used herein refers to an antibody specifically binding to the human PD-L1 antigen with a binding affinity of KD $1.0 \times 10^{-8}$ mol/1 or lower (in one embodiment $1.0 \times 10^{-8}$ mol/l-$1.0 \times 10^{-13}$ mol/l), in on embodiment of a KD $1.0 \times 10^{-9}$ mol/l or lower (in one embodiment $1.0 \times 10^{-9}$ mol/1-$1.0 \times 10^{-13}$ mol/l).

In one embodiment the antibody which binds to human CSF-1R used in the combination therapy described herein is selected from the group consisting of hMab 2F11-c11, hMab 2F11-d8, hMab 2F11-c7, hMab 2F11-f12, and hMab 2F11-g1.

These antibodies are described in WO2011/070024 and are characterized in comprising the following VH and VL sequences as described herein:

TABLE 1

| anti-CSF-1R antibody | amino acid sequence of the heavy chain variable domain VH, SEQ ID NO: | amino acid sequence of the light chain variable domain VL, SEQ ID NO: |
|---|---|---|
| hMab 2F11-c11 | 23 | 24 |
| hMab 2F11-d8 | 31 | 32 |
| hMab 2F11-e7 | 39 | 40 |
| hMab 2F11-f12 | 47 | 48 |
| hMab 2F11-g1 | 55 | 56 |

In one embodiment the antibody which binds to human PD-L1 used in the combination therapy described herein is selected from the group consisting of: 243.55.S70, 243.55.H1, 243.55.H12, 243.55.H37, 243.55.H70, 243.55.H89, 243.55.S1, 243.55.5, 243.55.8, 243.55.30, 243.55.34, 243.55.S37, 243.55.49, 243.55.51, 243.55.62, and 243.55.84.

These antibodies are described in WO 2010/77634 (sequences are shown in FIG. 11 of WO 2010/77634) and are characterized in comprising the following VH and VL sequences as described herein:

TABLE 2

| anti-PD-LI antibody | amino acid sequence of the heavy chain variable domain VH, SEQ ID NO: | amino acid sequence of the light chain variable domain VL, SEQ ID NO: |
|---|---|---|
| 243.55.S70 | 89 | 92 |
| 243.55.H1 | 90 | 93 |
| 243.55.H12 | 90 | 94 |
| 243.55.H37 | 90 | 95 |
| 243.55.H70 | 90 | 96 |
| 243.55.H89 | 90 | 97 |
| 243.55.S1 | 90 | 98 |
| 243.55.5 | 90 | 99 |
| 243.55.8 | 90 | 100 |
| 243.55.30 | 90 | 101 |
| 243.55.34 | 90 | 102 |
| 243.55.S37 | 90 | 103 |
| 243.55.49 | 90 | 104 |
| 243.55.51 | 90 | 105 |
| 243.55.62 | 90 | 106 |
| 243.55.84 | 91 | 107 |

In one embodiment of the invention the antibody which binds to human CSF-1R used in the combination therapy described herein is characterized in comprising
a) a heavy chain variable domain VH of SEQ ID NO:23 and a light chain variable domain VL of SEQ ID NO:24, or
b) a heavy chain variable domain VH of SEQ ID NO:31 and a light chain variable domain VL of SEQ ID NO:32, or
c) a heavy chain variable domain VH of SEQ ID NO:39 and a light chain variable domain VL of SEQ ID NO:40, or
d) a heavy chain variable domain VH of SEQ ID NO:47 and a light chain variable domain VL of SEQ ID NO:48, or
e) a heavy chain variable domain VH of SEQ ID NO:55 and a light chain variable domain VL of SEQ ID NO:56; and
the antibody which binds to human PD-L1 used in the combination therapy is characterized in comprising
a) a heavy chain variable domain VH of SEQ ID NO:89 and a light chain variable domain VL of SEQ ID NO:92, or
b) a heavy chain variable domain VH of SEQ ID NO:90 and a light chain variable domain VL of SEQ ID NO:93, or
c) a heavy chain variable domain VH of SEQ ID NO:90 and a light chain variable domain VL of SEQ ID NO:94, or
d) a heavy chain variable domain VH of SEQ ID NO:90 and a light chain variable domain VL of SEQ ID NO:95, or
e) a heavy chain variable domain VH of SEQ ID NO:90 and a light chain variable domain VL of SEQ ID NO:96, or
f) a heavy chain variable domain VH of SEQ ID NO:90 and a light chain variable domain VL of SEQ ID NO:97, or
g) a heavy chain variable domain VH of SEQ ID NO:90 and a light chain variable domain VL of SEQ ID NO:98, or
h) a heavy chain variable domain VH of SEQ ID NO:90 and a light chain variable domain VL of SEQ ID NO:99, or
i) a heavy chain variable domain VH of SEQ ID NO:90 and a light chain variable domain VL of SEQ ID NO:100, or
j) a heavy chain variable domain VH of SEQ ID NO:90 and a light chain variable domain VL of SEQ ID NO:101, or
k) a heavy chain variable domain VH of SEQ ID NO:90 and a light chain variable domain VL of SEQ ID NO:102, or
l) a heavy chain variable domain VH of SEQ ID NO:90 and a light chain variable domain VL of SEQ ID NO:103, or
m) a heavy chain variable domain VH of SEQ ID NO:90 and a light chain variable domain VL of SEQ ID NO:104, or
n) a heavy chain variable domain VH of SEQ ID NO:90 and a light chain variable domain VL of SEQ ID NO:105, or
o) a heavy chain variable domain VH of SEQ ID NO:90 and a light chain variable domain VL of SEQ ID NO:106, or
p) a heavy chain variable domain VH of SEQ ID NO:91 and a light chain variable domain VL of SEQ ID NO:107.

In one embodiment the antibody which binds to human CSF-1R used in the combination therapy is characterized in comprising
a heavy chain variable domain VH of SEQ ID NO:23 and a light chain variable domain VL of SEQ ID NO:24.

In one embodiment the antibody which binds to human CSF-1R used in the combination therapy is characterized in comprising
a heavy chain variable domain VH of SEQ ID NO:31 and a light chain variable domain VL of SEQ ID NO:32.

In one embodiment the antibody which binds to human CSF-1R used in the combination therapy is characterized in comprising
a heavy chain variable domain VH of SEQ ID NO:39 and a light chain variable domain VL of SEQ ID NO:40.

In one embodiment the antibody which binds to human CSF-1R used in the combination therapy is characterized in comprising
a heavy chain variable domain VH of SEQ ID NO:47 and a light chain variable domain VL of SEQ ID NO:48.

In one embodiment the antibody which binds to human PD-L1 used in the combination therapy is characterized in comprising
a heavy chain variable domain VH of SEQ ID NO:89 and a light chain variable domain VL of SEQ ID NO:92.

In one embodiment the antibody which binds to human PD1-L1 used in the combination therapy is characterized in comprising
a heavy chain variable domain VH of SEQ ID NO:90 and a light chain variable domain VL of SEQ ID NO:93.

In one embodiment the antibody which binds to human PD-L1 used in the combination therapy is characterized in comprising
a heavy chain variable domain VH of SEQ ID NO:90 and a light chain variable domain VL of SEQ ID NO:94.

In one embodiment the antibody which binds to human PD-L1 used in the combination therapy is characterized in comprising
a heavy chain variable domain VH of SEQ ID NO:90 and a light chain variable domain VL of SEQ ID NO:95.

In one embodiment the antibody which binds to human PD-L1 used in the combination therapy is characterized in comprising
a heavy chain variable domain VH of SEQ ID NO:90 and a light chain variable domain VL of SEQ ID NO:96.

In one embodiment the antibody which binds to human PD-L1 used in the combination therapy is characterized in comprising
a heavy chain variable domain VH of SEQ ID NO:90 and a light chain variable domain VL of SEQ ID NO:97.

In one embodiment the antibody which binds to human PD-L1 used in the combination therapy is characterized in comprising
a heavy chain variable domain VH of SEQ ID NO:90 and a light chain variable domain VL of SEQ ID NO:98.

In one embodiment the antibody which binds to human PD-L1 used in the combination therapy is characterized in comprising
a heavy chain variable domain VH of SEQ ID NO:90 and a light chain variable domain VL of SEQ ID NO:99.

In one embodiment the antibody which binds to human PD-L1 used in the combination therapy is characterized in comprising
a heavy chain variable domain VH of SEQ ID NO:90 and a light chain variable domain VL of SEQ ID NO:100.

In one embodiment the antibody which binds to human PD-L1 used in the combination therapy is characterized in comprising
a heavy chain variable domain VH of SEQ ID NO:90 and a light chain variable domain VL of SEQ ID NO:101.

In one embodiment the antibody which binds to human PD-L1 used in the combination therapy is characterized in comprising
a heavy chain variable domain VH of SEQ ID NO:90 and a light chain variable domain VL of SEQ ID NO:102.

In one embodiment the antibody which binds to human PD-L1 used in the combination therapy is characterized in comprising
a heavy chain variable domain VH of SEQ ID NO:90 and a light chain variable domain VL of SEQ ID NO:103.

In one embodiment the antibody which binds to human PD-L1 used in the combination therapy is characterized in comprising
a heavy chain variable domain VH of SEQ ID NO:90 and a light chain variable domain VL of SEQ ID NO:104.

In one embodiment the antibody which binds to human PD-L1 used in the combination therapy is characterized in comprising
a heavy chain variable domain VH of SEQ ID NO:90 and a light chain variable domain VL of SEQ ID NO:105.

In one embodiment the antibody which binds to human PD-L1 used in the combination therapy is characterized in comprising
a heavy chain variable domain VH of SEQ ID NO:90 and a light chain variable domain VL of SEQ ID NO:106.

In one embodiment the antibody which binds to human PD-L1 used in the combination therapy is characterized in comprising
a heavy chain variable domain VH of SEQ ID NO:91 and a light chain variable domain VL of SEQ ID NO:107.

In one preferred embodiment of the invention the antibody which binds to human CSF-1R used in the combination therapy described herein is characterized in comprising
a heavy chain variable domain VH of SEQ ID NO:39 and a light chain variable domain VL of SEQ ID NO:40, and
the antibody which binds to human PD-L1 used in the combination therapy is characterized in comprising
a heavy chain variable domain VH of SEQ ID NO:89 and a light chain variable domain VL of SEQ ID NO:92.

The term "epitope" denotes a protein determinant of human CSF-1R or PD-L1 capable of specifically binding to an antibody. Epitopes usually consist of chemically active surface groupings of molecules such as amino acids or sugar side chains and usually epitopes have specific three dimensional structural characteristics, as well as specific charge characteristics. Conformational and nonconformational epitopes are distinguished in that the binding to the former but not the latter is lost in the presence of denaturing solvents.

The "variable domain" (light chain variable domain VL, heavy chain variable domain VH) as used herein denotes each of the pair of light and heavy chain domains which are involved directly in binding the antibody to the antigen. The variable light and heavy chain domains have the same general structure and each domain comprises four framework (FR) regions whose sequences are widely conserved, connected by three "hypervariable regions" (or complementary determining regions, CDRs). The framework regions adopt a beta-sheet conformation and the CDRs may form loops connecting the beta-sheet structure. The CDRs in each chain are held in their three-dimensional structure by the framework regions and form together with the CDRs from the other chain the antigen binding site. The antibody's heavy and light chain CDR3 regions play a particularly important role in the binding specificity/affinity of the antibodies according to the invention and therefore provide a further object of the invention.

The term "antigen-binding portion of an antibody" when used herein refer to the amino acid residues of an antibody which are responsible for antigen-binding. The antigen-binding portion of an antibody comprises amino acid residues from the "complementary determining regions" or "CDRs". "Framework" or "FR" regions are those variable domain regions other than the hypervariable region residues as herein defined. Therefore, the light and heavy chain variable domains of an antibody comprise from N- to C-terminus the domains FR1, CDR1, FR2, CDR2, FR3, CDR3, and FR4. Especially, CDR3 of the heavy chain is the region which contributes most to antigen binding and defines the antibody's properties. CDR and FR regions are determined according to the standard definition of Kabat et al., Sequences of Proteins of Immunological Interest, 5th ed., Public Health Service, National Institutes of Health, Bethesda, Md. (1991) and/or those residues from a "hypervariable loop".

The terms "nucleic acid" or "nucleic acid molecule", as used herein, are intended to include DNA molecules and RNA molecules. A nucleic acid molecule may be single-stranded or double-stranded, but preferably is double-stranded DNA.

The term "amino acid" as used within this application denotes the group of naturally occurring carboxy alpha-amino acids comprising alanine (three letter code: ala, one letter code: A), arginine (arg, R), asparagine (asn, N), aspartic acid (asp, D), cysteine (cys, C), glutamine (gln, Q), glutamic acid (glu, E), glycine (gly, G), histidine (his, H), isoleucine (ile, I), leucine (leu, L), lysine (lys, K), methionine (met, M), phenylalanine (phe, F), proline (pro, P), serine (ser, S), thronine (thr, T), tryptophan (trp, W), tyrosine (tyr, Y), and valine (val, V).

The "Fc part" of an antibody is not involved directly in binding of an antibody to an antigen, but exhibit various effector functions. A "Fc part of an antibody" is a term well known to the skilled artisan and defined on the basis of papain cleavage of antibodies. Depending on the amino acid sequence of the constant region of their heavy chains, antibodies or immunoglobulins are divided in the classes: IgA, IgD, IgE, IgG and IgM, and several of these may be further divided into subclasses (isotypes), e.g. IgG1, IgG2, IgG3, and IgG4, IgA1, and IgA2. According to the heavy chain constant regions the different classes of immunoglobulins are called α, δ, ε, γ and μ, respectively. The Fc part of an antibody is directly involved in ADCC (antibody-dependent cell-mediated cytotoxicity) and CDC (complement-dependent cytotoxicity) based on complement activation, C1q binding and Fc receptor binding. Complement activation (CDC) is initiated by binding of complement factor C1q to the Fc part of most IgG antibody subclasses. While the influence of an antibody on the complement system is dependent on certain conditions, binding to C1q is caused by defined binding sites in the Fc part. Such binding sites are known in the state of the art and described e.g. by Boackle, R. J., et al., Nature 282 (1979) 742-743; Lukas, T. J., et al., J. Immunol. 127 (1981) 2555-2560; Brunhouse, R., and Cebra, J. J., Mol. Immunol. 16 (1979) 907-917; Burton, D. R., et al., Nature 288 (1980) 338-344; Thommesen, J. E., et al., Mol. Immunol. 37 (2000) 995-1004; Idusogic, E. E., et al., J. Immunol. 164 (2000) 4178-4184; Hezarch, M., et al., J. Virology 75 (2001) 12161-12168; Morgan, A., et al., Immunology 86 (1995) 319-324; EP 0 307 434. Such binding sites are e.g. L234, L235, D270, N297, E318, K320, K322, P331 and P329 (numbering according to EU index of Kabat, E. A., see below). Antibodies of subclass IgG1, IgG2 and IgG3 usually show complement activation and C1q and C3 binding, whereas IgG4 do not activate the complement system and do not bind C1q and C3.

In one embodiment the antibody according to the invention comprises an Fc part derived from human origin and preferably all other parts of the human constant regions. As used herein the term "Fc part derived from human origin" denotes a Fc part which is either a Fc part of a human antibody of the subclass IgG1, IgG2, IgG3 or IgG4, preferably a Fc part from human IgG1 subclass, a mutated Fc part from human IgG1 subclass (in one embodiment with a mutation on L234A+L235A), a Fc part from human IgG4 subclass or a mutated Fc part from human IgG4 subclass (in one embodiment with a mutation on S228P). In one preferred embodiment the human heavy chain constant region is SEQ ID NO: 58 (human IgG1 subclass), in another preferred embodiment the human heavy chain constant region is SEQ ID NO: 59 (human IgG1 subclass with mutations L234A and L235A), in another preferred embodiment the human heavy chain constant region is SEQ ID NO: 60 (human IgG4 subclass), and in another preferred embodiment the human heavy chain constant region is SEQ ID NO: 61 (human IgG4 subclass with mutation S228P). In one embodiment said antibodies have reduced or minimal effector function. In one embodiment the minimal effector function results from an effectorless Fc mutation. In one embodiment the effector is Fc mutation is L234A/L235A or L234A/L235A/P329G or N297A or D265A/N297A. In one embodiment the effectorless Fc mutation is selected for each of the antibodies independently of each other from the group comprising (consisting of) L234A/L235A, L234A/L235A/P329G, N297A and D265A/N297A.

In one embodiment the antibodies described herein are of human IgG class (i.e. of IgG1, IgG2, IgG3 or IgG4 subclass).

In a preferred embodiment the antibodies described herein are of human IgG1 subclass or of human IgG4 subclass. In one embodiment the described herein are of human IgG1 subclass. In one embodiment the antibodies described herein are of human IgG4 subclass.

In one embodiment the antibody described herein is characterized in that the constant chains are of human origin. Such constant chains are well known in the state of the art and e.g. described by Kabat, E. A., (see e.g. Johnson, G. and Wu, T. T., Nucleic Acids Res. 28 (2000) 214-218). For example, a useful human heavy chain constant region comprises an amino acid sequence of SEQ ID NO: 58. For example, a useful human light chain constant region comprises an amino acid sequence of a kappa-light chain constant region of SEQ ID NO: 57.

The invention comprises a method for the treatment of a patient in need of therapy, characterized by administering to the patient a therapeutically effective amount of an antibody according to the invention.

The invention comprises the use of an antibody according to the invention for the described therapy.

One preferred embodiment of the invention are the CSF-1R antibodies of the present invention for use in the treatment of "CSF-1R mediated diseases" or the CSF-1R antibodies of the present invention for use for the manufacture of a medicament in the treatment of "CSF-1R mediated diseases", which can be described as follows:

There are 3 distinct mechanisms by which CSF-1R signaling is likely involved in tumor growth and metastasis. The first is that expression of CSF-ligand and receptor has been found in tumor cells originating in the female reproductive system (breast, ovarian, endometrium, cervical) (Scholl, S. M., et al., J. Natl. Cancer Inst. 86 (1994) 120-126; Kacinski, B. M., Mol. Reprod. Dev. 46 (1997) 71-74; Ngan, H. Y., et al., Eur. J. Cancer 35 (1999) 1546-1550; Kirma, N., et al., Cancer Res 67 (2007) 1918-1926) and the expression has been associated with breast cancer xenograft growth as well as poor prognosis in breast cancer patients. Two point mutations were seen in CSF-1R in about 10-20% of acute myelocytic leukemia, chronic myclocytic leukemia and myelodysplasia patients tested in one study, and one of the mutations was found to disrupt receptor turnover (Ridge, S. A., et al., Proc. Nat. Acad. Sci USA 87 (1990) 1377-1380). However the incidence of the mutations could not be confirmed in later studies (Abu-Duhier, F. M., et al., Br. J. Haematol. 120 (2003) 464-470). Mutations were also found in some cases of hepatocellular cancer (Yang, D. H., et al., Hepatobiliary Pancreat. Dis. Int. 3 (2004) 86-89) and idiopathic myclofibrosis (Abu-Duhier, F. M., et al., Br. J. Haematol. 120 (2003) 464-470). Recently, in the GDM-1 cell line derived from a patient with myclomonoblastic leukemia the Y571D mutation in CSF-1R was identified (Chase, A., et al., Leukemia 23 (2009) 358-364).

Pigmented villonodular synovitis (PVNS) and Tenosynovial Giant cell tumors (TGCT) can occur as a result of a translocation that fuses the M-CSF gene to a collagen gene COL6A3 and results in overexpression of M-CSF (West, R. B., et al., Proc. Natl. Acad. Sci. USA 103 (2006) 690-695). A landscape effect is proposed to be responsible for the resulting tumor mass that consists of monocytic cells attracted by cells that express M-CSF. TGCTs are smaller tumors that can be relatively easily removed from fingers where they mostly occur. PVNS is more aggressive as it can recur in large joints and is not as easily controlled surgically.

The second mechanism is based on blocking signaling through M-CSF/CSF-1R at metastatic sites in bone which induces osteoclastogenesis, bone resorption and ostcolytic bone lesions. Breast, multiple myeloma and lung cancers are examples of cancers that have been found to metastasize to the bone and cause osteolytic bone disease resulting in skeletal complications. M-CSF released by tumor cells and stroma induces the differentiation of hematopoietic myeloid monocyte progenitors to mature osteoclasts in collaboration with the receptor activator of nuclear factor kappa-B ligand-RANKL. During this process, M-CSF acts as a permissive factor by giving the survival signal to osteoclasts (Tanaka, S., et al., J. Clin. Invest. 91 (1993) 257-263). Inhibition of CSF-1R activity during osteoclast differentiation and maturation with an anti-CSF-1R antibody is likely to prevent unbalanced activity of osteoclasts that cause ostcolytic disease and the associated skeletal related events in metastatic disease. Whereas breast, lung cancer and multiple mycloma typically result in ostcolytic lesions, metastasis to the bone in prostate cancer initially has an osteoblastic appearance in which increased bone forming activity results in 'woven bone' which is different from typical lamellar structure of normal bone. During disease progression bone lesions display a significant osteolytic component as well as high serum levels of bone resorption and suggests that anti-resorptive therapy may be useful. Bisphosphonates have been shown to inhibit the formation of osteolytic lesions and reduced the number of skeletal-related events only in men with hormone-refractory metastatic prostate cancer but at this point their effect on osteoblastic lesions is controversial and bisphosphonates have not been beneficial in preventing bone metastasis or hormone responsive prostate cancer to date. The effect of anti-resorptive agents in mixed ostcolytic/osteoblastic prostate cancer is still being studied in the clinic (Chouiri, M. B., et al., Cancer Metastasis Rev. 25 (2006) 601-609; Vessella, R. L. and Corey, E., Clin. Cancer Res. 12 (20 Pt 2) (2006) 6285s-6290s).

The third mechanism is based on the recent observation that tumor associated macrophages (TAM) found in solid tumors of the breast, prostate, ovarian and cervical cancers correlated with poor prognosis (Bingle, L., et al., J. Pathol. 196 (2002) 254-265; Pollard, J. W., Nat. Rev. Cancer 4 (2004) 71-78). Macrophages are recruited to the tumor by M-CSF and other chemokines. The macrophages can then contribute to tumor progression through the secretion of angiogenic factors, proteases and other growth factors and cytokines and may be blocked by inhibition of CSF-1R signaling. Recently it was shown by Zins et al (Zins, K., et al., Cancer Res. 67 (2007) 1038-1045) that expression of siRNA of Tumor necrosis factor alpha (TNF alpha), M-CSF or the combination of both would reduce tumor growth in a mouse xenograft model between 34% and 50% after intra-tumoral injection of the respective siRNA. SiRNA targeting the TNF alpha secreted by the human SW620 cells reduced mouse M-CSF levels and led to reduction of macrophages in the tumor. In addition treatment of MCF7 tumor xenografts with an antigen binding fragment directed against M-CSF did result in 40% tumor growth inhibition, reversed the resistance to chemotherapeutics and improved survival of the mice when given in combination with chemotherapeutics (Paulus, P., et al., Cancer Res. 66 (2006) 4349-4356).

TAMs are only one example of an emerging link between chronic inflammation and cancer. There is additional evidence for a link between inflammation and cancer as many chronic diseases are associated with an increased risk of cancer, cancers arise at sites of chronic inflammation, chemical mediators of inflammation are found in many cancers; deletion of the cellular or chemical mediators of inflammation inhibits development of experimental cancers and long-term use of anti-inflammatory agents reduce the risk of some cancers. A link to cancer exists for a number of inflammatory conditions among-those *H. pylori* induced gastritis for gastric cancer, Schistosomiasis for bladder cancer, HHVX for Kaposi's sarcoma, endometriosis for ovarian cancer and prostatitis for prostate cancer (Balkwill, F., et al., Cancer Cell 7 (2005) 211-217). Macrophages are key cells in chronic inflammation and respond differentially to their microenvironment. There are two types of macrophages that are considered extremes in a continuum of functional states: M1 macrophages are involved in Type 1 reactions. These reactions involve the activation by microbial products and consequent killing of pathogenic microorganisms that result in reactive oxygen intermediates. On the other end of the extreme are M2 macrophages involved in Type 2 reactions that promote cell proliferation, tune inflammation and adaptive immunity and promote tissue remodeling, angiogenesis and repair (Mantovani, A., et al., Trends Immunol. 25 (2004) 677-686). Chronic inflammation resulting in established neoplasia is usually associated with M2 macrophages. A pivotal cytokine that mediates inflammatory reactions is TNF alpha that true to its name can stimulate anti-tumor immunity and hemorrhagic necrosis at high doses but has also recently been found to be expressed by tumor cells and acting as a tumor promoter (Zins, K., et al., Cancer Res. 67 (2007) 1038-1045; Balkwill, F., Cancer Metastasis Rev. 25 (2006) 409-416). The specific role of macrophages with respect to the tumor still needs to be better understood including the potential spatial and temporal dependence on their function and the relevance to specific tumor types.

Thus one embodiment of the invention are the CSF-1R antibodies described herein in for use in the treatment of cancer in combination with an anti-PD-L1 antibody as described herein. The term "cancer" as used herein may be, for example, lung cancer, non small cell lung (NSCL) cancer, bronchioloalviolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva. Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, neoplasms of the central nervous system (CNS), spinal axis tumors, brain stem glioma, glioblastoma multiforme, astrocytomas, schwanomas, cpendymonas, medulloblastomas, meningiomas, squamous cell carcinomas, pituitary adenoma, lymphoma, lymphocytic leukemia, including refractory versions of any of the above cancers, or a combination of one or more of the above cancers, in one preferred embodiment such cancer is a breast cancer, colorectal cancer, melanoma, head and neck cancer, lung cancer or prostate cancer. In one preferred embodiment such cancer is a breast cancer, ovarian cancer, cervical cancer, lung cancer or prostate cancer. In another preferred embodiment such cancer is breast cancer, lung cancer, colon cancer, ovarian cancer, melanoma cancer, bladder cancer, renal cancer, kidney cancer, liver cancer, head and neck cancer, colorectal cancer, pancreatic cancer, gastric carcinoma cancer, esophageal cancer, mesothelioma, prostate cancer, leukemia, lymphoma, myclomas. In one preferred embodiment such cancers are further characterized by CSF-1 or CSF-1R expression or overexpression. One further embodiment the invention are the CSF-1R antibodies of the present invention for use in the simultaneous treatment of primary tumors and new metastases. Thus another embodiment of the invention are the CSF-1R antibodies of the present invention for use in the treatment of periodontitis, histiocytosis X, osteoporosis, Paget's disease of bone (PDB), bone loss due to cancer therapy, periprosthetic osteolysis, glucocorticoid-induced osteoporosis, rheumatoid arthritis, psiratic arthritis, ostcoarthritis, inflammatory arthriditics, and inflammation.

Rabello, D., et al., Biochem. Biophys. Res. Commun. 347 (2006) 791-796 has demonstrated that SNPs in the CSF1 gene exhibited a positive association with aggressive periodontitis: an inflammatory disease of the periodontal tissues that causes tooth loss due to resorption of the alveolar bone.

Histiocytosis X (also called Langerhans cell histiocytosis, LCH) is a proliferative disease of Langerhans dendritic cells that appear to differentiate into osteoclasts in bone and extra osseous LCH lesions. Langerhans cells are derived from circulating monocytes. Increased levels of M-CSF that have been measured in sera and lesions where found to correlate with disease severity (da Costa, C. E., et al., J. Exp. Med. 201 (2005) 687-693). The disease occurs primarily in a pediatric patient population and has to be treated with chemotherapy when the disease becomes systemic or is recurrent.

The pathophysiology of osteoporosis is mediated by loss of bone forming osteoblasts and increased osteoclast dependent bone resorption. Supporting data has been described by Cenci et al showing that an anti-M-CSF antibody injection preserves bone density and inhibits bone resorption in ovariectornized mice (Cenci, S., et al., J. Clin. Invest. 105 (2000) 1279-1287). Recently a potential link between postmenopausal bone loss due to estrogen deficiency was identified and found that the presence of TNF alpha producing T-cell affected bone metabolism (Roggia, C., et al., Minerva Med. 95 (2004) 125-132). A possible mechanism could be the induction of M-CSF by TNF alpha in vivo. An important role for M-CSF in TNF-alpha-induced osteoclastogenesis was confirmed by the effect of an antibody directed against M-CSF that blocked the TNF alpha induced ostcolysis in mice and thereby making inhibitors of CSF-1R signaling potential targets for inflammatory arthritis (Kitaura, H., et al., J. Clin. Invest. 115 (2005) 3418-3427).

Paget's disease of bone (PDB) is the second most common bone metabolism disorder after osteoporosis in which focal abnormalities of increased bone turnover lead to complications such as bone pain, deformity, pathological fractures and deafness. Mutations in four genes have been identified that regulate normal osteoclast function and predispose individuals to PDB and related disorders: insertion mutations in TNFRSF11A, which encodes receptor activator of nuclear factor (NF) kappaB (RANK)—a critical regulator of osteoclast function, inactivating mutations of TNFRSF11B which encodes osteoprotegerin (a decoy receptor for RANK ligand), mutations of the sequestosome 1 gene (SQSTM1), which encodes an important scaffold protein in the NFkappaB pathway and mutations in the valosin-containing protein (VCP) gene. This gene encodes VCP, which has a role in targeting the inhibitor of NFkappaB for degradation by the proteasome (Daroszewska, A. and Ralston, S. H., Nat. Clin. Pract. Rheumatol. 2 (2006) 270-277). Targeted CSF-1R inhibitors provide an opportunity to block the deregulation of the RANKL signaling indirectly and add an additional treatment option to the currently used bisphosphonates.

Cancer therapy induced bone loss especially in breast and prostate cancer patients is an additional indication where a targeted CSF-1R inhibitor could prevent bone loss (Lester, J. E., et al., Br. J. Cancer 94 (2006) 30-35). With the improved prognosis for early breast cancer the long-term consequences of the adjuvant therapies become more important as some of the therapies including chemotherapy, irradiation, aromatase inhibitors and ovary ablation affect bone metabolism by decreasing the bone mineral density, resulting in increased risk for osteoporosis and associated fractures (Lester, J. E., et al., Br. J. Cancer 94 (2006) 30-35). The equivalent to adjuvant aromatase inhibitor therapy in breast cancer is androgen ablation therapy in prostate cancer which leads to loss of bone mineral density and significantly increases the risk of osteoporosis-related fractures (Stoch, S. A., et al., J. Clin. Endocrinol. Metab. 86 (2001) 2787-2791).

Targeted inhibition of CSF-1R signaling is likely to be beneficial in other indications as well when targeted cell types include osteoclasts and macrophages e.g. treatment of specific complications in response to joint replacement as a consequence of rheumatoid arthritis. Implant failure due to periprosthetic bone loss and consequent loosing of prostheses is a major complication of joint replacement and requires repeated surgery with high socioeconomic burdens for the individual patient and the health-care system. To date, there is no approved drug therapy to prevent or inhibit periprosthetic osteolysis (Drees, P., et al., Nat. Clin. Pract. Rheumatol. 3 (2007) 165-171).

Glucocorticoid-induced osteoporosis (GIOP) is another indication in which a CSF-1R inhibitor could prevent bone loss after longterm glucocorticosteroid use that is given as a result of various conditions among those chronic obstructive pulmonary disease, asthma and rheumatoid arthritis (Guzman-Clark, J. R., et al., Arthritis Rheum. 57 (2007) 140-146; Feldstein, A. C., et al., Osteoporos. Int. 16 (2005) 2168-2174).

Rheumatoid arthritis, psioratic arthritis and inflammatory arthriditis are in itself potential indications for CSF-1R signaling inhibitors in that they consist of a macrophage component and to a varying degree bone destruction (Ritchlin, C. T., et al., J. Clin. Invest. 111 (2003) 821-831). Osteoarthritis and rheumatoid arthritis are inflammatory autoimmune disease caused by the accumulation of macrophages in the connective tissue and infiltration of macrophages into the synovial fluid, which is at least partially mediated by M-CSF. Campbell, I., K., et al., J. Leukoc. Biol. 68 (2000) 144-150, demonstrated that M-CSF is produced by human-joint tissue cells (chondrocytes, synovial fibroblasts) in vitro and is found in synovial fluid of patients with rheumatoid arthritis, suggesting that it contributes to the synovial tissue proliferation and macrophage infiltration which is associated with the pathogenesis of the disease. Inhibition of CSF-1R signaling is likely to control the number of macrophages in the joint and alleviate the pain from the associated bone destruction. In order to minimize adverse effects and to further understand the impact of the CSF-1R signaling in these indications, one method is to specifically inhibit CSF-1R without targeting a myriad other kinases, such as Raf kinase.

Recent literature reports correlate increased circulating M-CSF with poor prognosis and atherosclerotic progression in chronic coronary artery disease (Saitoh, T., et al., J. Am. Coll. Cardiol. 35 (2000) 655-665; Ikonomidis, I., et al., Eur. Heart. J. 26 (2005) p. 1618-1624); M-CSF influences the atherosclerotic process by aiding the formation of foam cells (macrophages with ingested oxidized LDL) that express CSF-1R and represent the initial plaque (Murayama, T., et al., Circulation 99 (1999) 1740-1746).

Expression and signaling of M-CSF and CSF-1R is found in activated microglia. Microglia, which are resident macrophages of the central nervous system, can be activated by various insults, including infection and traumatic injury. M-CSF is considered a key regulator of inflammatory responses in the brain and M-CSF levels increase in HIV-1, encephalitis, Alzheimer's disease (AD) and brain tumors. Microgliosis as a consequence of autocrine signaling by M-CSF/CSF-1R results in induction of inflammatory cytokines and nitric oxides being released as demonstrated by e.g. using an experimental neuronal damage model (Hao, A. J., et al., Neuroscience 112 (2002) 889-900; Murphy, G. M., Jr., et al., J. Biol. Chem. 273 (1998) 20967-20971). Microglia that have increased expression of CSF-1R are found to surround plaques in AD and in the amyloid precursor protein V717F transgenic mouse model of AD (Murphy, G. M., Jr., et al., Am. J. Pathol. 157 (2000) 895-904). On the other hand op/op mice with fewer microglia in the brain resulted in fibrillar deposition of A-beta and neuronal loss compared to normal control suggesting that microglia do have a neuroprotective function in the development of AD lacking in the op/op mice (Kaku, M., et al., Brain Res. Brain Res. Protoc. 12 (2003) 104-108).

Expression and signaling of M-CSF and CSF-1R is associated with inflammatory bowel disease (IBD) (WO 2005/046657). The term "inflammatory bowel disease" refers to serious, chronic disorders of the intestinal tract characterized by chronic inflammation at various sites in the gastrointestinal tract, and specifically includes ulcerative colitis (UC) and Crohn's disease.

Thus another embodiment of the invention are the CSF-1R antibodies being characterized by the above mentioned amino acid sequences and amino acid sequence in combination with an anti-PD-L1 antibody being characterized by the above mentioned amino acid sequences and amino acid sequence for use in the treatment of periodontitis, histiocytosis X, osteoporosis, Paget's disease of bone (PDB), bone loss due to cancer therapy, periprosthetic osteolysis, glucocorticoid-induced osteoporosis, rheumatoid arthritis, psiratic arthritis, osteoarthritis, inflammatory arthridities, and inflammation.

The invention comprises the combination therapy with an antibody binding to human CSF-1R being characterized by the above mentioned amino acid sequences and amino acid sequence fragments with an anti-PD-L1 antibody being characterized by the above mentioned amino acid sequences and amino acid sequence fragments for the treatment of cancer.

The invention comprises the combination therapy with an antibody binding to human CSF-1R being characterized by the above mentioned amino acid sequences and amino acid sequence fragments with an anti-PD-L1 antibody being characterized by the above mentioned amino acid sequences and amino acid sequence fragments for the treatment of bone loss.

The invention comprises the combination therapy with an antibody binding to human CSF-1R being characterized by the above mentioned amino acid sequences and amino acid sequence fragments with an anti-PD-L1 antibody being characterized by the above mentioned amino acid sequences and amino acid sequence fragments for the prevention or treatment of metastasis.

The invention comprises the combination therapy of antibody binding to human CSF-1R being characterized by the above mentioned amino acid sequences and amino acid sequence fragments with an anti-PD-L1 antibody being characterized by the above mentioned amino acid sequences and amino acid sequence fragments for treatment of inflammatory diseases.

The invention comprises the combination therapy of antibody binding to human CSF-JR being characterized by the above mentioned amino acid sequences and amino acid sequence fragments with an anti-PD-L antibody being characterized by the above mentioned amino acid sequences and amino acid sequence fragments for use in treating or delaying progression of an immune related disease such as tumor immunity.

The invention comprises the combination therapy of antibody binding to human CSF-1R being characterized by the above mentioned amino acid sequences and amino acid sequence fragments with an anti-PD-L1 antibody being characterized by the above mentioned amino acid sequences and amino acid sequence fragments for use in stimulating an immune response or function, such as T cell activity.

The invention comprises the use of an antibody characterized in comprising the antibody binding to human CSF-1R being characterized by the above mentioned amino acid sequences and amino acid sequence fragments for the combination treatment of cancer with an anti-PD-L1 antibody or alternatively for the manufacture of a medicament for the combination treatment of cancer with an anti-PD-L1 antibody as described herein.

The invention comprises the use of an antibody characterized in comprising the antibody binding to human CSF-AR being characterized by the above mentioned amino acid sequences and amino acid sequence fragments for the combination treatment of bone loss with an anti-PD-L1 antibody as described herein or alternatively for the manufacture of a medicament for the combination treatment of bone loss with an anti-PD-L1 antibody as described herein.

The invention comprises the use of an antibody characterized in comprising the antibody binding to human CSF-1R being characterized by the above mentioned amino acid sequences and amino acid sequence fragments for the prevention or treatment of metastasis in the combination with an anti-PD-L1 antibody as described herein or alternatively for the manufacture of a medicament for the prevention or treatment of metastasis in the combination with an anti-PD-L1 antibody as described herein.

The invention comprises the use of an antibody characterized in comprising the antibody binding to human CSF-1R being characterized by the above mentioned amino acid sequences and amino acid sequence fragments for combination treatment of inflammatory diseases with an anti-PD-L1 antibody as described herein or alternatively for the manufacture of a medicament for the combination treatment of inflammatory diseases with an anti-PD-L1 antibody as described herein.

The invention comprises the use of an antibody characterized in comprising the antibody binding to human CSF-1R being characterized by the above mentioned amino acid sequences and amino acid sequence fragments for use in treating or delaying progression of an immune related disease such as tumor immunity in combination with an anti-PD-L1 antibody as described herein or alternatively for the manufacture of a medicament for use in treating or delaying progression of an immune related disease such as tumor immunity in combination with an anti-PD-L1 antibody as described herein.

The invention comprises the use of an antibody characterized in comprising the antibody binding to human CSF-1R being characterized by the above mentioned amino acid sequences and amino acid sequence fragments for use in stimulating an immune response or function, such as T cell activity in combination with an anti-PD-L1 antibody as described herein or alternatively for the manufacture of a medicament for use in stimulating an immune response or function, such as T cell activity in combination with an anti-PD-L1 antibody as described herein.

In one preferred embodiment of the invention the antibody which binds to human CSF-1R used in the above described combination treatments and medical uses of different diseases is characterized in comprising
a heavy chain variable domain VH of SEQ ID NO:39 and a light chain variable domain VL of SEQ ID NO:40, and
the antibody which binds to human PD-L1 used in such combination treatments is characterized in comprising
a heavy chain variable domain VH of SEQ ID NO:89 and a light chain variable domain VL of SEQ ID NO:92.

The antibodies described herein are preferably produced by recombinant means. Such methods are widely known in the state of the art and comprise protein expression in prokaryotic and eukaryotic cells with subsequent isolation of the antibody polypeptide and usually purification to a pharmaceutically acceptable purity. For the protein expression nucleic acids encoding light and heavy chains or fragments thereof are inserted into expression vectors by standard methods. Expression is performed in appropriate prokaryotic or eukaryotic host cells, such as CHO cells, NSO cells, SP2/0 cells, HEK293 cells, COS cells, yeast, or E. coli cells, and the antibody is recovered from the cells (from the supernatant or after cells lysis).

Recombinant production of antibodies is well-known in the state of the art and described, for example, in the review articles of Makrides, S. C., Protein Expr. Purif. 17 (1999) 183-202; Geisse, S., et al., Protein Expr. Purif. 8 (1996) 271-282; Kaufman, R. J., Mol. Biotechnol. 16 (2000) 151-161; Werner, R. G., Drug Res. 48 (1998) 870-880.

The antibodies may be present in whole cells, in a cell lysate, or in a partially purified, or substantially pure form. Purification is performed in order to eliminate other cellular components or other contaminants, e.g. other cellular nucleic acids or proteins, by standard techniques, including alkaline/SDS treatment, CsCl banding, column chromatography, agarose gel electrophoresis, and others well known in the art. See Ausubel, F., et al., ed. Current Protocols in Molecular Biology, Greene Publishing and Wiley Interscience, New York (1987).

Expression in NSO cells is described by, e.g., Barnes, L. M., et al., Cytotechnology 32 (2000) 109-123; Barnes, L. M., et al., Biotech. Bioeng. 73 (2001) 261-270. Transient expression is described by, e.g., Durocher, Y., et al., Nucl. Acids. Res. 30 (2002) E9. Cloning of variable domains is described by Orlandi, R., et al., Proc. Natl. Acad. Sci. USA 86 (1989) 3833-3837; Carter, P., et al., Proc. Natl. Acad. Sci. USA 89 (1992) 4285-4289; Norderhaug, L., et al., J. Immunol. Methods 204 (1997) 77-87. A preferred transient expression system (HEK 293) is described by Schlaeger, E.-J. and Christensen, K., in Cytotechnology 30 (1999) 71-83, and by Schlaeger, E.-J., in J. Immunol. Methods 194 (1996) 191-199.

The heavy and light chain variable domains according to the invention are combined with sequences of promoter, translation initiation, constant region, 3' untranslated region, polyadenylation, and transcription termination to form expression vector constructs. The heavy and light chain expression constructs can be combined into a single vector, co-transfected, serially transfected, or separately transfected into host cells which are then fused to form a single host cell expressing both chains.

The control sequences that are suitable for prokaryotes, for example, include a promoter, optionally an operator sequence, and a ribosome binding site. Eukaryotic cells are known to utilize promoters, enhancers and polyadenylation signals.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors or linkers are used in accordance with conventional practice.

The monoclonal antibodies are suitably separated from the culture medium by conventional immunoglobulin purification procedures such as, for example, protein A-Sepharose, hydroxylapatite chromatography, gel electrophoresis, dialysis, or affinity chromatography. DNA and RNA encoding the monoclonal antibodies are readily isolated and sequenced using conventional procedures. The hybridoma cells can serve as a source of such DNA and RNA. Once isolated, the DNA may be inserted into expression vectors, which are then transfected into host cells such as HEK 293 cells, CHO cells, or mycloma cells that do not otherwise produce immunoglobulin protein, to obtain the synthesis of recombinant monoclonal antibodies in the host cells.

As used herein, the expressions "cell", "cell line", and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Variant progeny that have the same function or biological activity as screened for in the originally transformed cell are included.

In another aspect, the present invention provides a composition, e.g. a pharmaceutical composition, containing one or a combination of monoclonal antibodies, or the antigen-binding portion thereof, of the present invention, formulated together with a pharmaceutically acceptable carrier.

As used herein, "pharmaceutically acceptable carrier" includes any and all solvents, dispersion media, coatings, antibacterial and antifungal agents, isotonic and absorption/resorption delaying agents, and the like that are physiologically compatible. Preferably, the carrier is suitable for injection or infusion.

A composition of the present invention can be administered by a variety of methods known in the art. As will be appreciated by the skilled artisan, the route and/or mode of administration will vary depending upon the desired results.

Pharmaceutically acceptable carriers include sterile aqueous solutions or dispersions and sterile powders for the preparation of sterile injectable solutions or dispersion. The use of such media and agents for pharmaceutically active substances is known in the art. In addition to water, the carrier can be, for example, an isotonic buffered saline solution.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient (effective amount). The selected dosage level will depend upon a variety of pharmacokinetic factors including the activity of the particular compositions of the present invention employed, or the ester, salt or amide thereof, the route of administration, the time of administration, the rate of excretion of the particular compound being employed, other drugs, compounds and/or materials used in combination with the particular compositions employed, the age, sex, weight, condition, general health and prior medical history of the patient being treated, and like factors well known in the medical arts.

The term "a method of treating" or its equivalent, when applied to, for example, cancer refers to a procedure or course of action that is designed to reduce or eliminate the number of cancer cells in a patient, or to alleviate the symptoms of a cancer. "A method of treating" cancer or another proliferative disorder does not necessarily mean that the cancer cells or other disorder will, in fact, be eliminated, that the number of cells or disorder will, in fact, be reduced, or that the symptoms of a cancer or other disorder will, in fact, be alleviated. Often, a method of treating cancer will be performed even with a low likelihood of success, but which, given the medical history and estimated survival expectancy of a patient, is nevertheless deemed to induce an overall beneficial course of action.

The terms "administered in combination with" or "co-administration", "co-administering", "combination therapy" or "combination treatment" refer to the administration of the anti-CSF-1R as described herein, and the anti-PD-L1 antibody as described herein e.g. as separate formulations/applications (or as one single formulation/application). The co-administration can be simultaneous or sequential in either order, wherein preferably there is a time period while both (or all) active agents simultaneously exert their biological activities. Said antibody and said further agent are co-administered either simultaneously or sequentially (e.g. intravenous (i.v.) through a continuous infusion. When both therapeutic agents are co-administered sequentially the dose is administered either on the same day in two separate administrations, or one of the agents is administered on day 1 and the second is co-administered on day 2 to day 7, preferably on day 2 to 4. Thus in one embodiment the term "sequentially" means within 7 days after the dose of the first component, preferably within 4 days after the dose of the first component; and the term "simultaneously" means at the same time. The terms "co-administration" with respect to the maintenance doses of anti-CSF-1R antibody and/or anti-PD-L1 antibody mean that the maintenance doses can be either co-administered simultaneously, if the treatment cycle is appropriate for both drugs, e.g. every week. Or the further agent is e.g. administered e.g. every first to third day and said antibody is administered every week. Or the maintenance doses are co-administered sequentially, either within one or within several days.

It is self-evident that the antibodies are administered to the patient in a "therapeutically effective amount" (or simply "effective amount") which is the amount of the respective compound or combination that will elicit the biological or medical response of a tissue, system, animal or human that is being sought by the researcher, veterinarian, medical doctor or other clinician.

The amount of co-administration and the timing of co-administration will depend on the type (species, gender, age, weight, etc.) and condition of the patient being treated and the severity of the disease or condition being treated. Said anti-CSF-1R antibody and further agent are suitably co-administered to the patient at one time or over a series of treatments e.g. on the same day or on the day after.

Depending on the type and severity of the disease, about 0.1 mg/kg to 50 mg/kg (e.g. 0.1-20 mg/kg) of said anti-CSF-1R antibody and/or anti-PD-L1 antibody; is an initial candidate dosage for co-administration of both drugs to the patient The invention comprises the use of the antibodies according to the invention for the treatment of a patient suffering from cancer, especially from colon, lung or pancreas cancer.

Depending on the type and severity of the disease, about 0.1 mg/kg to 50 mg/kg (e.g. 0.1-20 mg/kg) of said anti-CSF-1R antibody and/or anti-PD-L1 antibody; is an initial candidate dosage for co-administration of both drugs to the patient The invention comprises the use of the antibodies according to the invention for the treatment of a patient suffering from cancer, especially from colon, lung or pancreas cancer.

In addition to the anti-CSF-1R antibody in combination with the anti-PD-L antibody also a chemotherapeutic agent can be administered.

In one embodiment such additional chemotherapeutic agents, which may be administered with anti-CSF-1R antibody as described herein and the anti-PD-L1 antibody as described herein, include, but are not limited to, anti-neoplastic agents including alkylating agents including: nitrogen mustards, such as mechlorethaminc, cyclophosphamide, ifosfamide, melphalan and chlorambucil; nitrosoureas, such as carmustine (BCNU), lomustine (CCNU), and semustine (methyl-CCNU); Temodal™ (temozolamide), ethylenimines/methylmelamine such as thriethylenemelamine (TEM), triethylene, thiophosphoramide (thiotepa), hexamethylmelamine (HMM, altretamine); alkyl sulfonates such as busulfan; triazines such as dacarbazine (DTIC); antimetabolites including folic acid analogs such as methotrexate and trimetrexate, pyrimidine analogs such as 5-fluorouracil (5FU), fluorodeoxyuridine, gemcitabine, cytosine arabinoside (AraC, cytarabine), 5-azacytidine, 2,2'-difluorodeoxycytidine, purine analogs such as 6-merca.rho-.topurine, 6-thioguamne, azathioprine, T-deoxycoformycin (pentostatin), erythrohydroxynonyladenine (EHNA), fludarabine phosphate, and 2-chlorodeoxyadenosine (cladribine, 2-CdA); natural products including antimitotic drugs such as paclitaxel, vinca alkaloids including vinblastine (VLB), vincristine, and vinorelbine, taxotere, estramustine, and estramustine phosphate; pipodophylotoxins such as etoposide and teniposide; antibiotics such as actinomycin D, daunomycin (rubidomycin), doxorubicin, mitoxantrone, idarubicin, bleomycins, plicamycin (mithramycin), mitomycin C, and actinomycin; enzymes such as L-asparaginase; biological response modifiers such as interferon-alpha, IL-2, G-CSF and GM-CSF; miscellaneous agents including platinum coordination complexes such as oxaliplatin, cisplatin and carboplatin, anthracenediones such as mitoxantrone, substituted urea such as hydroxyura, methylhydrazine derivatives including N-methylhydrazine (MIH) and procarbazine, adrenocortical suppressants such as mitotane (o, p-DDD) and aminoglutethimide; hormones and antagonists including adrenocorticosteroid antagonists such as prednisone and equivalents, dexamethasone and aminoglutethimide; Gemzar™ (gcmcitabine), progestin such as hydroxyprogesterone caproate, medroxyprogesterone acetate and mcgestrol acetate; estrogen such as diethylstilbestrol and ethinyl estradiol equivalents; antiestrogen such as tamoxifen; androgens including testosterone propionate and fluoxymesteronc/equivalents; antiandrogens such as flutamide, gonadotropin-releasing hormone analogs and leuprolide; and non-steroidal antiandrogens such as flutamide. Therapies targeting epigenetic mechanism including, but not limited to, histone deacetylase inhibitors, demethylating agents (e.g., Vidaza) and release of transcriptional repression (ATRA) therapies can also be combined with the antigen binding proteins. In one embodiment the chemotherapeutic agent is selected from the group consisting of taxanes (like e.g. paclitaxel (Taxol), docetaxel (Taxotere), modified paclitaxel (e.g., Abraxane and Opaxio), doxorubicin, sunitinib (Sutent), sorafenib (Nexavar), and other multikinase inhibitors, oxaliplatin, cisplatin and carboplatin, etoposide, gemcitabine, and vinblastine. In one embodiment the chemotherapeutic agent is selected from the group consisting of taxanes (like e.g. taxol (paclitaxel), docetaxel (Taxotere), modified paclitaxel (e.g. Abraxane and Opaxio). In one embodiment, the additional chemotherapeutic agent is selected from 5-fluorouracil (5-FU), leucovorin, irinotecan, or oxaliplatin. In one embodiment the chemotherapeutic agent is 5-fluorouracil, Icucovorin and irinotecan (FOLFIRI). In one embodiment the chemotherapeutic agent is 5-fluorouracil, and oxaliplatin (FOLFOX).

Specific examples of combination therapies with additional chemotherapeutic agents include, for instance, therapies taxanes (e.g., docetaxel or paclitaxel) or a modified paclitaxel (e.g., Abraxane or Opaxio), doxorubicin), capecitabine and/or bevacizumab (Avastin) for the treatment of breast cancer; therapies with carboplatin, oxaliplatin, cisplatin, paclitaxel, doxorubicin (or modified doxorubicin (Caelyx or Doxil)), or topotecan (Hycamtin) for ovarian cancer, the therapies with a multi-kinase inhibitor, MKI, (Sutent, Nexavar, or 706) and/or doxorubicin for treatment of kidney cancer; therapies with oxaliplatin, cisplatin and/or radiation for the treatment of squamous cell carcinoma; therapies with taxol and/or carboplatin for the treatment of lung cancer.

Therefore, in one embodiment the additional chemotherapeutic agent is selected from the group of taxanes (docetaxel or paclitaxel or a modified paclitaxel (Abraxane or Opaxio), doxorubicin, capecitabine and/or bevacizumab for the treatment of breast cancer.

In one embodiment the CSF-1R antibody/PD-L1 antibody combination therapy is no chemotherapeutic agents are administered.

The invention comprises also a method for the treatment of a patient suffering from such disease.

The invention further provides a method for the manufacture of a pharmaceutical composition comprising an effective amount of an antibody according to the invention together with a pharmaceutically acceptable carrier and the use of the antibody according to the invention for such a method.

The invention further provides the use of an antibody according to the invention in an effective amount for the manufacture of a pharmaceutical agent, preferably together with a pharmaceutically acceptable carrier, for the treatment of a patient suffering from cancer.

The invention also provides the use of an antibody according to the invention in an effective amount for the manufacture of a pharmaceutical agent, preferably together with a pharmaceutically acceptable carrier, for the treatment of a patient suffering from cancer.

The following examples, sequence listing and figures are provided to aid the understanding of the present invention, the true scope of which is set forth in the appended claims. It is understood that modifications can be made in the procedures set forth without departing from the spirit of the invention.

DESCRIPTION OF THE SEQUENCES

SEQ ID NO: 1 heavy chain CDR3, Mab 2F11
SEQ ID NO: 2 heavy chain CDR2, Mab 2F11
SEQ ID NO: 3 heavy chain CDR1, Mab 2F11
SEQ ID NO: 4 light chain CDR3, Mab 2F11
SEQ ID NO: 5 light chain CDR2, Mab 2F11
SEQ ID NO: 6 light chain CDR1, Mab 2F11
SEQ ID NO: 7 heavy chain variable domain, Mab 2F11
SEQ ID NO: 8 light chain variable domain, Mab 2F11
SEQ ID NO: 9 heavy chain CDR3, Mab 2E10
SEQ ID NO: 10 heavy chain CDR2, Mab 2E10
SEQ ID NO: 11 heavy chain CDR1, Mab 2E10
SEQ ID NO: 12 light chain CDR3, Mab 2E10
SEQ ID NO: 13 light chain CDR2, Mab 2E10
SEQ ID NO: 14 light chain CDR1, Mab 2E10
SEQ ID NO: 15 heavy chain variable domain, Mab 2E10
SEQ ID NO: 16 light chain variable domain, Mab 2E10
SEQ ID NO: 17 heavy chain CDR3, hMab 2F11-c11
SEQ ID NO: 18 heavy chain CDR2, hMab 2F11-c11
SEQ ID NO: 19 heavy chain CDR1, hMab 2F11-c11
SEQ ID NO: 20 light chain CDR3, hMab 2F11-c11
SEQ ID NO: 21 light chain CDR2, hMab 2F11-c11
SEQ ID NO: 22 light chain CDR1, hMab 2F11-c11
SEQ ID NO: 23 heavy chain variable domain, hMab 2F11-c11
SEQ ID NO: 24 light chain variable domain, hMab 2F11-c11
SEQ ID NO: 25 heavy chain CDR3, hMab 2F11-d8
SEQ ID NO: 26 heavy chain CDR2, hMab 2F11-d8
SEQ ID NO: 27 heavy chain CDR1, hMab 2F11-d8
SEQ ID NO: 28 light chain CDR3, hMab 2F11-d8
SEQ ID NO: 29 light chain CDR2, hMab 2F11-d8
SEQ ID NO: 30 light chain CDR1, hMab 2F11-d8
SEQ ID NO: 31 heavy chain variable domain, hMab 2F11-d8
SEQ ID NO: 32 light chain variable domain, hMab 2F11-d8
SEQ ID NO: 33 heavy chain CDR3, hMab 2F11-c7
SEQ ID NO: 34 heavy chain CDR2, hMab 2F11-c7
SEQ ID NO: 35 heavy chain CDR1, hMab 2F11-e7
SEQ ID NO: 36 light chain CDR3, hMab 2F11-c7
SEQ ID NO: 37 light chain CDR2, hMab 2F11-c7
SEQ ID NO: 38 light chain CDR1, hMab 2F11-7
SEQ ID NO: 39 heavy chain variable domain, hMab 2F11-e7
SEQ ID NO: 40 light chain variable domain, hMab 2F11-e7
SEQ ID NO: 41 heavy chain CDR3, hMab 2F11-f12
SEQ ID NO: 42 heavy chain CDR2, hMab 2F11-f12
SEQ ID NO: 43 heavy chain CDR, hMab 2F11-f12
SEQ ID NO: 44 light chain CDR3, hMab 2F11-f12
SEQ ID NO: 45 light chain CDR2, hMab 2F11-f12
SEQ ID NO: 46 light chain CDR1, hMab 2F11-f12

SEQ ID NO: 47 heavy chain variable domain, hMab 2F11-f12
SEQ ID NO: 48 light chain variable domain, hMab 2F11-f12
SEQ ID NO: 49 heavy chain CDR3, hMab 2F11-g1
SEQ ID NO: 50 heavy chain CDR2, hMab 2F11-g1
SEQ ID NO: 51 heavy chain CDR1, hMab 2F11-g1
SEQ ID NO: 52 light chain CDR3, hMab 2F11-g1
SEQ ID NO: 53 light chain CDR2, hMab 2F11-g1
SEQ ID NO: 54 light chain CDR1, hMab 2F1-g1
SEQ ID NO: 55 heavy chain variable domain, hMab 2F11-g1
SEQ ID NO: 56 light chain variable domain, hMab 2F11-g1
SEQ ID NO: 57 human kappa light chain constant region
SEQ ID NO: 58 human heavy chain constant region derived from IgG1
SEQ ID NO: 59 human heavy chain constant region derived from IgG1 mutated on L234A and L235A
SEQ ID NO: 60 human heavy chain constant region derived from IgG4
SEQ ID NO: 61 human heavy chain constant region derived from IgG4 mutated on S228P
SEQ ID NO:62 human wildtype CSF-1R (wt CSF-1R) (including signal sequence)
SEQ ID NO: 63 human mutant CSF-1R L301S Y969F (including signal sequence)
SEQ ID NO: 64 human CSF-1R Extracellular Domain (domains D1-D5)
SEQ ID NO: 65 human CSF-1R fragment delD4
SEQ ID NO: 66 human CSF-1R fragment domains D1-D3
SEQ ID NO: 67 signal peptide
SEQ ID NO: 68 Primer
SEQ ID NO: 69 heavy chain CDR3, Mab 1G10
SEQ ID NO: 70 heavy chain CDR2, Mab 1G10
SEQ ID NO: 71 heavy chain CDR1, Mab 1G10
SEQ ID NO: 72 light chain CDR3, Mab 1G10
SEQ ID NO: 73 light chain CDR2, Mab 1G10
SEQ ID NO: 74 light chain CDR1, Mab 1G10
SEQ ID NO: 75 heavy chain variable domain, Mab 1G10
SEQ ID NO: 76 light chain variable domain, Mab 1G10
SEQ ID NO: 77 heavy chain CDR3, Mab 2H7
SEQ ID NO: 78 heavy chain CDR2, Mab 2H7
SEQ ID NO: 79 heavy chain CDR1, Mab 2H7
SEQ ID NO: 80 light chain CDR3, Mab 2H7
SEQ ID NO: 81 light chain CDR2, Mab 2H7
SEQ ID NO: 82 light chain CDR1, Mab 2H7
SEQ ID NO: 83 heavy chain variable domain, Mab 2H7
SEQ ID NO: 84 light chain variable domain, Mab 2H7
SEQ ID NO: 85 human CSF-1R fragment domains D4-D5
SEQ ID NO: 86 human CSF-1 (including signal sequence)
SEQ ID NO: 87 human IL-34 (including signal sequence)
SEQ ID NO: 88 human PD-L1 (including signal sequence)
SEQ ID NO: 89 heavy chain variable domain VH variant 1, anti-PD-L1 243.55
SEQ ID NO:90 heavy chain variable domain VH variant 2, anti-PD-L1 243.55
SEQ ID NO:91 heavy chain variable domain VH variant 3, anti-PD-L1 243.55
SEQ ID NO: 92 light chain variable domain VL variant 1, anti-PD-L1 243.55
SEQ ID NO: 93 light chain variable domain VL variant 2, anti-PD-L1 243.55
SEQ ID NO: 94 light chain variable domain VL variant 3, anti-PD-L1 243.55
SEQ ID NO: 95 light chain variable domain VL variant 4, anti-PD-L1 243.55
SEQ ID NO: 96 light chain variable domain VL variant 5, anti-PD-L1 243.55
SEQ ID NO: 97 light chain variable domain VL variant 6, anti-PD-L1 243.55
SEQ ID NO: 98 light chain variable domain VL variant 7, anti-PD-L1 243.55
SEQ ID NO: 99 light chain variable domain VL variant 8, anti-PD-L1 243.55
SEQ ID NO: 100 light chain variable domain VL variant 9, anti-PD-L1 243.55
SEQ ID NO: 101 light chain variable domain VL variant 10, anti-PD-L1 243.55
SEQ ID NO: 102 light chain variable domain VL variant 11, anti-PD-L1 243.55
SEQ ID NO: 103 light chain variable domain VL variant 12, anti-PD-L1 243.55
SEQ ID NO: 104 light chain variable domain VL variant 13, anti-PD-L1 243.55
SEQ ID NO: 105 light chain variable domain VL variant 14, anti-PD-L1 243.55
SEQ ID NO: 106 light chain variable domain VL variant 15, anti-PD-L1 243.55
SEQ ID NO: 107 light chain variable domain VL variant 16, anti-PD-L1 243.55

In the Following Embodiment of the Invention are Described

1. A) An antibody which binds to human CSF-1R wherein the antibody is administered in combination with an antibody which binds to human PD-L1 for use in the treatment of cancer, for use in the prevention or treatment of metastasis, for use in the treatment inflammatory diseases, for use in the treatment of bone loss, for use in treating or delaying progression of an immune related disease such as tumor immunity, or for use in stimulating an immune response or function, such as T cell activity; or B) the use of an antibody which binds to human CSF-1R for the manufacture of a medicament for use in the treatment of cancer, for use in the prevention or treatment of metastasis, for use in the treatment inflammatory diseases, for use in the treatment of bone loss, for use in treating or delaying progression of an immune related disease such as tumor immunity, or for use in stimulating an immune response or function, such as T cell activity, wherein the antibody is administered in combination with an antibody which binds to human PD-L1;

wherein the antibody which binds to human CSF-1R used in the combination therapy is characterized in comprising a) a heavy chain variable domain VH of SEQ ID NO:23 and a light chain variable domain VL of SEQ ID NO:24, or
b) a heavy chain variable domain VH of SEQ ID NO:31 and a light chain variable domain VL of SEQ ID NO:32, or
c) a heavy chain variable domain VH of SEQ ID NO:39 and a light chain variable domain VL of SEQ ID NO:40, or
d) a heavy chain variable domain VH of SEQ ID NO:47 and a light chain variable domain VL of SEQ ID NO:48, or
e) a heavy chain variable domain VH of SEQ ID NO:55 and a light chain variable domain VL of SEQ ID NO:56;

and the antibody which binds to human PD-L1 used in the combination therapy is characterized in comprising
a) a heavy chain variable domain VH of SEQ ID NO:89 and a light chain variable domain VL of SEQ ID NO:92, or
b) a heavy chain variable domain VH of SEQ ID NO:90 and a light chain variable domain VL of SEQ ID NO:93, or
c) a heavy chain variable domain VH of SEQ ID NO:90 and a light chain variable domain VL of SEQ ID NO:94, or
d) a heavy chain variable domain VH of SEQ ID NO:90 and a light chain variable domain VL of SEQ ID NO:95, or
e) a heavy chain variable domain VH of SEQ ID NO:90 and a light chain variable domain VL of SEQ ID NO:96, or
f) a heavy chain variable domain VH of SEQ ID NO:90 and a light chain variable domain VL of SEQ ID NO:97, or
g) a heavy chain variable domain VH of SEQ ID NO:90 and a light chain variable domain VL of SEQ ID NO:98, or
h) a heavy chain variable domain VH of SEQ ID NO:90 and a light chain variable domain VL of SEQ ID NO:99, or
i) a heavy chain variable domain VH of SEQ ID NO:90 and a light chain variable domain VL of SEQ ID NO:100, or
j) a heavy chain variable domain VH of SEQ ID NO:90 and a light chain variable domain VL of SEQ ID NO:101, or
k) a heavy chain variable domain VH of SEQ ID NO:90 and a light chain variable domain VL of SEQ ID NO:102, or
l) a heavy chain variable domain VH of SEQ ID NO:90 and a light chain variable domain VL of SEQ ID NO:103, or
m) a heavy chain variable domain VH of SEQ ID NO:90 and a light chain variable domain VL of SEQ ID NO:104, or
n) a heavy chain variable domain VH of SEQ ID NO:90 and a light chain variable domain VL of SEQ ID NO:105, or
o) a heavy chain variable domain VH of SEQ ID NO:90 and a light chain variable domain VL of SEQ ID NO:106, or
p) a heavy chain variable domain VH of SEQ ID NO:91 and a light chain variable domain VL of SEQ ID NO:107.

2. Use of a combination of
A) an antibody which binds to human CSF-1R, comprising
a) a heavy chain variable domain VH of SEQ ID NO:23 and a light chain variable domain VL of SEQ ID NO:24, or
b) a heavy chain variable domain VH of SEQ ID NO:31 and a light chain variable domain VL of SEQ ID NO:32, or
c) a heavy chain variable domain VH of SEQ ID NO:39 and a light chain variable domain VL of SEQ ID NO:40, or
d) a heavy chain variable domain VH of SEQ ID NO:47 and a light chain variable domain VL of SEQ ID NO:48, or
e) a heavy chain variable domain VH of SEQ ID NO:55 and a light chain variable domain VL of SEQ ID NO:56;
and
B) an antibody which binds to human PD-L1 comprising
a) a heavy chain variable domain VH of SEQ ID NO:89 and a light chain variable domain VL of SEQ ID NO:92, or
b) a heavy chain variable domain VH of SEQ ID NO:90 and a light chain variable domain VL of SEQ ID NO:93, or
c) a heavy chain variable domain VH of SEQ ID NO:90 and a light chain variable domain VL of SEQ ID NO:94, or
d) a heavy chain variable domain VH of SEQ ID NO:90 and a light chain variable domain VL of SEQ ID NO:95, or
e) a heavy chain variable domain VH of SEQ ID NO:90 and a light chain variable domain VL of SEQ ID NO:96, or
f) a heavy chain variable domain VH of SEQ ID NO:90 and a light chain variable domain VL of SEQ ID NO:97, or
g) a heavy chain variable domain VH of SEQ ID NO:90 and a light chain variable domain VL of SEQ ID NO:98, or
h) a heavy chain variable domain VH of SEQ ID NO:90 and a light chain variable domain VL of SEQ ID NO:99, or
i) a heavy chain variable domain VH of SEQ ID NO:90 and a light chain variable domain VL of SEQ ID NO:100, or
j) a heavy chain variable domain VH of SEQ ID NO:90 and a light chain variable domain VL of SEQ ID NO:101, or
k) a heavy chain variable domain VH of SEQ ID NO:90 and a light chain variable domain VL of SEQ ID NO:102, or
l) a heavy chain variable domain VH of SEQ ID NO:90 and a light chain variable domain VL of SEQ ID NO:103, or
m) a heavy chain variable domain VH of SEQ ID NO:90 and a light chain variable domain VL of SEQ ID NO:104, or
n) a heavy chain variable domain VH of SEQ ID NO:90 and a light chain variable domain VL of SEQ ID NO:105, or
o) a heavy chain variable domain VH of SEQ ID NO:90 and a light chain variable domain VL of SEQ ID NO:106, or
p) a heavy chain variable domain VH of SEQ ID NO:91 and a light chain variable domain VL of SEQ ID NO:107.
for the manufacture of a medicament for use in the treatment of cancer, for use in the prevention or treatment of metastasis, for use in the treatment inflammatory diseases, for use in the treatment of bone loss, for use in treating or delaying progression of an immune related disease such as tumor immunity, or for use in stimulating an immune response or function, such as T cell activity, wherein the antibody is administered in combination with an antibody which binds to human PD-L1

3. The antibody or use according to any one of embodiments 1 or 2, for use in the treatment of cancer.

4. The antibody or use according to embodiment 3, for use in the treatment of breast cancer, lung cancer, colon cancer, ovarian cancer, melanoma cancer, bladder cancer, renal cancer, kidney cancer, liver cancer, head and neck cancer, colorectal cancer, pancreatic cancer, gastric carcinoma cancer, esophageal cancer, mesothelioma, prostate cancer, leukemia, lymphomas, myelomas.

5. The antibody or use according to any one of embodiments 1 or 2, for use in the prevention or treatment of metastasis.

6. The antibody or use according to any one of embodiments 1 or 2, for use in the treatment of bone loss.

7. The antibody or use according to any one of embodiments 1 or 2, for use in the treatment of inflammatory diseases.

8. The antibody or use according to any one of embodiments 1 or 2, for use in treating or delaying progression of an immune related disease such as tumor immunity.

9. The antibody or use according to any one of embodiments 1 or 2 for use in stimulating an immune response or function, such as T cell activity.

10. A) An antibody which binds to human CSF-1R wherein the antibody is administered in combination with an antibody which binds to human PD-L1 for use in
   i) the inhibition of cell proliferation in CSF-1R ligand-dependent and/or CSF-1 ligand-independent CSF-1R expressing tumor cells;
   ii) the inhibition of cell proliferation of tumors with CSF-1R ligand-dependent and/or CSF-1R ligand-independent CSF-1R expressing macrophage infiltrate;
   iii) the inhibition of cell survival (in CSF-1R ligand-dependent and/or CSF-1R ligand-independent) CSF-1R expressing monocytes and macrophages; and/or
   iv) the inhibition of cell differentiation (in CSF-1R ligand-dependent and/or CSF-1R ligand-independent) CSF-1R expressing monocytes into macrophages;
   or
B) use of an antibody which binds to human CSF-1R for the manufacture of a medicament for use in
   i) the inhibition of cell proliferation in CSF-1R ligand-dependent and/or CSF-1 ligand-independent CSF-1R expressing tumor cells;
   ii) the inhibition of cell proliferation of tumors with CSF-1R ligand-dependent and/or CSF-1R ligand-independent CSF-1R expressing macrophage infiltrate;
   iii) the inhibition of cell survival (in CSF-1R ligand-dependent and/or CSF-1R ligand-independent) CSF-1R expressing monocytes and macrophages; and/or
   iv) the inhibition of cell differentiation (in CSF-1R ligand-dependent and/or CSF-1R ligand-independent) CSF-1R expressing monocytes into macrophages,
   wherein the antibody is administered in combination with an antibody which binds to human PD-L1;
   wherein the antibody which binds to human CSF-1R used in the combination therapy is characterized in comprising
      a) a heavy chain variable domain VH of SEQ ID NO:23 and a light chain variable domain VL of SEQ ID NO:24, or
      b) a heavy chain variable domain VH of SEQ ID NO:31 and a light chain variable domain VL of SEQ ID NO:32, or
      c) a heavy chain variable domain VH of SEQ ID NO:39 and a light chain variable domain VL of SEQ ID NO:40, or
      d) a heavy chain variable domain VH of SEQ ID NO:47 and a light chain variable domain VL of SEQ ID NO:48, or
      e) a heavy chain variable domain VH of SEQ ID NO:55 and a light chain variable domain VL of SEQ ID NO:56;
   and the antibody which binds to human PD-L1 used in the combination therapy is characterized in comprising
      a) a heavy chain variable domain VH of SEQ ID NO:89 and a light chain variable domain VL of SEQ ID NO:92, or
      b) a heavy chain variable domain VH of SEQ ID NO:90 and a light chain variable domain VL of SEQ ID NO:93, or
      c) a heavy chain variable domain VH of SEQ ID NO:90 and a light chain variable domain VL of SEQ ID NO:94, or
      d) a heavy chain variable domain VH of SEQ ID NO:90 and a light chain variable domain VL of SEQ ID NO:95, or
      e) a heavy chain variable domain VH of SEQ ID NO:90 and a light chain variable domain VL of SEQ ID NO:96, or
      f) a heavy chain variable domain VH of SEQ ID NO:90 and a light chain variable domain VL of SEQ ID NO:97, or
      g) a heavy chain variable domain VH of SEQ ID NO:90 and a light chain variable domain VL of SEQ ID NO:98, or
      h) a heavy chain variable domain VH of SEQ ID NO:90 and a light chain variable domain VL of SEQ ID NO:99, or
      i) a heavy chain variable domain VH of SEQ ID NO:90 and a light chain variable domain VL of SEQ ID NO:100, or
      j) a heavy chain variable domain VH of SEQ ID NO:90 and a light chain variable domain VL of SEQ ID NO:101, or
      k) a heavy chain variable domain VH of SEQ ID NO:90 and a light chain variable domain VL of SEQ ID NO:102, or
      l) a heavy chain variable domain VH of SEQ ID NO:90 and a light chain variable domain VL of SEQ ID NO:103, or
      m) a heavy chain variable domain VH of SEQ ID NO:90 and a light chain variable domain VL of SEQ ID NO:104, or
      n) a heavy chain variable domain VH of SEQ ID NO:90 and a light chain variable domain VL of SEQ ID NO:105, or
      o) a heavy chain variable domain VH of SEQ ID NO:90 and a light chain variable domain VL of SEQ ID NO:106, or
      p) a heavy chain variable domain VH of SEQ ID NO:91 and a light chain variable domain VL of SEQ ID NO:107.

11. A) An antibody which binds to human CSF-1R, for use in the treatment of a patient having a CSF-1R expressing tumor or having a tumor with CSF-1R expressing macrophage infiltrate, wherein the tumor is characterized by an increase of CSF-1R ligand and wherein the anti-CSF-1R antibody is administered in combination with an antibody which binds to human PD-L1, or B) use of an antibody which binds to human CSF-1R, for the manufacture of a medicament for use in the treatment of a patient having a CSF-1R expressing tumor or having a tumor with CSF-1R expressing macrophage infiltrate, wherein the tumor is characterized by an increase of CSF-1R ligand and wherein the anti-CSF-1R antibody is administered in combination with an antibody which binds to human PD-L1, wherein the antibody which binds to human CSF-1R used in the combination therapy is characterized in comprising
a) a heavy chain variable domain VH of SEQ ID NO:23 and a light chain variable domain VL of SEQ ID NO:24, or
b) a heavy chain variable domain VH of SEQ ID NO:31 and a light chain variable domain VL of SEQ ID NO:32, or
c) a heavy chain variable domain VH of SEQ ID NO:39 and a light chain variable domain V L of SEQ ID NO:40, or
d) a heavy chain variable domain VH of SEQ ID NO:47 and a light chain variable domain VL of SEQ ID NO:48, or
c) a heavy chain variable domain VH of SEQ ID NO:55 and a light chain variable domain VL of SEQ ID NO:56;

and the antibody which binds to human PD-L1 used in the combination therapy is characterized in comprising
a) a heavy chain variable domain VH of SEQ ID NO:89 and a light chain variable domain VL of SEQ ID NO:92, or
b) a heavy chain variable domain VH of SEQ ID NO:90 and a light chain variable domain VL of SEQ ID NO:93, or
c) a heavy chain variable domain VH of SEQ ID NO:90 and a light chain variable domain VL of SEQ ID NO:94, or
d) a heavy chain variable domain VH of SEQ ID NO:90 and a light chain variable domain VL of SEQ ID NO:95, or
c) a heavy chain variable domain VH of SEQ ID NO:90 and a light chain variable domain VL of SEQ ID NO:96, or
f) a heavy chain variable domain VH of SEQ ID NO:90 and a light chain variable domain VL of SEQ ID NO:97, or
g) a heavy chain variable domain VH of SEQ ID NO:90 and a light chain variable domain VL of SEQ ID NO:98, or
h) a heavy chain variable domain VH of SEQ ID NO:90 and a light chain variable domain VL of SEQ ID NO:99, or
i) a heavy chain variable domain VH of SEQ ID NO:90 and a light chain variable domain VL of SEQ ID NO:100, or
j) a heavy chain variable domain VH of SEQ ID NO:90 and a light chain variable domain VL of SEQ ID NO:101, or
k) a heavy chain variable domain VH of SEQ ID NO:90 and a light chain variable domain VL of SEQ ID NO:102, or
l) a heavy chain variable domain VH of SEQ ID NO:90 and a light chain variable domain VL of SEQ ID NO:103, or
m) a heavy chain variable domain VH of SEQ ID NO:90 and a light chain variable domain VL of SEQ ID NO:104, or
n) a heavy chain variable domain VH of SEQ ID NO:90 and a light chain variable domain VL of SEQ ID NO:105, or
o) a heavy chain variable domain VH of SEQ ID NO:90 and a light chain variable domain VL of SEQ ID NO:106, or
p) a heavy chain variable domain VH of SEQ ID NO:91 and a light chain variable domain VL of SEQ ID NO:107.

12. The antibody or use according any one of the preceding embodiments,
wherein the antibody which binds to human CSF-1R used in the combination therapy is characterized in comprising
c) a heavy chain variable domain VH of SEQ ID NO:39 and a light chain variable domain VL of SEQ ID NO:40, or
and wherein the antibody which binds to human PD-L1 used in the combination therapy is characterized in comprising
a) a heavy chain variable domain VH of SEQ ID NO:89 and a light chain variable domain VL of SEQ ID NO:92.

13. The antibody or use according any one of the preceding embodiments, characterized in that said antibodies are of human IgG1 subclass or human IgG4 subclass.

14. The antibody or use according to any one of the preceding embodiments, characterized in that said antibodies have reduced or minimal effector function.

15. The antibody or use according to any one of the preceding embodiments, wherein the minimal effector function results from an effectorless Fc mutation.

16. The antibody or use according to any one of the preceding embodiments, wherein the effectorless Fc mutation is L234A/L235A or L234A/L235A/P329G or N297A or D265A/N297A.

17. A) A method for
i) the inhibition of cell proliferation in CSF-1R ligand-dependent and/or CSF-1R ligand-independent CSF-1R expressing tumor cells;
ii) the inhibition of cell proliferation of tumors with CSF-1R ligand-dependent and/or CSF-1R ligand-independent CSF-1R expressing macrophage infiltrate;
iii) the inhibition of cell survival (in CSF-1R ligand-dependent and/or CSF-1R ligand-independent) CSF-1R expressing monocytes and macrophages; and/or
iv) the inhibition of cell differentiation (in CSF-1R ligand-dependent and/or CSF-1R ligand-independent) CSF-1R expressing monocytes into macrophages;
wherein an antibody which binds to human CSF-1R, is administered in combination with an antibody which binds to human PD-L1,
or
B) a method of treatment of a patient having a CSF-1R expressing tumor or having a tumor with CSF-1R expressing macrophage infiltrate, wherein the tumor is characterized by an increase of CSF-1R ligand and wherein an antibody which binds to human CSF-1R is administered in combination with an antibody which binds to human PD-L1, wherein the antibody which binds to human CSF-1R used in the combination therapy is characterized in comprising
a) a heavy chain variable domain VH of SEQ ID NO:23 and a light chain variable domain VL of SEQ ID NO:24, or
b) a heavy chain variable domain VH of SEQ ID NO:31 and a light chain variable domain VL of SEQ ID NO:32, or
c) a heavy chain variable domain VH of SEQ ID NO:39 and a light chain variable domain VL of SEQ ID NO:40, or
d) a heavy chain variable domain VH of SEQ ID NO:47 and a light chain variable domain VL of SEQ ID NO:48, or
e) a heavy chain variable domain VH of SEQ ID NO:55 and a light chain variable domain VL of SEQ ID NO:56;

and the antibody which binds to human PD-L1 used in the combination therapy is characterized in comprising
a) a heavy chain variable domain VH of SEQ ID NO:89 and a light chain variable domain V L of SEQ ID NO:92, or
b) a heavy chain variable domain VH of SEQ ID NO:90 and a light chain variable domain VL of SEQ ID NO:93, or
c) a heavy chain variable domain VH of SEQ ID NO:90 and a light chain variable domain VL of SEQ ID NO:94, or
d) a heavy chain variable domain VH of SEQ ID NO:90 and a light chain variable domain VL of SEQ ID NO:95, or
c) a heavy chain variable domain VH of SEQ ID NO:90 and a light chain variable domain VL of SEQ ID NO:96, or
f) a heavy chain variable domain VH of SEQ ID NO:90 and a light chain variable domain VL of SEQ ID NO:97, or
g) a heavy chain variable domain VH of SEQ ID NO:90 and a light chain variable domain VL of SEQ ID NO:98, or
h) a heavy chain variable domain VH of SEQ ID NO:90 and a light chain variable domain V L of SEQ ID NO:99, or
i) a heavy chain variable domain VH of SEQ ID NO:90 and a light chain variable domain VL of SEQ ID NO:100, or
j) a heavy chain variable domain VH of SEQ ID NO:90 and a light chain variable domain VL of SEQ ID NO:101, or
k) a heavy chain variable domain VH of SEQ ID NO:90 and a light chain variable domain VL of SEQ ID NO:102, or
l) a heavy chain variable domain VH of SEQ ID NO:90 and a light chain variable domain VL of SEQ ID NO:103, or
n) a heavy chain variable domain VH of SEQ ID NO:90 and a light chain variable domain VL of SEQ ID NO:104, or
n) a heavy chain variable domain VH of SEQ ID NO:90 and a light chain variable domain VL of SEQ ID NO:105, or
o) a heavy chain variable domain VH of SEQ ID NO:90 and a light chain variable domain VL of SEQ ID NO:106, or
p) a heavy chain variable domain VH of SEQ ID NO:91 and a light chain variable domain VL of SEQ ID NO:107.

EXAMPLES

Example

Inhibition of CSF-1-induced CSF-1R phosphorylation in NIH3T3-CSF-1R Recombinant Cells $4.5 \times 10^3$ NIH 3T3 cells, retrovirally infected with an expression vector for full-length CSF-1R, were cultured in DMEM (PAA Cat. No. E15-011), 2 mM L-glutamine (Sigma, Cat. No. G7513, 2 mM Sodium pyruvate, 1× nonessential amino acids, 10% FKS (PAA, Cat. No. A15-649) and 100 µg/ml PenStrep (Sigma, Cat. No. P4333 [10 mg/ml]) until they reached confluency. Thereafter cells were washed with serum-free DMEM media (PAA Cat. No. E15-011) supplemented with sodium selenite [5 ng/ml] (Sigma, Cat. No. S9133), transferrin [10 µg/ml] (Sigma, Cat. No. T8158), BSA [400 µg/ml] (Roche Diagnostics GmbH, Cat. No. 10735078), 4 mM L-glutamine (Sigma, Cat. No. G7513), 2 mM sodium pyruvate (Gibco, Cat. No. 11360), 1× nonessential amino acids (Gibco, Cat: 11140-035), 2-mercaptoethanol [0.05 mM] (Merck, Cat. No. M7522), 100 µg/ml and PenStrep (Sigma, Cat. No. P4333) and incubated in 30 µl of the same medium for 16 hours to allow for receptor up-regulation. 10 µl of diluted anti-CSR-1R antibodies were added to the cells for 1.5 h. Then cells were stimulated with 10 µl of 100 ng/ml hu CSF-1 (active 149 aa fragment of human CSF-1 (aa 33-181 of SEQ ID NO: 86); Biomol, DE, Cat. No. 60530) for 5 min. After the incubation, supernatant was removed, cells were washed twice with 80 µl of ice-cold PBS and 50 µl of freshly prepared ice-cold lysis buffer (150 mM NaCl/20 mM Tris pH 7.5/mM EDTA/1 mM EGTA/1% Triton X-100/protease inhibitor tablet (Roche Diagnostics GmbH Cat. No. 1 836 170) per 10 ml buffer/10 µl/ml phosphatase inhibitor cocktail 1 (Sigma Cat. No. P-2850, 100× Stock). 10 µl/ml protease inhibitor I (Sigma Cat. No. P-5726, 100× Stock)/10 µl/ml 1 M NaF) was added. After 30 minutes on ice the plates were shaken vigorously on a plateshaker for 3 minutes and then centrifuged 10 minutes at 2200 rpm (Heraeus Megafuge 10).

The presence of phosphorylated and total CSF-1 receptor in the cell lysate was analyzed with Elisa. For detection of the phosphorylated receptor the kit from R&D Systems (Cat. No. DYC3268-2) was used according to the instructions of the supplier. For detection of total CSF-1R 10 µl of the lysate was immobilized on plate by use of the capture antibody contained in the kit. Thereafter 1:750 diluted biotinylated anti CSF-1R antibody BAF329 (R&D Systems) and 1:1000 diluted streptavidin-HRP conjugate was added. After 60 minutes plates were developed with freshly prepared ABTS® solution and the absorbance was detected. Data were calculated as % of positive control without antibody and the ratio value phospho/total receptor expressed. The negative control was defined without addition of M-CSF-1. Anti CSF-1R SC 2-4A5 (Santa Cruz Biotechnology, US, see also Sherr, C. J. et al., Blood 73 (1989) 1786-1793), which inhibits the ligand-receptor interaction, was used as reference control.

TABLE 3

Calculated IC50 values for the inhibition of CSF-1 receptor phosphorylation.

| CSF-1R Mab | IC50 CSF-1R Phosphorylation [ng/ml] |
|---|---|
| Mab 2F11 | 219.4 |
| Mab 2E10 | 752.0 |
| Mab 2H7 | 703.4 |
| Mab 1G10 | 56.6 |
| SC-2-4A5 | 1006.6 |

Example 2

Growth Inhibition of NIH3T3-CSF-1R Recombinant Cells in 3D Culture Under Treatment with Anti-CSF-IR Monoclonal Antibodies N1H 3T3 cells, retrovirally infected with either an expression vector for full-length wildtype CSF-1R (SEQ ID NO: 62) or mutant CSF-1R L301S Y969F (SEQ ID NO: 63), were cultured in DMEM high glucose media (PAA, Pasching, Austria) supplemented with 2 mM L-glutamine, 2 mM sodium pyruvate and non-essential amino acids and 10% fetal bovine serum (Sigma, Taufkirchen, Germany) on poly-HEMA (poly(2-hydroxyethylmethacrylate)) (Polysciences, Warrington, Pa., USA)) coated dishes to prevent adherence to the plastic surface. Cells are seeded in medium replacing serum with 5 ng/ml sodium selenite, 10 mg/ml transferrin, 400 µg/ml BSA and 0.05 mM 2-mercaptoethanol. When treated with 100 ng/ml hu CSF-1 (active 149 aa fragment of human CSF-1 (aa 33-181 of SEQ ID NO: 86); Biomol, DE, Cat. No. 60530) wtCSF-1R (expressing cells form dense spheroids that grow three dimensionally, a property that is called anchorage independence. These spheroids resemble closely the three dimensional architecture and organization of solid tumors in situ. Mutant CSF-1R recombinant cells are able to form spheroids independent of the CSF-1 ligand. The anti-CSF-1R antibody according to the invention hMab 2F11-e7 and the anti-CSF-1R antibodies 1.2.SM (ligand displacing CSF-1R antibody described in WO 2009/026303), CXIIG6 (ligand displacing CSF-1R antibody described in WO 2009/112245), the goat polyclonal anti-CSF-1R antibody ab10676 (abcam), and SC 2-4A5 (Santa Cruz Biotechnology, US—see also Sherr, C. J. et al., Blood 73 (1989) 1786-1793) and Mab R&D-Systems 3291 were investigated. Reference control Mab R&D-Systems 3291 did not show inhibition of mutant CSF-1R recombinant cell proliferation.

Spheroid cultures were incubated for 3 days in the presence of different concentrations of antibody in order to determine an IC30 (concentration with 30 percent inhibition of cell viability). Maximum concentration was 20 µg/ml. The CellTiter-Glo® cell viability assay was used to detect cell viability by measuring the ATP-content of the cells.

TABLE 4

| CSF-1R Mab | wtCSF-IR IC$_{30}$ [µg/ml] | Mutant CSF-1R IC$_{30}$ [µg/ml] |
|---|---|---|
| hMab 2F11-c7 | 4.91 | 0.54 |
| 1.2.SM | 1.19 | >20 µg/ml (−19% inhibition at 20 µg/ml = 19% stimulation) |
| CXIIG6 | >20 µg/ml (21% inhibition at 20 µg/ml) | >20 µg/ml (−36% inhibition at 20 µg/ml = 36% stimulation) |
| ab10676 | 14.15 | >20 µg/ml (0% inhibition at 20 µg/ml) |
| SC 2-4A5 | 16.62 | 2.56 |

Example 3

Inhibition of Human Macrophage Differentiation Under Treatment with Anti-CSF-1R Monoclonal Antibodies Human monocytes were isolated from peripheral blood using the RosetteSep™ Human Monocyte Enrichment Cocktail (StemCell Tech.—Cat. No. 15028). Enriched monocyte populations were seeded into 96 well microtiter-plates ($2.5 \times 10^4$ cells/well) in 100 µl RPMI 1640 (Gibco—Cat. No. 31870) supplemented with 10% FCS (GIBCO—Cat. No. 011-090014M), 4 mM L-glutamine (GIBCO—Cat. No. 25030) and 1×PenStrep (Roche Cat. No. 1 074 440) at 37° C. and 5% CO$_2$ in a humidified atmosphere. When 150 ng/ml huCSF-1 was added to the medium, a clear differentiation into adherent macrophage could be observed. This differentiation could be inhibited by addition of anti-CSF-1R antibodies. Furthermore, the monocyte survival is affected and could be analyzed by CellTiter-Glo® cell viability assay. From the concentration dependent inhibition of the survival of monocytes by antibody treatment, an IC$_{50}$ was calculated (see Table below).

TABLE 5

| CSF-IR Mab | IC$_{50}$ [µg/ml] |
|---|---|
| Mab 2F11 | 0.08 |
| Mab 2E10 | 0.06 |
| Mab 2H7 | 0.03 |
| Mab 1G10 | 0.06 |
| SC 2-4A5 | 0.36 |

In a separate test series humanized versions of Mab 2 F11, e.g. hMab 2F11-c11, hMab 2F11-d8, hMab 2F11-c7, hMab 2F11-f12, showed IC$_{50}$ values of 0.07 µg/ml (hMab 2F11-c11), 0.07 µg/ml (hMab 2F1-d8), 0.04 µg/ml (hMab 2F11-7) and 0.09 µg/ml (hMab 2F11-f12).

Example 4

Inhibition of Human Macrophage Differentiation Under Treatment with Anti-CSF-1R Monoclonal Antibodies Human monocytes were isolated from peripheral blood using the RosetteSep™ Human Monocyte Enrichment Cocktail (StemCell Tech.—Cat. No. 15028). Enriched monocyte populations were seeded into 96 well microtiter-plates ($2.5 \times 10^4$ cells/well) in 100 µl RPMI 1640 (Gibco—Cat. No. 31870) supplemented with 10% FCS (GIBCO—Cat. No. 011-090014M), 4 mM L-glutamine (GIBCO—Cat. No. 25030) and 1×PenStrep (Roche Cat. No. 074 440) at 37° C. and 5% CO$_2$ in a humidified atmosphere. When 150 ng/ml huCSF-1 was added to the medium, a clear differentiation into adherent macrophage could be observed. This differentiation could be inhibited by addition of anti-CSF-1R antibodies. Furthermore, the monocyte survival is affected and could be analyzed by CellTiter-Glo® cell viability assay. From the concentration dependent inhibition of the survival of monocytes by antibody treatment, an $IC_{50}$ was calculated. Humanized versions of Mab 2 F11, e.g. hMab 2F11-c11, hMab 2F11-d8, hMab 2F111-e7, hMab 2F11-f12, showed $IC_{50}$ values of 0.07 µg/ml (hMab 2F11-c11), 0.07 µg/ml (hMab 2F11-d8), 0.04 µg/ml (hMab 2F11-e7) and 0.09 µg/ml (hMab 2F11-f12).

Example 5

Inhibition of Human M1 and M2 Macrophage Differentiation Under Treatment with Anti-CSF-1R Monoclonal Antibodies Human monocytes were isolated from peripheral blood using the RosettcSep™ Human Monocyte Enrichment Cocktail (StemCell Tech.—Cat. No. 15028). Enriched monocyte populations were seeded into 96 well microtiterplates ($2.5 \times 10^4$ cells/well) in 100 µl RPMI 1640 (Gibco—Cat. No. 31870) supplemented with 10% FCS (GIBCO—Cat. No. 011-090014M), 4 mM L-glutamine (GIBCO—Cat. No. 25030) and x PenStrep (Roche Cat. No. 1 074 440) at 37° C. and 5% $CO_2$ in a humidified atmosphere. When 100 ng/ml huCSF-1 was added for 6 days to the medium, a clear differentiation into adherent, M2 macrophages with elongated morphology could be observed. When 100 ng/ml huGM-CSF was added to the medium for 6 days, a clear differentiation into adherent, M1 macrophages with round morphology could be observed. This differentiation was associated with the expression of certain markers such as CD163 for M2 macrophages and CD80 or high MHC class II for M1 macrophages as assessed by flow cytometry. Cells were washed with PBS and, if adherent, detached using a 5 mM EDTA solution in PBS (20 min at 37° C.). Cells were then well resuspended, washed with staining buffer (5% FCS in PBS) and centrifuged at 300xg for 5 min. Pellets were resuspended in 1 ml staining buffer and cells counted in a Neubauer chamber. Approximately 1x10e5 cells were transferred in each FACS tube, centrifuged at 300xg for 5 min and resuspended in staining buffer. Fcγ receptors were blocked by incubation with 1 µg human IgG/$2.5 \times 10c4$ cells (JIR Cat. No. 009-000-003) in staining buffer for 20 min on ice. Cells were then mixed with 1.5 µl antibody/$2.5 \times 10c4$ cells for CD80 and CD163 detection whereas 5 µl antibody/2.5x10e4 cells for MHC class II detection was used: PE labeled mouse anti human CD163 (BD Bioscience Cat. No. 556018), PE labeled mouse anti human CD80 (BD Bioscience Cat. No. 557227) and Alexa 647 labeled mouse anti human MHC class II (Dako-Cat. No. M0775). The Alexa 647 label was conjugated to the antibody by using the Zenon Alexa 647 mouse IgG labeling kit (Invitrogen Cat. No. Z25008) After a I-hour incubation on ice cells were washed twice with staining buffer, resuspended and measured at a FACS Canto II.

Figure 1A:
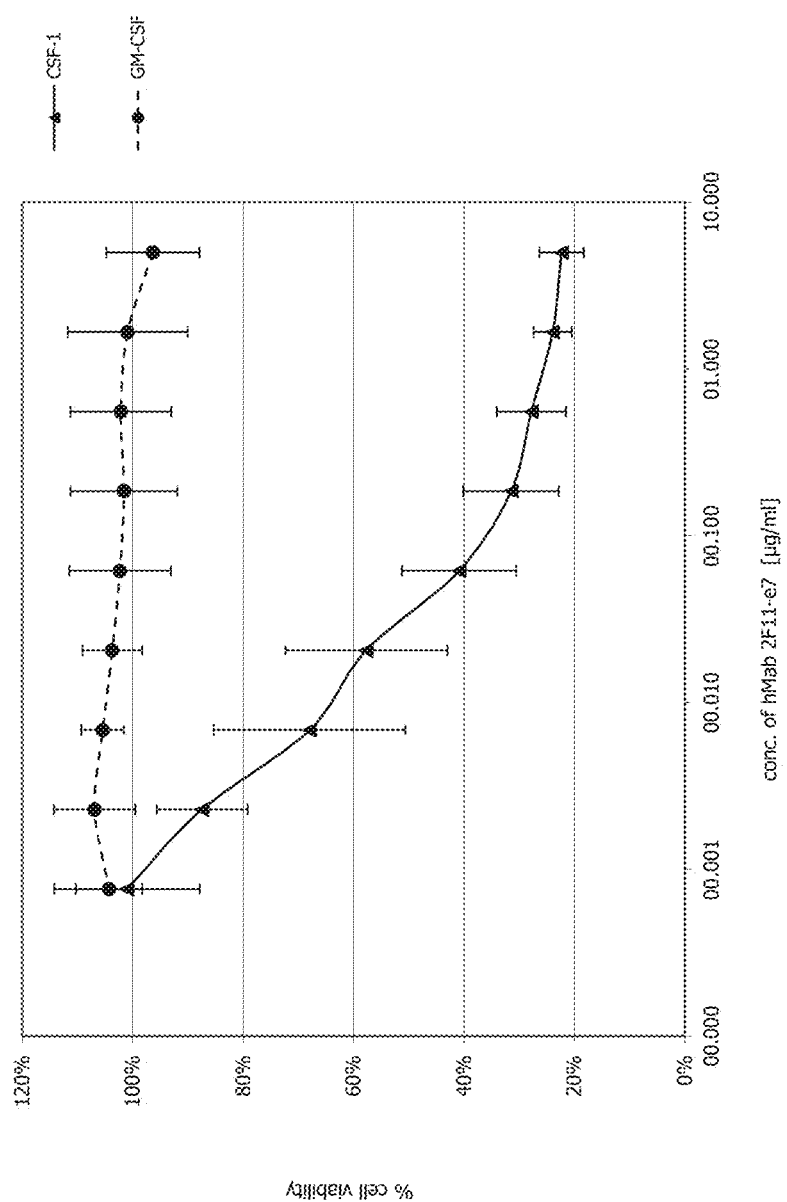
FIG. 1a-b 1a: Human Monocytes differentiated into macrophages with coculture of GM-CSF or CSF-1 (100 ng/ml ligand). After 6 days differentiation addition of hMab 2F11-7. Cell viability was measured at day 7 of antibody treatment in a CTG Viability Assay (CeliTiterGlo® Promega). Calculation of % cell viability: RLU signals from treated cells divided by RLU signal from untreated control without antibody, (n=4).
Figure 1B:
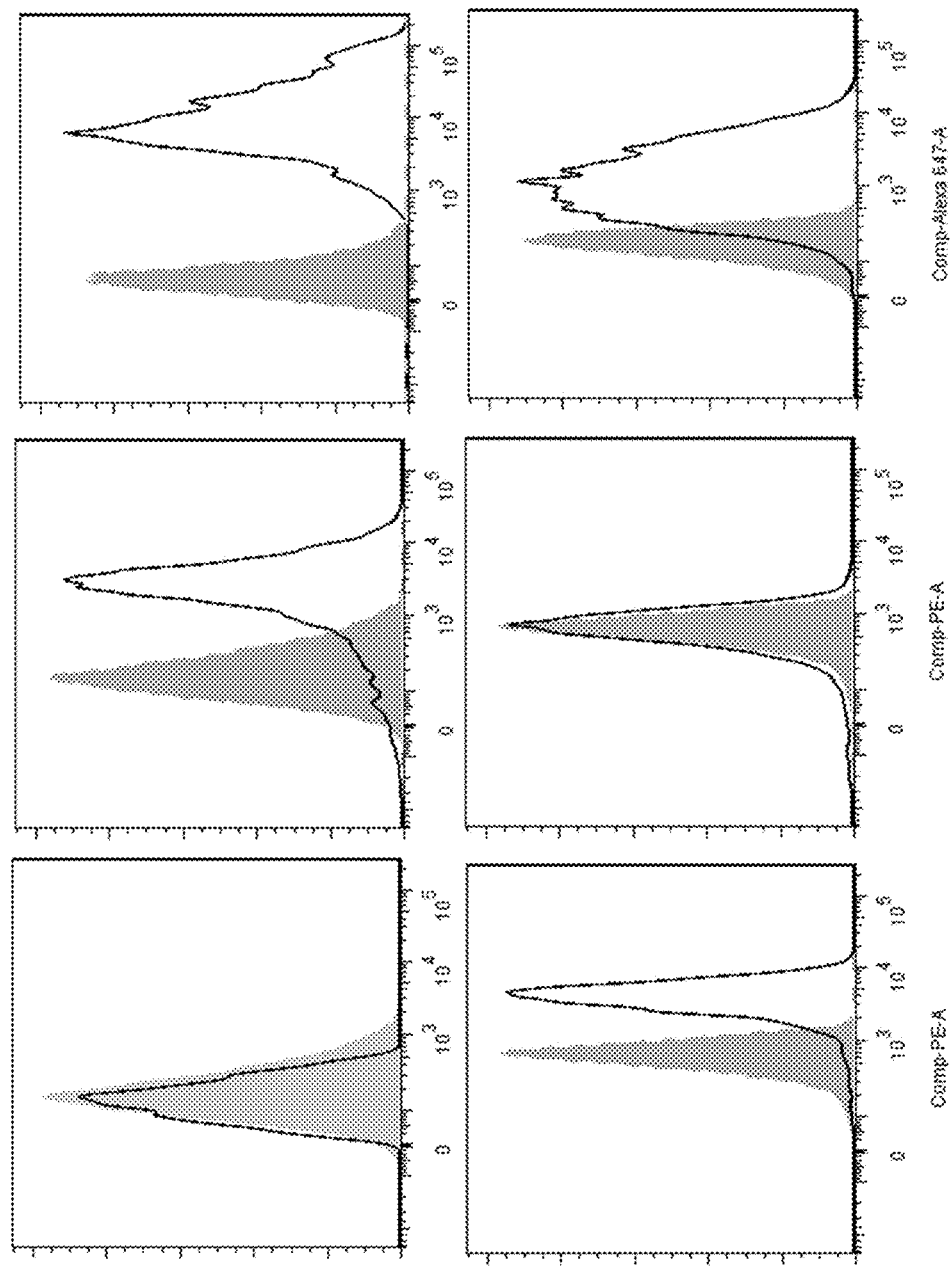
Figure 2A:
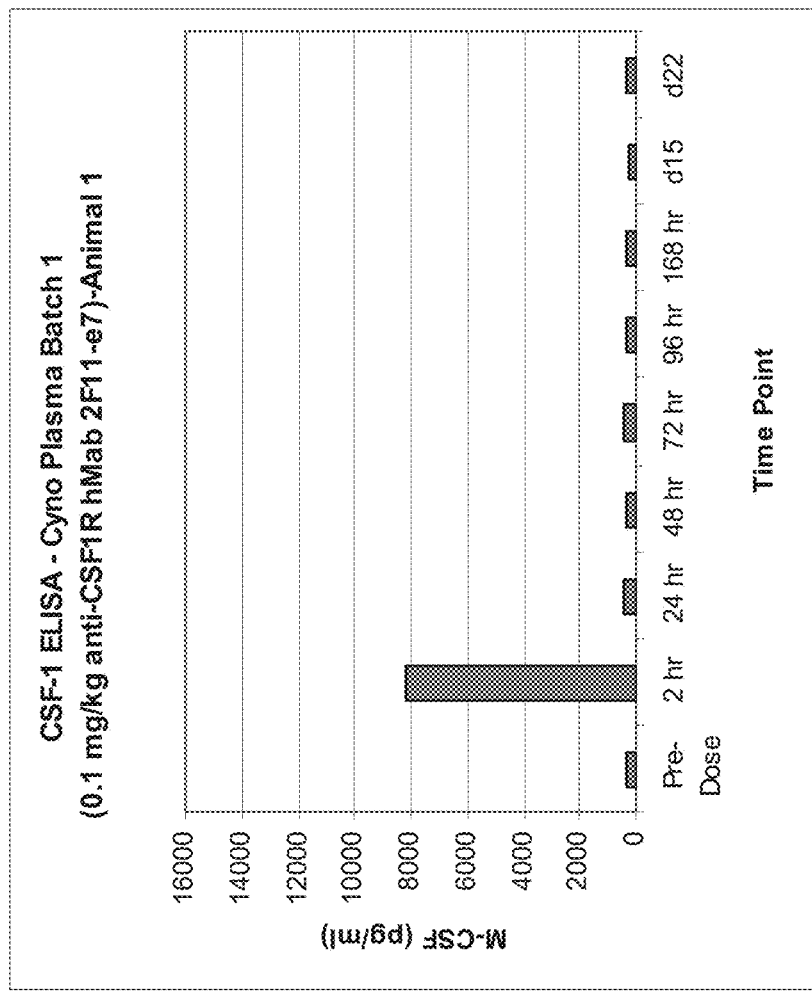
Figure 2B:
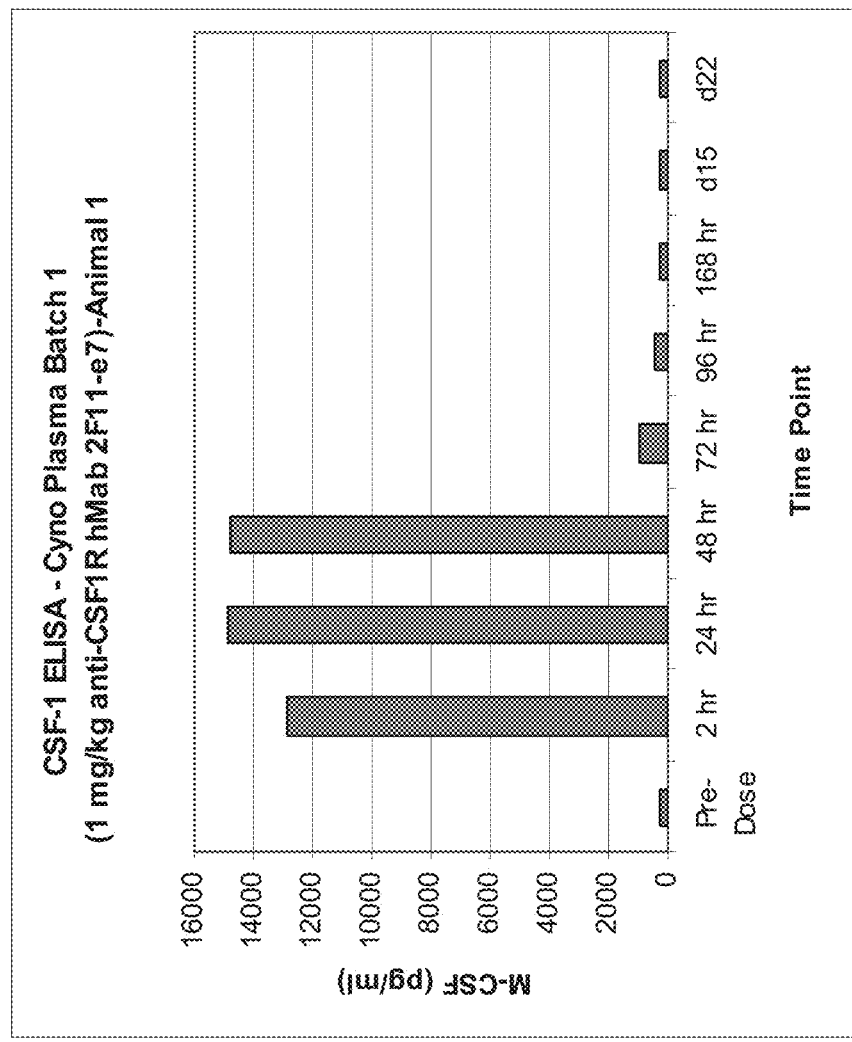
Figure 2C:
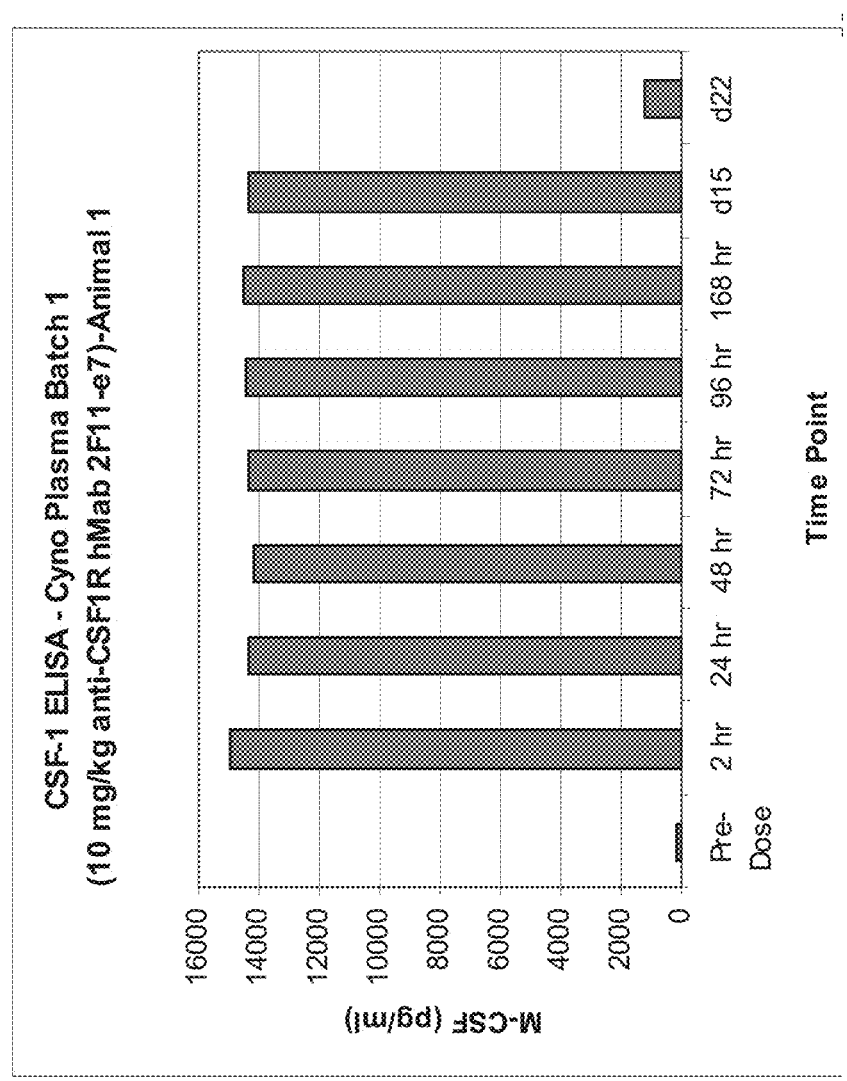
Figure 2D:
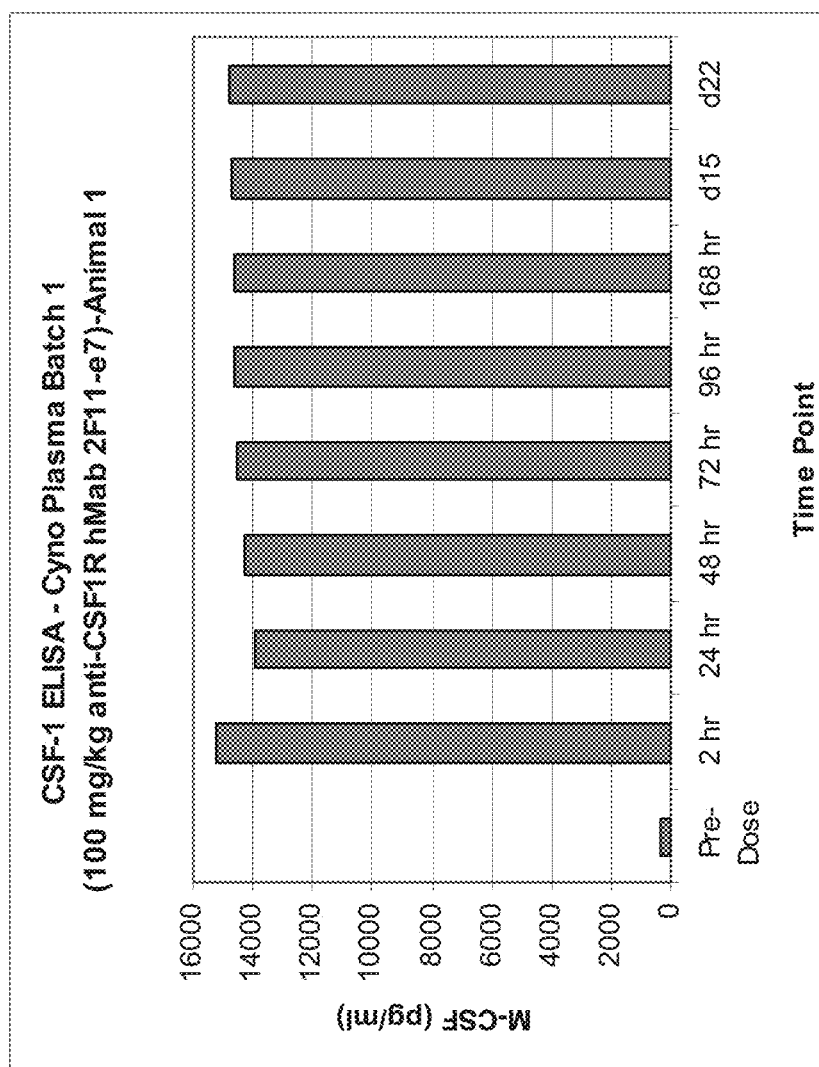

Exclusively M2 macrophage differentiation which is characterized by the expression of CD163, absence of CD80 and low MHC class II expression could be inhibited by addition of humanized anti-CSF-1R antibody hMab 2F11-e7. Furthermore, the M2 but not M1 macrophage survival is affected and could be analyzed by CellTiter-Glo® cell viability assay. Concentration dependent inhibition of the survival of macrophages by antibody treatment for 7 days is depicted in FIG. 1a. Expression of M1 and M2 macrophage markers assessed by flow cytometry is shown in FIG. 1b.

Example 6

CSF-1 Level Increase During CSF-1R Inhibition in Cynomolgus Monkey

Serum CSF-1 levels provide a pharmacodynamic marker of CSF-1R neutralizing activity of anti-human CSF-1R dimerization inhibitor hMab 2F11-e7. One male and one female cynomolgus monkey per dosage group (1 and 10 mg/kg) were intravenously administered anti-CSF1R antibody hMab 2F11-c7. Blood samples for analysis of CSF-1 levels were collected 1 week before treatment (pre-dose), 2, 24, 48, 72, 96, 168 hours post-dose and weekly for two additional weeks. CSF-levels were determined using a commercially available ELISA kit (Quantikine-human M-CSF) according to the manufacturer's instructions (R&D Systems, UK). Monkey CSF-1 level were determined by comparison with CSF-1 standard curve samples provided in the kit.

Administration of hMab 2F1 l-c7 induced a dramatic increase in CSF-1 by 1000-fold, which depending on the dose administered lasted for 48 hr (mg/kg) or 15 days (10 mg/kg). Hence, a dimerization inhibitor for CSF-1R offers the advantage to not directly compete with the dramatically upregulated ligand for binding to the receptor in contrast to a ligand displacing antibody. (Results are shown in FIG. 2)

Example 7

Relationship Between M2 Subtype Tumor Associated Macrophages (TAMs) and T Cells-Rationale for Combining Anti-CSF-1RI Antibody and a T Cell Engaging Agents To investigate the functional relationship between TAMs and T cells we isolated TAMs from the MC38 tumor and cocultured them with CD8+ T cells.

TAM Suppression Assay

TAMs were enriched from single cell suspensions of MC38 tumors after enzymatic digest using a two-step protocol: Single cells were stained with CD11b-FITC (clone M1/70) and positively enriched over MACS columns by anti-FITC beads (Miltenyi). Upon removal from the column, anti-FITC beads were detached using release buffer protocol as provided the manufacturer. Finally, TAM were isolated by adding anti-Ly6G and anti-Ly6C positive selection beads in order to remove granulocytic and monocytic cells from TAM preparations. Final cell purity was analyzed and was usually >90%. Subsequently, TAM were titrated in the indicated ratios to total CD3+ T cells labeled with CFSE in U-bottom plates coated with anti-CD3 and soluble anti-CD28 was added. Cell proliferation was determined from CFSElow cells using blank Sphero beads as previously described after 3 days of incubation (Hoves, S. et al. Monocyte-derived human macrophages mediate anergy in allogeneic T cells and induce regulatory T cells. J. Immunol. 177, 2691-2698 (2006)). In the presence of TAMs, T cell expansion induced by activation of CD3 and CD28 was suppressed. (see FIG. 3).

Example 8

Inhibition of Tumor Growth Under Treatment with Anti-CSF-1R Monoclonal Antibody in Combination with PD-L1 Antibody in Subcutaneous Syngeneic MC38 Colon Carcinoma Model Cells of the murine colorectal adenocarcinoma cell line MC38 (obtained from Beckman Research Institute of the City of Hope, Calif., USA) were cultured in Dulbecco's Modified Eagle Medium (DMEM, PAN Biotech) supplemented with 10% FCS and 2 mM L-glutamine at 37° C. in a water saturated atmosphere at 5% C02. At the day of inoculation, MC38 tumor cells were harvested with PBS from culture flasks and transferred into culture medium, centrifuged, washed once and re-suspended in PBS. For injection of cells, the final titer was adjusted to $1\times10^7$ cells/ml. Subsequently 100 µl of this suspension ($1\times10^6$ cells) were inoculated subcutaneously into 7-9 weeks old female C57BL/6N mice (obtained from Charles River, Sulzfeld, Germany). Treatment with control antibody (MOPC-21; Bio X Cell, West Lebanon), anti-murine CSF-1R mAb<mouse CSF1R> antibody at a weekly dose of 30 mg/kg i.p. alone or in combination with a mouse crossreactive anti PD-L1 antibody (10 mg/kg i.p., 6×q3d) started after tumors were established and had reached an average size of 100 mm. Tumor volume was measured twice a week and animal weights were monitored in parallel.

In first experiment monotherapy with <mouse CSF1R> antibody did not inhibit primary tumor growth when compared to control antibody treatment (IGI: 0%, TCR: 1.07 CI: 0.80-1.43, median time to progression >700 mm³: 21 days). Anti-PD-L1 monotherapy had an effect on MC38 primary tumor growth (TGI: 83%, TCR: 0.27 CI: 0.09-0.49, median time to progression >700 mm³: 32 days).

Addition of <mouse CSF1R> antibody to anti-PD-L1 therapy led to a slightly improved anti-tumor efficacy compared to anti-PD-L1 treatment alone (TGI: 83%, TCR: 0.28 CI: 0.09-0.51 median time to progression >700 mm³: 37 days) (see table below).

TABLE 6

Anti tumor Efficacy of <mouse anti-CSF1R> antibody/<anti-PD-L1> antibody combination in the MC38 mouse CRC in vivo model

| Group | TGI (day 21) | TCR (day 12) | 95% CI vs. group 1 | Median time to progression TV > 700 mm³ |
|---|---|---|---|---|
| Control (Mouse IgG1) | — | — | — | 21 |
| <mouse CSF1R> | 0% | 1.07 | (1.43-0.80) | 21 |
| <anti-PD-L1> | 83% | 0.27 | (0.49-0.09) | 32 |
| <mouse CSF1R>/<anti-PD-L1> | 83% | 0.28 | (0.51-0.09) | 37 |

Median time of progression >700 mm³ was 21 days for control (mouse IgG1) treated animals. Monotherapy with <mouse CSF1R> antibody did not inhibit primary tumor growth when compared to control antibody treatment (median time to progression >700 mm³: 21 days). Anti-PD-L1 monotherapy had an effect on MC38 primary tumor growth (median time to progression >700 mm³: 32 days). Addition of <mouse CSF1R> antibody to anti-PD-L1 therapy led to a slightly improved anti-tumor efficacy compared to PD-L1 treatment alone (median time to progression >700 mm³: 37 days) (see table below and FIG. 4).

TABLE 7

Anti tumor Efficacy of <mouse anti-CSF1R> antibody/<anti-PD-L1> antibody combination in the MC38 mouse CRC in vivo model (Median time to progression > 700 mm³)

| Group | Median time to progression TV > 700 mm³ |
|---|---|
| Control (Mouse IgG1) | 21 |
| <mouse CSF1R> | 21 |
| <anti-PD-L1> | 32 |
| <mouse CSF1R>/<anti-PD-L1> | 37 |

In analogous experiments, but starting treatment at different tumor sizes (e.g. starting treatment when the tumor has reached a volume above and below 100 mm; (different groups are evaluated) and in a further experiment also using different anti PD-L1 antibodies described in table 2, the inhibition of tumor growth under treatment with anti-CSF-1R monoclonal antibody in combination with anti-PD-L1 antibody in subcutaneous syngeneic MC38 colon carcinoma model is evaluated.

Example 9

Inhibition of Tumor Growth Under Treatment with Anti-CSF-1R Monoclonal Antibody in Combination with PD-L1 Antibody in Subcutaneous Syngeneic CT26.WT Colon Carcinoma Model Cells of the murine colorectal adenocarcinoma cell line CT26.WT tumor cells (obtained from ATCC) were cultured in Dulbecco's Modified Eagle Medium (DMEM, PAN Biotech) supplemented with 10% FCS and 2 mM L-glutamine at 37° C. in a water saturated atmosphere at 5% CO2. At the day of inoculation, CT26.WT tumor cells were harvested with PBS from culture flasks and transferred into culture medium, centrifuged, washed once and re-suspended in PBS. For injection of cells, the final titer was adjusted to $1\times10^7$ cells/ml. Subsequently 100 µl of this suspension ($1\times10^6$ cells) were inoculated subcutaneously into 11-13 weeks old female Balb/c mice (obtained from Charles River, Sulzfeld, Germany). Treatment with control antibody (MOPC-21; Bio X Cell, West Lebanon), anti-murine CSF-1R mAb<mouse CSF1R> antibody at a weekly dose of 30 mg/kg i.p. alone or in combination with a mouse crossreactive anti PD-L1 antibody (10 mg/kg i.p., 6×q3d) started after tumors were established and had reached an average size of 150 mm³. While treatment in monotherapy groups started on day 9 after tumor cell inoculation, treatment in combination group was sequential (day 9: start of treatment with anti-murine CSF-1R mAb; day 11: start of treatment with anti PD-L1 antibody). Tumor volume was measured twice a week and animal weights were monitored in parallel. Results are shown in Figure Median time to progression ≥700 mm3 was 17 days for IgG control treatment group, 16 days for <mouse anti-CSF1R> antibody monotherapy group, 18 days for <anti-PD-L1> antibody monotherapy group and 18 days for <mouse anti-CSF1R>/<anti-PD-L1> antibody combination group.

While all animals in control or monotherapy groups needed to be terminated due to progressive tumor burden one animal of the <mouse anti-CSF1R>/<anti-PD-L1> antibody combination group experienced tumor shrinkage and remained tumor-free until study termination on day 79 after tumor inoculation.

The invention claimed is:

1. A method for treating colon cancer, the method comprising administering to a patient in need thereof an effective amount of an antibody which binds to human colony stimulating factor 1 receptor (CSF-1R), and an antibody which binds to human programmed death-ligand 1 (PD-L1), wherein the antibody which binds to human CSF-1R comprises:
   a) a heavy chain variable domain VH of SEQ ID NO:23 and a light chain variable domain VL of SEQ ID NO:24, or
   b) a heavy chain variable domain VH of SEQ ID NO:31 and a light chain variable domain VL of SEQ ID NO:32, or
   c) a heavy chain variable domain VH of SEQ ID NO:39 and a light chain variable domain VL of SEQ ID NO:40, or
   d) a heavy chain variable domain VH of SEQ ID NO:47 and a light chain variable domain VL of SEQ ID NO:48, or
   e) a heavy chain variable domain VH of SEQ ID NO:55 and a light chain variable domain VL of SEQ ID NO:56.

2. A method of:
   i) inhibiting cell proliferation in CSF-1R ligand-dependent and/or CSF-1 ligand-independent CSF-1R-expressing tumor cells; or
   ii) inhibiting cell proliferation of tumors with CSF-1R ligand-dependent and/or CSF-1R ligand-independent CSF-1R-expressing macrophage infiltrate,
   the method comprising administering to a patient in need thereof an effective amount of an antibody which binds to human colony stimulating factor 1 receptor (CSF-1R), and an antibody which binds to human programmed death-ligand 1 (PD-L1), wherein the antibody which binds to human CSF-1R comprises:
   a) a heavy chain variable domain VH of SEQ ID NO:23 and a light chain variable domain VL of SEQ ID NO:24, or
   b) a heavy chain variable domain VH of SEQ ID NO:31 and a light chain variable domain VL of SEQ ID NO:32, or
   c) a heavy chain variable domain VH of SEQ ID NO:39 and a light chain variable domain VL of SEQ ID NO:40, or
   d) a heavy chain variable domain VH of SEQ ID NO:47 and a light chain variable domain VL of SEQ ID NO:48, or
   e) a heavy chain variable domain VH of SEQ ID NO:55 and a light chain variable domain VL of SEQ ID NO:56.

3. A method of inhibiting a CSF-1R-expressing tumor or inhibiting a tumor with CSF-1R-expressing macrophage infiltrate in a patient suffering from cancer, wherein the tumor expresses increased levels of CSF-1R ligand, the method comprising administering to the patient an effective amount of an antibody which binds to human colony stimulating factor 1 receptor (CSF-1R), and an antibody which binds to human programmed death-ligand 1 (PD-L1), wherein the antibody which binds to human CSF-1R comprises:
   a) a heavy chain variable domain VH of SEQ ID NO:23 and a light chain variable domain VL of SEQ ID NO:24, or
   b) a heavy chain variable domain VH of SEQ ID NO:31 and a light chain variable domain VL of SEQ ID NO:32, or
   c) a heavy chain variable domain VH of SEQ ID NO:39 and a light chain variable domain VL of SEQ ID NO:40, or
   d) a heavy chain variable domain VH of SEQ ID NO:47 and a light chain variable domain VL of SEQ ID NO:48, or
   e) a heavy chain variable domain VH of SEQ ID NO:55 and a light chain variable domain VL of SEQ ID NO:56.

4. The method of claim 1, wherein said antibody which binds to human CSF-1R and said antibody which binds to human PD-L1 are human IgG1 subclass or human IgG4 subclass.

5. The method of claim 1, wherein said antibody which binds to human CSF-1R and said antibody which binds to human PD-L1 comprise an effectorless Fc mutation, wherein the effectorless Fc mutation is L234A/L235A or L234A/L235A/P329G or N297A or D265A/N297A, wherein the numbering is according to EU numbering convention, and wherein the Fc is a human IgG Fc.

6. The method of claim 1, wherein the antibody which binds to human PD-L1 comprises a heavy chain variable domain and a light chain variable domain, and wherein the heavy chain variable domain comprises the three complementarity determining regions (CDRs) of the heavy chain variable domain VH of SEQ ID NO:89 and the light chain variable domain comprises the three complementarity determining regions (CDRs) of the light chain variable domain VL of SEQ ID NO:92.

7. The method of claim 1, wherein the antibody which binds to human CSF-1R comprises a heavy chain variable domain VH of SEQ ID NO:39 and a light chain variable domain VL of SEQ ID NO:40.

8. The method of claim 1, wherein the antibody which binds to human CSF-1R comprises a heavy chain variable domain VH of SEQ ID NO:39 and a light chain variable domain VL of SEQ ID NO:40; and the antibody which binds to human PD-L1 comprises a heavy chain variable domain and a light chain variable domain, wherein the heavy chain variable domain comprises the three complementarity determining regions (CDRs) of the heavy chain variable domain VH of SEQ ID NO:89 and the light chain variable domain comprises the three complementarity determining regions (CDRs) of the light chain variable domain VL of SEQ ID NO:92.

9. The method of claim 2, wherein the antibody which binds to human PD-L1 comprises a heavy chain variable domain and a light chain variable domain, and wherein the heavy chain variable domain comprises the three complementarity determining regions (CDRs) of the heavy chain variable domain VH of SEQ ID NO:89 and the light chain variable domain comprises the three complementarity determining regions (CDRs) of the light chain variable domain VL of SEQ ID NO:92.

10. The method of claim 2, wherein the antibody which binds to human CSF-1R comprises a heavy chain variable domain VH of SEQ ID NO:39 and a light chain variable domain VL of SEQ ID NO:40.

11. The method of claim 2, wherein the antibody which binds to human CSF-1R comprises a heavy chain variable domain VH of SEQ ID NO:39 and a light chain variable domain VL of SEQ ID NO:40; and the antibody which binds to human PD-L1 comprises a heavy chain variable domain and a light chain variable domain, wherein the heavy chain variable domain comprises the three complementarity determining regions (CDRs) of the heavy chain variable domain VH of SEQ ID NO:89 and the light chain variable domain comprises the three complementarity determining regions (CDRs) of the light chain variable domain VL of SEQ ID NO:92.

12. The method of claim 3, wherein the antibody which binds to human PD-L1 comprises a heavy chain variable domain and a light chain variable domain, and wherein the heavy chain variable domain comprises the three complementarity determining regions (CDRs) of the heavy chain variable domain VH of SEQ ID NO:89 and the light chain variable domain comprises the three complementarity determining regions (CDRs) of the light chain variable domain VL of SEQ ID NO:92.

13. The method of claim 3, wherein the antibody which binds to human CSF-1R comprises a heavy chain variable domain VH of SEQ ID NO:39 and a light chain variable domain VL of SEQ ID NO:40.

14. The method of claim 3, wherein the antibody which binds to human CSF-1R comprises a heavy chain variable domain VH of SEQ ID NO:39 and a light chain variable domain VL of SEQ ID NO:40; and the antibody which binds to human PD-L1 comprises a heavy chain variable domain and a light chain variable domain, wherein the heavy chain variable domain comprises the three complementarity determining regions (CDRs) of the heavy chain variable domain VH of SEQ ID NO:89 and the light chain variable domain comprises the three complementarity determining regions (CDRs) of the light chain variable domain VL of SEQ ID NO:92.

* * * * *

SEQUENCE LISTING

<160> NUMBER OF SEQ ID NOS: 107

<210> SEQ ID NO 1
<211> LENGTH: 8
<212> TYPE: PRT
<213> ORGANISM: Mus musculus

<400> SEQUENCE: 1

Asp Gln Arg Leu Tyr Phe Asp Val
1               5

<210> SEQ ID NO 2
<211> LENGTH: 16
<212> TYPE: PRT
<213> ORGANISM: Mus musculus

<400> SEQUENCE: 2

Val Ile Trp Thr Asp Gly Gly Thr Asn Tyr Asn Ser Pro Phe Met Ser
1               5                   10                  15

<210> SEQ ID NO 3
<211> LENGTH: 5
<212> TYPE: PRT
<213> ORGANISM: Mus musculus

<400> SEQUENCE: 3

Thr Tyr Asp Ile Ser
1               5

<210> SEQ ID NO 4
<211> LENGTH: 8
<212> TYPE: PRT
<213> ORGANISM: Mus musculus

<400> SEQUENCE: 4

Gly Gln Ser Phe Ser Tyr Pro Thr
1               5

<210> SEQ ID NO 5
<211> LENGTH: 7
<212> TYPE: PRT
<213> ORGANISM: Mus musculus

<400> SEQUENCE: 5

Gly Ala Ser Asn Arg Tyr Thr
1               5

<210> SEQ ID NO 6
<211> LENGTH: 11
<212> TYPE: PRT
<213> ORGANISM: Mus musculus

<400> SEQUENCE: 6

Lys Ala Ser Glu Asp Val Asn Thr Tyr Val Ser
1               5                   10

<210> SEQ ID NO 7
<211> LENGTH: 116
<212> TYPE: PRT
<213> ORGANISM: Mus musculus

<400> SEQUENCE: 7

Gln Val Gln Leu Lys Glu Ser Gly Pro Gly Leu Val Ala Pro Ser Gln
1               5                   10                  15

```
Ser Leu Ser Ile Thr Cys Thr Val Ser Gly Phe Ser Leu Thr Thr Tyr
            20                  25                  30

Asp Ile Ser Trp Ile Arg Gln Ser Pro Gly Lys Gly Leu Glu Trp Leu
            35                  40                  45

Gly Val Ile Trp Thr Asp Gly Gly Thr Asn Tyr Asn Ser Pro Phe Met
 50                  55                  60

Ser Arg Leu Ser Ile Arg Lys Asp Asn Ser Lys Ser Gln Val Phe Leu
 65                  70                  75                  80

Lys Met Asn Arg Leu Gln Thr Asp Thr Ala Ile Tyr Tyr Cys Val
            85                  90                  95

Arg Asp Gln Arg Leu Tyr Phe Asp Val Trp Gly Ala Gly Thr Thr Val
            100                 105                 110

Thr Val Ser Ser
        115

<210> SEQ ID NO 8
<211> LENGTH: 106
<212> TYPE: PRT
<213> ORGANISM: Mus musculus

<400> SEQUENCE: 8

Asn Ile Val Met Thr Gln Ser Pro Lys Ser Met Ser Met Ser Val Gly
 1               5                  10                  15

Glu Arg Val Thr Leu Asn Cys Lys Ala Ser Glu Asp Val Asn Thr Tyr
            20                  25                  30

Val Ser Trp Tyr Gln Gln Pro Glu Gln Ser Pro Lys Leu Leu Ile
            35                  40                  45

Tyr Gly Ala Ser Asn Arg Tyr Thr Gly Val Pro Asp Arg Phe Thr Gly
 50                  55                  60

Gly Gly Ser Thr Thr Asp Phe Thr Leu Thr Ile Ser Ser Val Gln Ala
 65                  70                  75                  80

Glu Asp Leu Ala Asp Tyr Phe Cys Gly Gln Ser Phe Ser Tyr Pro Thr
            85                  90                  95

Phe Gly Thr Gly Thr Lys Leu Glu Ile Lys
            100                 105

<210> SEQ ID NO 9
<211> LENGTH: 7
<212> TYPE: PRT
<213> ORGANISM: Mus musculus

<400> SEQUENCE: 9

Asp Pro Arg Leu Tyr Phe Asp
 1               5

<210> SEQ ID NO 10
<211> LENGTH: 16
<212> TYPE: PRT
<213> ORGANISM: Mus musculus

<400> SEQUENCE: 10

Val Ile Trp Thr Gly Gly Gly Thr Asn Tyr Asn Ser Gly Phe Met Ser
 1               5                  10                  15

<210> SEQ ID NO 11
<211> LENGTH: 5
<212> TYPE: PRT
<213> ORGANISM: Mus musculus

<400> SEQUENCE: 11
```

Ser Phe Asp Ile Ser
1               5

<210> SEQ ID NO 12
<211> LENGTH: 8
<212> TYPE: PRT
<213> ORGANISM: Mus musculus

<400> SEQUENCE: 12

Gly Gln Thr Phe Ser Tyr Pro Thr
1               5

<210> SEQ ID NO 13
<211> LENGTH: 7
<212> TYPE: PRT
<213> ORGANISM: Mus musculus

<400> SEQUENCE: 13

Gly Ala Ser Asn Arg Tyr Thr
1               5

<210> SEQ ID NO 14
<211> LENGTH: 11
<212> TYPE: PRT
<213> ORGANISM: Mus musculus

<400> SEQUENCE: 14

Lys Ala Ser Glu Asp Val Val Thr Tyr Val Ser
1               5                   10

<210> SEQ ID NO 15
<211> LENGTH: 116
<212> TYPE: PRT
<213> ORGANISM: Mus musculus

<400> SEQUENCE: 15

Gln Val Gln Leu Lys Glu Ser Gly Pro Gly Leu Val Ala Pro Ser Lys
1               5                   10                  15

Ser Leu Ser Ile Thr Cys Thr Val Ser Gly Ser Ser Leu Asp Ser Phe
            20                  25                  30

Asp Ile Ser Trp Ile Arg Gln Ser Pro Gly Lys Gly Leu Glu Trp Leu
        35                  40                  45

Gly Val Ile Trp Thr Gly Gly Gly Thr Asn Tyr Asn Ser Gly Phe Met
    50                  55                  60

Ser Arg Leu Arg Ile Thr Lys Asp Asn Ser Lys Ser Gln Val Leu Leu
65                  70                  75                  80

Lys Met Asn Ser Leu Gln Ser Asp Asp Thr Ala Ile Tyr Tyr Cys Val
                85                  90                  95

Arg Asp Pro Arg Leu Tyr Phe Asp Val Trp Gly Ala Gly Thr Thr Val
            100                 105                 110

Thr Val Ser Ser
        115

<210> SEQ ID NO 16
<211> LENGTH: 106
<212> TYPE: PRT
<213> ORGANISM: Mus musculus

<400> SEQUENCE: 16

Asn Ile Val Met Thr Gln Ser Pro Lys Ser Met Ser Met Ser Val Gly
1               5                   10                  15

```
Glu Arg Val Thr Leu Ser Cys Lys Ala Ser Glu Asp Val Val Thr Tyr
            20                  25                  30

Val Ser Trp Tyr Gln Gln Lys Pro Asp Gln Ser Pro Lys Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Ser Ser Val Gln Ala
65                  70                  75                  80

Glu Asp Leu Ala Asp Tyr Tyr Cys Gly Gln Thr Phe Ser Tyr Pro Thr
                85                  90                  95

Phe Gly Thr Gly Thr Lys Leu Glu Ile Lys
            100                 105

<210> SEQ ID NO 17
<211> LENGTH: 8
<212> TYPE: PRT
<213> ORGANISM: Artificial
<220> FEATURE:
<223> OTHER INFORMATION: heavy chain CDR3, hMab 2F11-c11

<400> SEQUENCE: 17

Asp Gln Arg Leu Tyr Phe Asp Val
1               5

<210> SEQ ID NO 18
<211> LENGTH: 16
<212> TYPE: PRT
<213> ORGANISM: Artificial
<220> FEATURE:
<223> OTHER INFORMATION: heavy chain CDR2, hMab 2F11-c11

<400> SEQUENCE: 18

Val Ile Trp Thr Asp Gly Gly Thr Asn Tyr Asn Ser Pro Phe Met Ser
1               5                   10                  15

<210> SEQ ID NO 19
<211> LENGTH: 5
<212> TYPE: PRT
<213> ORGANISM: Artificial
<220> FEATURE:
<223> OTHER INFORMATION: heavy chain CDR1, hMab 2F11-c11

<400> SEQUENCE: 19

Thr Tyr Asp Ile Ser
1               5

<210> SEQ ID NO 20
<211> LENGTH: 8
<212> TYPE: PRT
<213> ORGANISM: Artificial
<220> FEATURE:
<223> OTHER INFORMATION: light chain CDR3, hMab 2F11-c11

<400> SEQUENCE: 20

Gly Gln Ser Phe Ser Tyr Pro Thr
1               5

<210> SEQ ID NO 21
<211> LENGTH: 7
<212> TYPE: PRT
<213> ORGANISM: Artificial
<220> FEATURE:
<223> OTHER INFORMATION: light chain CDR2, hMab 2F11-c11
```

```
<400> SEQUENCE: 21

Gly Ala Ser Asn Arg Tyr Thr
1               5

<210> SEQ ID NO 22
<211> LENGTH: 11
<212> TYPE: PRT
<213> ORGANISM: Artificial
<220> FEATURE:
<223> OTHER INFORMATION: light chain CDR1, hMab 2F11-c11

<400> SEQUENCE: 22

Arg Ala Ser Glu Asp Val Asn Thr Tyr Val Ser
1               5                   10

<210> SEQ ID NO 23
<211> LENGTH: 116
<212> TYPE: PRT
<213> ORGANISM: Artificial
<220> FEATURE:
<223> OTHER INFORMATION: heavy chain variable domain, hMab 2F11-c11

<400> SEQUENCE: 23

Gln Val Gln Leu Val Gln Ser Gly Ala Glu Val Lys Lys Pro Gly Ser
1               5                   10                  15

Ser Val Lys Val Ser Cys Lys Ala Ser Gly Phe Ser Leu Thr Thr Tyr
            20                  25                  30

Asp Ile Ser Trp Ile Arg Gln Ala Pro Gly Gln Gly Leu Glu Trp Met
        35                  40                  45

Gly Val Ile Trp Thr Asp Gly Gly Thr Asn Tyr Asn Ser Pro Phe Met
    50                  55                  60

Ser Arg Val Thr Ile Thr Lys Asp Glu Ser Thr Ser Thr Ala Tyr Met
65                  70                  75                  80

Glu Leu Ser Ser Leu Arg Ser Glu Asp Thr Ala Val Tyr Tyr Cys Val
                85                  90                  95

Arg Asp Gln Arg Leu Tyr Phe Asp Val Trp Gly Gln Gly Thr Thr Val
            100                 105                 110

Thr Val Ser Ser
        115

<210> SEQ ID NO 24
<211> LENGTH: 106
<212> TYPE: PRT
<213> ORGANISM: Artificial
<220> FEATURE:
<223> OTHER INFORMATION: light chain variable domain, hMab 2F11-c11

<400> SEQUENCE: 24

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asp Val Asn Thr Tyr
            20                  25                  30

Val Ser Trp Tyr Gln Gln Lys Pro Gly Lys Ala Pro Lys Leu Leu Ile
        35                  40                  45

Tyr Gly Ala Ser Asn Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gly Gln Ser Phe Ser Tyr Pro Thr
                85                  90                  95
```

Phe Gly Gln Gly Thr Lys Leu Glu Ile Lys
            100                 105

<210> SEQ ID NO 25
<211> LENGTH: 8
<212> TYPE: PRT
<213> ORGANISM: Artificial
<220> FEATURE:
<223> OTHER INFORMATION: heavy chain CDR3, hMab 2F11-d8

<400> SEQUENCE: 25

Asp Gln Arg Leu Tyr Phe Asp Val
1               5

<210> SEQ ID NO 26
<211> LENGTH: 16
<212> TYPE: PRT
<213> ORGANISM: Artificial
<220> FEATURE:
<223> OTHER INFORMATION: heavy chain CDR2, hMab 2F11-d8

<400> SEQUENCE: 26

Val Ile Trp Thr Asp Gly Gly Ala Asn Tyr Ala Gln Lys Phe Gln Gly
1               5                   10                  15

<210> SEQ ID NO 27
<211> LENGTH: 5
<212> TYPE: PRT
<213> ORGANISM: Artificial
<220> FEATURE:
<223> OTHER INFORMATION: heavy chain CDR1, hMab 2F11-d8

<400> SEQUENCE: 27

Thr Tyr Asp Ile Ser
1               5

<210> SEQ ID NO 28
<211> LENGTH: 8
<212> TYPE: PRT
<213> ORGANISM: Artificial
<220> FEATURE:
<223> OTHER INFORMATION: light chain CDR3, hMab 2F11-d8

<400> SEQUENCE: 28

Gly Gln Ser Phe Ser Tyr Pro Thr
1               5

<210> SEQ ID NO 29
<211> LENGTH: 7
<212> TYPE: PRT
<213> ORGANISM: Artificial
<220> FEATURE:
<223> OTHER INFORMATION: light chain CDR2, hMab 2F11-d8

<400> SEQUENCE: 29

Gly Ala Ser Asn Arg Tyr Thr
1               5

<210> SEQ ID NO 30
<211> LENGTH: 11
<212> TYPE: PRT
<213> ORGANISM: Artificial
<220> FEATURE:
<223> OTHER INFORMATION: light chain CDR1, hMab 2F11-d8

<400> SEQUENCE: 30

Lys Ala Ser Glu Asp Val Asn Thr Tyr Val Ser
1               5                   10

<210> SEQ ID NO 31
<211> LENGTH: 116
<212> TYPE: PRT
<213> ORGANISM: Artificial
<220> FEATURE:
<223> OTHER INFORMATION: heavy chain variable domain, hMab 2F11-d8

<400> SEQUENCE: 31

Gln Val Gln Leu Val Gln Ser Gly Ala Glu Val Lys Lys Pro Gly Ser
1               5                   10                  15

Ser Val Lys Val Ser Cys Lys Ala Ser Gly Phe Ser Leu Thr Thr Tyr
            20                  25                  30

Asp Ile Ser Trp Val Arg Gln Ala Pro Gly Gln Gly Leu Glu Trp Met
        35                  40                  45

Gly Val Ile Trp Thr Asp Gly Gly Ala Asn Tyr Ala Gln Lys Phe Gln
    50                  55                  60

Gly Arg Val Thr Ile Thr Ala Asp Glu Ser Thr Ser Thr Ala Tyr Met
65                  70                  75                  80

Glu Leu Ser Ser Leu Arg Ser Glu Asp Thr Ala Val Tyr Tyr Cys Ala
                85                  90                  95

Arg Asp Gln Arg Leu Tyr Phe Asp Val Trp Gly Gln Gly Thr Thr Val
            100                 105                 110

Thr Val Ser Ser
        115

<210> SEQ ID NO 32
<211> LENGTH: 106
<212> TYPE: PRT
<213> ORGANISM: Artificial
<220> FEATURE:
<223> OTHER INFORMATION: light chain variable domain, hMab 2F11-d8

<400> SEQUENCE: 32

Asp Ile Gln Met Thr Gln Ser Pro Ser Ser Leu Ser Ala Ser Val Gly
1               5                   10                  15

Asp Arg Val Thr Ile Thr Cys Lys Ala Ser Glu Asp Val Asn Thr Tyr
            20                  25                  30

Val Ser Trp Tyr Gln Gln Lys Pro Gly Lys Ala Pro Lys Leu Leu Ile
        35                  40                  45

Tyr Gly Ala Ser Asn Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gly Gln Ser Phe Ser Tyr Pro Thr
                85                  90                  95

Phe Gly Gln Gly Thr Lys Leu Glu Ile Lys
            100                 105

<210> SEQ ID NO 33
<211> LENGTH: 8
<212> TYPE: PRT
<213> ORGANISM: Artificial
<220> FEATURE:
<223> OTHER INFORMATION: heavy chain CDR3, hMab 2F11-e7

<400> SEQUENCE: 33

Asp Gln Arg Leu Tyr Phe Asp Val

```
<210> SEQ ID NO 34
<211> LENGTH: 16
<212> TYPE: PRT
<213> ORGANISM: Artificial
<220> FEATURE:
<223> OTHER INFORMATION: heavy chain CDR2, hMab 2F11-e7

<400> SEQUENCE: 34

Val Ile Trp Thr Asp Gly Gly Thr Asn Tyr Ala Gln Lys Leu Gln Gly
1               5                   10                  15

<210> SEQ ID NO 35
<211> LENGTH: 5
<212> TYPE: PRT
<213> ORGANISM: Artificial
<220> FEATURE:
<223> OTHER INFORMATION: heavy chain CDR1, hMab 2F11-e7

<400> SEQUENCE: 35

Ser Tyr Asp Ile Ser
1               5

<210> SEQ ID NO 36
<211> LENGTH: 8
<212> TYPE: PRT
<213> ORGANISM: Artificial
<220> FEATURE:
<223> OTHER INFORMATION: light chain CDR3, hMab 2F11-e7

<400> SEQUENCE: 36

Gln Gln Ser Phe Ser Tyr Pro Thr
1               5

<210> SEQ ID NO 37
<211> LENGTH: 7
<212> TYPE: PRT
<213> ORGANISM: Artificial
<220> FEATURE:
<223> OTHER INFORMATION: light chain CDR2, hMab 2F11-e7

<400> SEQUENCE: 37

Ala Ala Ser Asn Arg Tyr Thr
1               5

<210> SEQ ID NO 38
<211> LENGTH: 11
<212> TYPE: PRT
<213> ORGANISM: Artificial
<220> FEATURE:
<223> OTHER INFORMATION: light chain CDR1, hMab 2F11-e7

<400> SEQUENCE: 38

Arg Ala Ser Glu Asp Val Asn Thr Tyr Val Ser
1               5                   10

<210> SEQ ID NO 39
<211> LENGTH: 116
<212> TYPE: PRT
<213> ORGANISM: Artificial
<220> FEATURE:
<223> OTHER INFORMATION: heavy chain variable domain, hMab 2F11-e7

<400> SEQUENCE: 39

Gln Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Thr Phe Thr Ser Tyr
            20                  25                  30

Asp Ile Ser Trp Val Arg Gln Ala Pro Gly Gln Gly Leu Glu Trp Met
        35                  40                  45

Gly Val Ile Trp Thr Asp Gly Gly Thr Asn Tyr Ala Gln Lys Leu Gln
 50                  55                  60

Gly Arg Val Thr Met Thr Thr Asp Thr Ser Thr Ser Thr Ala Tyr Met
 65                  70                  75                  80

Glu Leu Arg Ser Leu Arg Ser Asp Asp Thr Ala Val Tyr Tyr Cys Ala
                85                  90                  95

Arg Asp Gln Arg Leu Tyr Phe Asp Val Trp Gly Gln Gly Thr Thr Val
            100                 105                 110

Thr Val Ser Ser
        115

<210> SEQ ID NO 40
<211> LENGTH: 106
<212> TYPE: PRT
<213> ORGANISM: Artificial
<220> FEATURE:
<223> OTHER INFORMATION: light chain variable domain, hMab 2F11-e7

<400> SEQUENCE: 40

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asp Val Asn Thr Tyr
            20                  25                  30

Val Ser Trp Tyr Gln Gln Lys Pro Gly Lys Ala Pro Lys Leu Leu Ile
        35                  40                  45

Tyr Ala Ala Ser Asn Arg Tyr Thr Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Phe Ser Tyr Pro Thr
                85                  90                  95

Phe Gly Gln Gly Thr Lys Leu Glu Ile Lys
            100                 105

<210> SEQ ID NO 41
<211> LENGTH: 8
<212> TYPE: PRT
<213> ORGANISM: Artificial
<220> FEATURE:
<223> OTHER INFORMATION: heavy chain CDR3, hMab 2F11-f12

<400> SEQUENCE: 41

Asp Gln Arg Leu Tyr Phe Asp Val
1               5

<210> SEQ ID NO 42
<211> LENGTH: 16
<212> TYPE: PRT
<213> ORGANISM: Artificial
<220> FEATURE:
<223> OTHER INFORMATION: heavy chain CDR2, hMab 2F11-f12

<400> SEQUENCE: 42

Val Ile Trp Thr Asp Gly Gly Thr Asn Tyr Asn Ser Pro Phe Met Ser
1               5                   10                  15
```

```
<210> SEQ ID NO 43
<211> LENGTH: 5
<212> TYPE: PRT
<213> ORGANISM: Artificial
<220> FEATURE:
<223> OTHER INFORMATION: heavy chain CDR1, hMab 2F11-f12

<400> SEQUENCE: 43

Thr Tyr Asp Ile Ser
1               5

<210> SEQ ID NO 44
<211> LENGTH: 8
<212> TYPE: PRT
<213> ORGANISM: Artificial
<220> FEATURE:
<223> OTHER INFORMATION: light chain CDR3, hMab 2F11-f12

<400> SEQUENCE: 44

Gly Gln Ser Phe Ser Tyr Pro Thr
1               5

<210> SEQ ID NO 45
<211> LENGTH: 7
<212> TYPE: PRT
<213> ORGANISM: Artificial
<220> FEATURE:
<223> OTHER INFORMATION: light chain CDR2, hMab 2F11-f12

<400> SEQUENCE: 45

Gly Ala Ser Ser Leu Gln Ser
1               5

<210> SEQ ID NO 46
<211> LENGTH: 11
<212> TYPE: PRT
<213> ORGANISM: Artificial
<220> FEATURE:
<223> OTHER INFORMATION: light chain CDR1, hMab 2F11-f12

<400> SEQUENCE: 46

Arg Ala Ser Glu Asp Val Asn Thr Tyr Val Ser
1               5                   10

<210> SEQ ID NO 47
<211> LENGTH: 116
<212> TYPE: PRT
<213> ORGANISM: Artificial
<220> FEATURE:
<223> OTHER INFORMATION: heavy chain variable domain, hMab 2F11-f12

<400> SEQUENCE: 47

Gln Val Gln Leu Val Gln Ser Gly Ala Glu Val Lys Lys Pro Gly Ser
1               5                   10                  15

Ser Val Lys Val Ser Cys Lys Ala Ser Gly Phe Ser Leu Thr Thr Tyr
            20                  25                  30

Asp Ile Ser Trp Val Arg Gln Ala Pro Gly Gln Gly Leu Glu Trp Met
        35                  40                  45

Gly Val Ile Trp Thr Asp Gly Gly Thr Asn Tyr Asn Ser Pro Phe Met
    50                  55                  60

Ser Arg Val Thr Ile Thr Lys Asp Glu Ser Thr Ser Thr Ala Tyr Met
65                  70                  75                  80

Glu Leu Ser Ser Leu Arg Ser Glu Asp Thr Ala Val Tyr Tyr Cys Val
                85                  90                  95
```

```
Arg Asp Gln Arg Leu Tyr Phe Asp Val Trp Gly Gln Gly Thr Thr Val
            100                 105                 110

Thr Val Ser Ser
        115

<210> SEQ ID NO 48
<211> LENGTH: 106
<212> TYPE: PRT
<213> ORGANISM: Artificial
<220> FEATURE:
<223> OTHER INFORMATION: light chain variable domain, hMab 2F11-f12

<400> SEQUENCE: 48

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asp Val Asn Thr Tyr
            20                  25                  30

Val Ser Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gly Gln Ser Phe Ser Tyr Pro Thr
                85                  90                  95

Phe Gly Gln Gly Thr Lys Leu Glu Ile Lys
            100                 105

<210> SEQ ID NO 49
<211> LENGTH: 8
<212> TYPE: PRT
<213> ORGANISM: Artificial
<220> FEATURE:
<223> OTHER INFORMATION: heavy chain CDR3, hMab 2F11-g1

<400> SEQUENCE: 49

Asp Gln Arg Leu Tyr Phe Asp Val
1               5

<210> SEQ ID NO 50
<211> LENGTH: 16
<212> TYPE: PRT
<213> ORGANISM: Artificial
<220> FEATURE:
<223> OTHER INFORMATION: heavy chain CDR2, hMab 2F11-g1

<400> SEQUENCE: 50

Val Ile Trp Thr Asp Gly Gly Thr Asn Tyr Asn Ser Pro Leu Lys Ser
1               5                   10                  15

<210> SEQ ID NO 51
<211> LENGTH: 5
<212> TYPE: PRT
<213> ORGANISM: Artificial
<220> FEATURE:
<223> OTHER INFORMATION: heavy chain CDR1, hMab 2F11-g1

<400> SEQUENCE: 51

Thr Tyr Asp Ile Ser
1               5

<210> SEQ ID NO 52
```

```
<211> LENGTH: 8
<212> TYPE: PRT
<213> ORGANISM: Artificial
<220> FEATURE:
<223> OTHER INFORMATION: light chain CDR3, hMab 2F11-g1

<400> SEQUENCE: 52

Gly Gln Ser Phe Ser Tyr Pro Thr
1               5

<210> SEQ ID NO 53
<211> LENGTH: 7
<212> TYPE: PRT
<213> ORGANISM: Artificial
<220> FEATURE:
<223> OTHER INFORMATION: light chain CDR2, hMab 2F11-g1

<400> SEQUENCE: 53

Gly Ala Ser Ser Arg Ala Thr
1               5

<210> SEQ ID NO 54
<211> LENGTH: 11
<212> TYPE: PRT
<213> ORGANISM: Artificial
<220> FEATURE:
<223> OTHER INFORMATION: light chain CDR1, hMab 2F11-g1

<400> SEQUENCE: 54

Arg Ala Ser Glu Asp Val Asn Thr Tyr Leu Ala
1               5                   10

<210> SEQ ID NO 55
<211> LENGTH: 116
<212> TYPE: PRT
<213> ORGANISM: Artificial
<220> FEATURE:
<223> OTHER INFORMATION: heavy chain variable domain, hMab 2F11-g1

<400> SEQUENCE: 55

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Thr Tyr
            20                  25                  30

Asp Ile Ser Trp Ile Arg Gln Pro Pro Gly Lys Gly Leu Glu Trp Ile
        35                  40                  45

Gly Val Ile Trp Thr Asp Gly Gly Thr Asn Tyr Asn Ser Pro Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Gln Arg Leu Tyr Phe Asp Val Trp Gly Gln Gly Thr Thr Val
            100                 105                 110

Thr Val Ser Ser
        115

<210> SEQ ID NO 56
<211> LENGTH: 106
<212> TYPE: PRT
<213> ORGANISM: Artificial
<220> FEATURE:
<223> OTHER INFORMATION: light chain variable domain, hMab 2F11-g1
```

<400> SEQUENCE: 56

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Glu Asp Val Asn Thr Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gly Gln Ser Phe Ser Tyr Pro Thr
                85                  90                  95

Phe Gly Gln Gly Thr Lys Leu Glu Ile Lys
            100                 105

<210> SEQ ID NO 57
<211> LENGTH: 107
<212> TYPE: PRT
<213> ORGANISM: Homo sapiens

<400> SEQUENCE: 57

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 58
<211> LENGTH: 330
<212> TYPE: PRT
<213> ORGANISM: Homo sapiens

<400> SEQUENCE: 58

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys

```
            100                 105                 110
Pro Ala Pro Glu Leu Leu Gly Gly Pro Ser Val Phe Leu Phe Pro Pro
            115                 120                 125
Lys Pro Lys Asp Thr Leu Met Ile Ser Arg Thr Pro Glu Val Thr Cys
130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 59
<211> LENGTH: 330
<212> TYPE: PRT
<213> ORGANISM: Artificial
<220> FEATURE:
<223> OTHER INFORMATION: human heavy chain constant region derived from
      IgG1 mutated on L234A and L235A

<400> SEQUENCE: 59

Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Gln Thr
65                  70                  75                  80
Tyr Ile Cys Asn Val Asn His Lys Pro Ser Asn Thr Lys Val Asp Lys
                85                  90                  95
Lys Val Glu Pro Lys Ser Cys Asp Lys Thr His Thr Cys Pro Pro Cys
            100                 105                 110
Pro Ala Pro Glu Ala Ala Gly Gly Pro Ser Val Phe Leu Phe Pro Pro
        115                 120                 125
```

```
Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 60
<211> LENGTH: 327
<212> TYPE: PRT
<213> ORGANISM: Homo sapiens

<400> SEQUENCE: 60

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175
```

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
            245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly Lys
            325

<210> SEQ ID NO 61
<211> LENGTH: 327
<212> TYPE: PRT
<213> ORGANISM: Artificial
<220> FEATURE:
<223> OTHER INFORMATION: human heavy chain constant region derived from
      IgG4 mutated onS228P

<400> SEQUENCE: 61

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu

```
                195                 200                 205
Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 62
<211> LENGTH: 972
<212> TYPE: PRT
<213> ORGANISM: Homo sapiens

<400> SEQUENCE: 62

Met Gly Pro Gly Val Leu Leu Leu Leu Val Ala Thr Ala Trp His
1               5                   10                  15

Gly Gln Gly Ile Pro Val Ile Glu Pro Ser Val Pro Glu Leu Val Val
            20                  25                  30

Lys Pro Gly Ala Thr Val Thr Leu Arg Cys Val Gly Asn Gly Ser Val
        35                  40                  45

Glu Trp Asp Gly Pro Pro Ser Pro His Trp Thr Leu Tyr Ser Asp Gly
    50                  55                  60

Ser Ser Ser Ile Leu Ser Thr Asn Asn Ala Thr Phe Gln Asn Thr Gly
65                  70                  75                  80

Thr Tyr Arg Cys Thr Glu Pro Gly Asp Pro Leu Gly Gly Ser Ala Ala
                85                  90                  95

Ile His Leu Tyr Val Lys Asp Pro Ala Arg Pro Trp Asn Val Leu Ala
            100                 105                 110

Gln Glu Val Val Val Phe Glu Asp Gln Asp Ala Leu Leu Pro Cys Leu
        115                 120                 125

Leu Thr Asp Pro Val Leu Glu Ala Gly Val Ser Leu Val Arg Val Arg
    130                 135                 140

Gly Arg Pro Leu Met Arg His Thr Asn Tyr Ser Phe Ser Pro Trp His
145                 150                 155                 160

Gly Phe Thr Ile His Arg Ala Lys Phe Ile Gln Ser Gln Asp Tyr Gln
                165                 170                 175

Cys Ser Ala Leu Met Gly Gly Arg Lys Val Met Ser Ile Ser Ile Arg
            180                 185                 190

Leu Lys Val Gln Lys Val Ile Pro Gly Pro Pro Ala Leu Thr Leu Val
        195                 200                 205

Pro Ala Glu Leu Val Arg Ile Arg Gly Glu Ala Ala Gln Ile Val Cys
    210                 215                 220

Ser Ala Ser Ser Val Asp Val Asn Phe Asp Val Phe Leu Gln His Asn
225                 230                 235                 240
```

```
Asn Thr Lys Leu Ala Ile Pro Gln Gln Ser Asp Phe His Asn Asn Arg
                245                 250                 255

Tyr Gln Lys Val Leu Thr Leu Asn Leu Asp Gln Val Asp Phe Gln His
            260                 265                 270

Ala Gly Asn Tyr Ser Cys Val Ala Ser Asn Val Gln Gly Lys His Ser
        275                 280                 285

Thr Ser Met Phe Phe Arg Val Glu Ser Ala Tyr Leu Asn Leu Ser
    290                 295                 300

Ser Glu Gln Asn Leu Ile Gln Glu Val Thr Val Gly Glu Gly Leu Asn
305                 310                 315                 320

Leu Lys Val Met Val Glu Ala Tyr Pro Gly Leu Gln Gly Phe Asn Trp
                325                 330                 335

Thr Tyr Leu Gly Pro Phe Ser Asp His Gln Pro Glu Pro Lys Leu Ala
            340                 345                 350

Asn Ala Thr Thr Lys Asp Thr Tyr Arg His Thr Phe Thr Leu Ser Leu
        355                 360                 365

Pro Arg Leu Lys Pro Ser Glu Ala Gly Arg Tyr Ser Phe Leu Ala Arg
    370                 375                 380

Asn Pro Gly Gly Trp Arg Ala Leu Thr Phe Glu Leu Thr Leu Arg Tyr
385                 390                 395                 400

Pro Pro Glu Val Ser Val Ile Trp Thr Phe Ile Asn Gly Ser Gly Thr
                405                 410                 415

Leu Leu Cys Ala Ala Ser Gly Tyr Pro Gln Pro Asn Val Thr Trp Leu
            420                 425                 430

Gln Cys Ser Gly His Thr Asp Arg Cys Asp Glu Ala Gln Val Leu Gln
        435                 440                 445

Val Trp Asp Asp Pro Tyr Pro Glu Val Leu Ser Gln Glu Pro Phe His
    450                 455                 460

Lys Val Thr Val Gln Ser Leu Leu Thr Val Glu Thr Leu Glu His Asn
465                 470                 475                 480

Gln Thr Tyr Glu Cys Arg Ala His Asn Ser Val Gly Ser Gly Ser Trp
                485                 490                 495

Ala Phe Ile Pro Ile Ser Ala Gly Ala His Thr His Pro Pro Asp Glu
            500                 505                 510

Phe Leu Phe Thr Pro Val Val Ala Cys Met Ser Ile Met Ala Leu
        515                 520                 525

Leu Leu Leu Leu Leu Leu Leu Leu Tyr Lys Tyr Lys Gln Lys Pro
    530                 535                 540

Lys Tyr Gln Val Arg Trp Lys Ile Ile Glu Ser Tyr Glu Gly Asn Ser
545                 550                 555                 560

Tyr Thr Phe Ile Asp Pro Thr Gln Leu Pro Tyr Asn Glu Lys Trp Glu
                565                 570                 575

Phe Pro Arg Asn Asn Leu Gln Phe Gly Lys Thr Leu Gly Ala Gly Ala
            580                 585                 590

Phe Gly Lys Val Val Glu Ala Thr Ala Phe Gly Leu Gly Lys Glu Asp
        595                 600                 605

Ala Val Leu Lys Val Ala Val Lys Met Leu Lys Ser Thr Ala His Ala
    610                 615                 620

Asp Glu Lys Glu Ala Leu Met Ser Glu Leu Lys Ile Met Ser His Leu
625                 630                 635                 640

Gly Gln His Glu Asn Ile Val Asn Leu Leu Gly Ala Cys Thr His Gly
                645                 650                 655

Gly Pro Val Leu Val Ile Thr Glu Tyr Cys Cys Tyr Gly Asp Leu Leu
```

```
            660                 665                 670
Asn Phe Leu Arg Arg Lys Ala Glu Ala Met Leu Gly Pro Ser Leu Ser
        675                 680                 685

Pro Gly Gln Asp Pro Glu Gly Val Asp Tyr Lys Asn Ile His Leu
    690                 695                 700

Glu Lys Lys Tyr Val Arg Arg Asp Ser Gly Phe Ser Gln Gly Val
705                 710                 715                 720

Asp Thr Tyr Val Glu Met Arg Pro Val Ser Thr Ser Ser Asn Asp Ser
                725                 730                 735

Phe Ser Glu Gln Asp Leu Asp Lys Glu Asp Gly Arg Pro Leu Glu Leu
            740                 745                 750

Arg Asp Leu Leu His Phe Ser Ser Gln Val Ala Gln Gly Met Ala Phe
        755                 760                 765

Leu Ala Ser Lys Asn Cys Ile His Arg Asp Val Ala Ala Arg Asn Val
    770                 775                 780

Leu Leu Thr Asn Gly His Val Ala Lys Ile Gly Asp Phe Gly Leu Ala
785                 790                 795                 800

Arg Asp Ile Met Asn Asp Ser Asn Tyr Ile Val Lys Gly Asn Ala Arg
                805                 810                 815

Leu Pro Val Lys Trp Met Ala Pro Glu Ser Ile Phe Asp Cys Val Tyr
            820                 825                 830

Thr Val Gln Ser Asp Val Trp Ser Tyr Gly Ile Leu Leu Trp Glu Ile
        835                 840                 845

Phe Ser Leu Gly Leu Asn Pro Tyr Pro Gly Ile Leu Val Asn Ser Lys
    850                 855                 860

Phe Tyr Lys Leu Val Lys Asp Gly Tyr Gln Met Ala Gln Pro Ala Phe
865                 870                 875                 880

Ala Pro Lys Asn Ile Tyr Ser Ile Met Gln Ala Cys Trp Ala Leu Glu
                885                 890                 895

Pro Thr His Arg Pro Thr Phe Gln Gln Ile Cys Ser Phe Leu Gln Glu
            900                 905                 910

Gln Ala Gln Glu Asp Arg Arg Glu Arg Asp Tyr Thr Asn Leu Pro Ser
        915                 920                 925

Ser Ser Arg Ser Gly Gly Ser Gly Ser Ser Ser Glu Leu Glu Glu
    930                 935                 940

Glu Ser Ser Ser Glu His Leu Thr Cys Cys Glu Gln Gly Asp Ile Ala
945                 950                 955                 960

Gln Pro Leu Leu Gln Pro Asn Asn Tyr Gln Phe Cys
                965                 970

<210> SEQ ID NO 63
<211> LENGTH: 972
<212> TYPE: PRT
<213> ORGANISM: Artificial
<220> FEATURE:
<223> OTHER INFORMATION: mutant CSF-1R L301S Y969F

<400> SEQUENCE: 63

Met Gly Pro Gly Val Leu Leu Leu Leu Val Ala Thr Ala Trp His
1               5                   10                  15

Gly Gln Gly Ile Pro Val Ile Glu Pro Ser Val Pro Glu Leu Val Val
                20                  25                  30

Lys Pro Gly Ala Thr Val Th

```
                50                  55                  60
Ser Ser Ser Ile Leu Ser Thr Asn Asn Ala Thr Phe Gln Asn Thr Gly
65                  70                  75                  80

Thr Tyr Arg Cys Thr Glu Pro Gly Asp Pro Leu Gly Gly Ser Ala Ala
                85                  90                  95

Ile His Leu Tyr Val Lys Asp Pro Ala Arg Pro Trp Asn Val Leu Ala
                100                 105                 110

Gln Glu Val Val Val Phe Glu Asp Gln Asp Ala Leu Leu Pro Cys Leu
                115                 120                 125

Leu Thr Asp Pro Val Leu Glu Ala Gly Val Ser Leu Val Arg Val Arg
                130                 135                 140

Gly Arg Pro Leu Met Arg His Thr Asn Tyr Ser Phe Ser Pro Trp His
145                 150                 155                 160

Gly Phe Thr Ile His Arg Ala Lys Phe Ile Gln Ser Gln Asp Tyr Gln
                165                 170                 175

Cys Ser Ala Leu Met Gly Gly Arg Lys Val Met Ser Ile Ser Ile Arg
                180                 185                 190

Leu Lys Val Gln Lys Val Ile Pro Gly Pro Pro Ala Leu Thr Leu Val
                195                 200                 205

Pro Ala Glu Leu Val Arg Ile Arg Gly Glu Ala Ala Gln Ile Val Cys
                210                 215                 220

Ser Ala Ser Ser Val Asp Val Asn Phe Asp Val Phe Leu Gln His Asn
225                 230                 235                 240

Asn Thr Lys Leu Ala Ile Pro Gln Gln Ser Asp Phe His Asn Asn Arg
                245                 250                 255

Tyr Gln Lys Val Leu Thr Leu Asn Leu Asp Gln Val Asp Phe Gln His
                260                 265                 270

Ala Gly Asn Tyr Ser Cys Val Ala Ser Asn Val Gln Gly Lys His Ser
                275                 280                 285

Thr Ser Met Phe Phe Arg Val Val Glu Ser Ala Tyr Ser Asn Leu Ser
                290                 295                 300

Ser Glu Gln Asn Leu Ile Gln Glu Val Thr Val Gly Glu Gly Leu Asn
305                 310                 315                 320

Leu Lys Val Met Val Glu Ala Tyr Pro Gly Leu Gln Gly Phe Asn Trp
                325                 330                 335

Thr Tyr Leu Gly Pro Phe Ser Asp His Gln Pro Glu Pro Lys Leu Ala
                340                 345                 350

Asn Ala Thr Thr Lys Asp Thr Tyr Arg His Thr Phe Thr Leu Ser Leu
                355                 360                 365

Pro Arg Leu Lys Pro Ser Glu Ala Gly Arg Tyr Ser Phe Leu Ala Arg
370                 375                 380

Asn Pro Gly Gly Trp Arg Ala Leu Thr Phe Glu Leu Thr Leu Arg Tyr
385                 390                 395                 400

Pro Pro Glu Val Ser Val Ile Trp Thr Phe Ile Asn Gly Ser Gly Thr
                405                 410                 415

Leu Leu Cys Ala Ala Ser Gly Tyr Pro Gln Pro Asn Val Thr Trp Leu
                420                 425                 430

Gln Cys Ser Gly His Thr Asp Arg Cys Asp Glu Ala Gln Val Leu Gln
                435                 440                 445

Val Trp Asp Asp Pro Tyr Pro Glu Val Leu Ser Gln Glu Pro Phe His
                450                 455                 460

Lys Val Thr Val Gln Ser Leu Leu Thr Val Glu Thr Leu Glu His Asn
465                 470                 475                 480
```

```
Gln Thr Tyr Glu Cys Arg Ala His Asn Ser Val Gly Ser Gly Ser Trp
            485                 490                 495

Ala Phe Ile Pro Ile Ser Ala Gly Ala His Thr His Pro Pro Asp Glu
            500                 505                 510

Phe Leu Phe Thr Pro Val Val Ala Cys Met Ser Ile Met Ala Leu
            515                 520                 525

Leu Leu Leu Leu Leu Leu Leu Leu Tyr Lys Tyr Lys Gln Lys Pro
            530                 535                 540

Lys Tyr Gln Val Arg Trp Lys Ile Ile Glu Ser Tyr Glu Gly Asn Ser
545                 550                 555                 560

Tyr Thr Phe Ile Asp Pro Thr Gln Leu Pro Tyr Asn Glu Lys Trp Glu
            565                 570                 575

Phe Pro Arg Asn Asn Leu Gln Phe Gly Lys Thr Leu Gly Ala Gly Ala
            580                 585                 590

Phe Gly Lys Val Val Glu Ala Thr Ala Phe Gly Leu Gly Lys Glu Asp
            595                 600                 605

Ala Val Leu Lys Val Ala Val Lys Met Leu Lys Ser Thr Ala His Ala
            610                 615                 620

Asp Glu Lys Glu Ala Leu Met Ser Glu Leu Lys Ile Met Ser His Leu
625                 630                 635                 640

Gly Gln His Glu Asn Ile Val Asn Leu Leu Gly Ala Cys Thr His Gly
            645                 650                 655

Gly Pro Val Leu Val Ile Thr Glu Tyr Cys Cys Tyr Gly Asp Leu Leu
            660                 665                 670

Asn Phe Leu Arg Arg Lys Ala Glu Ala Met Leu Gly Pro Ser Leu Ser
            675                 680                 685

Pro Gly Gln Asp Pro Glu Gly Gly Val Asp Tyr Lys Asn Ile His Leu
            690                 695                 700

Glu Lys Lys Tyr Val Arg Arg Asp Ser Gly Phe Ser Ser Gln Gly Val
705                 710                 715                 720

Asp Thr Tyr Val Glu Met Arg Pro Val Ser Thr Ser Ser Asn Asp Ser
            725                 730                 735

Phe Ser Glu Gln Asp Leu Asp Lys Glu Asp Gly Arg Pro Leu Glu Leu
            740                 745                 750

Arg Asp Leu Leu His Phe Ser Ser Gln Val Ala Gln Gly Met Ala Phe
            755                 760                 765

Leu Ala Ser Lys Asn Cys Ile His Arg Asp Val Ala Ala Arg Asn Val
            770                 775                 780

Leu Leu Thr Asn Gly His Val Ala Lys Ile Gly Asp Phe Gly Leu Ala
785                 790                 795                 800

Arg Asp Ile Met Asn Asp Ser Asn Tyr Ile Val Lys Gly Asn Ala Arg
            805                 810                 815

Leu Pro Val Lys Trp Met Ala Pro Glu Ser Ile Phe Asp Cys Val Tyr
            820                 825                 830

Thr Val Gln Ser Asp Val Trp Ser Tyr Gly Ile Leu Leu Trp Glu Ile
            835                 840                 845

Phe Ser Leu Gly Leu Asn Pro Tyr Pro Gly Ile Leu Val Asn Ser Lys
            850                 855                 860

Phe Tyr Lys Leu Val Lys Asp Gly Tyr Gln Met Ala Gln Pro Ala Phe
865                 870                 875                 880

Ala Pro Lys Asn Ile Tyr Ser Ile Met Gln Ala Cys Trp Ala Leu Glu
            885                 890                 895
```

```
Pro Thr His Arg Pro Thr Phe Gln Gln Ile Cys Ser Phe Leu Gln Glu
            900                 905                 910

Gln Ala Gln Glu Asp Arg Arg Glu Arg Asp Tyr Thr Asn Leu Pro Ser
            915                 920                 925

Ser Ser Arg Ser Gly Gly Ser Gly Ser Ser Ser Glu Leu Glu Glu
        930                 935                 940

Glu Ser Ser Ser Glu His Leu Thr Cys Cys Glu Gln Gly Asp Ile Ala
945                 950                 955                 960

Gln Pro Leu Leu Gln Pro Asn Asn Phe Gln Phe Cys
                965                 970
```

<210> SEQ ID NO 64
<211> LENGTH: 493
<212> TYPE: PRT
<213> ORGANISM: Artificial
<220> FEATURE:
<223> OTHER INFORMATION: human CSF-1R Extracellular Domain

<400> SEQUENCE: 64

```
Ile Pro Val Ile Glu Pro Ser Val Pro Glu Leu Val Val Lys Pro Gly
1               5                   10                  15

Ala Thr Val Thr Leu Arg Cys Val Gly Asn Gly Ser Val Glu Trp Asp
            20                  25                  30

Gly Pro Pro Ser Pro His Trp Thr Leu Tyr Ser Asp Gly Ser Ser Ser
        35                  40                  45

Ile Leu Ser Thr Asn Asn Ala Thr Phe Gln Asn Thr Gly Thr Tyr Arg
    50                  55                  60

Cys Thr Glu Pro Gly Asp Pro Leu Gly Gly Ser Ala Ala Ile His Leu
65                  70                  75                  80

Tyr Val Lys Asp Pro Ala Arg Pro Trp Asn Val Leu Ala Gln Glu Val
                85                  90                  95

Val Val Phe Glu Asp Gln Asp Ala Leu Leu Pro Cys Leu Leu Thr Asp
            100                 105                 110

Pro Val Leu Glu Ala Gly Val Ser Leu Val Arg Val Arg Gly Arg Pro
        115                 120                 125

Leu Met Arg His Thr Asn Tyr Ser Phe Ser Pro Trp His Gly Phe Thr
    130                 135                 140

Ile His Arg Ala Lys Phe Ile Gln Ser Gln Asp Tyr Gln Cys Ser Ala
145                 150                 155                 160

Leu Met Gly Gly Arg Lys Val Met Ser Ile Ser Ile Arg Leu Lys Val
                165                 170                 175

Gln Lys Val Ile Pro Gly Pro Pro Ala Leu Thr Leu Val Pro Ala Glu
            180                 185                 190

Leu Val Arg Ile Arg Gly Glu Ala Ala Gln Ile Val Cys Ser Ala Ser
        195                 200                 205

Ser Val Asp Val Asn Phe Asp Val Phe Leu Gln His Asn Asn Thr Lys
    210                 215                 220

Leu Ala Ile Pro Gln Gln Ser Asp Phe His Asn Asn Arg Tyr Gln Lys
225                 230                 235                 240

Val Leu Thr Leu Asn Leu Asp Gln Val Asp Phe Gln His Ala Gly Asn
                245                 250                 255

Tyr Ser Cys Val Ala Ser Asn Val Gln Gly Lys His Ser Thr Ser Met
            260                 265                 270

Phe Phe Arg Val Val Glu Ser Ala Tyr Leu Asn Leu Ser Ser Glu Gln
        275                 280                 285
```

```
Asn Leu Ile Gln Glu Val Thr Val Gly Gly Leu Asn Leu Lys Val
    290                 295                 300

Met Val Glu Ala Tyr Pro Gly Leu Gln Gly Phe Asn Trp Thr Tyr Leu
305                 310                 315                 320

Gly Pro Phe Ser Asp His Gln Pro Gly Pro Lys Leu Ala Asn Ala Thr
                325                 330                 335

Thr Lys Asp Thr Tyr Arg His Thr Phe Thr Leu Ser Leu Pro Arg Leu
                340                 345                 350

Lys Pro Ser Glu Ala Gly Arg Tyr Ser Phe Leu Ala Arg Asn Pro Gly
                355                 360                 365

Gly Trp Arg Ala Leu Thr Phe Glu Leu Thr Leu Arg Tyr Pro Pro Glu
370                 375                 380

Val Ser Val Ile Trp Thr Phe Ile Asn Gly Ser Gly Thr Leu Leu Cys
385                 390                 395                 400

Ala Ala Ser Gly Tyr Pro Gln Pro Asn Val Thr Trp Leu Gln Cys Ser
                405                 410                 415

Gly His Thr Asp Arg Cys Asp Glu Ala Gln Val Leu Gln Val Trp Asp
                420                 425                 430

Asp Pro Tyr Pro Glu Val Leu Ser Gln Glu Pro Phe His Lys Val Thr
                435                 440                 445

Val Gln Ser Leu Leu Thr Val Glu Thr Leu Glu His Asn Gln Thr Tyr
                450                 455                 460

Glu Cys Arg Ala His Asn Ser Val Gly Ser Gly Ser Trp Ala Phe Ile
465                 470                 475                 480

Pro Ile Ser Ala Gly Ala His Thr His Pro Pro Asp Glu
                485                 490

<210> SEQ ID NO 65
<211> LENGTH: 388
<212> TYPE: PRT
<213> ORGANISM: Artificial
<220> FEATURE:
<223> OTHER INFORMATION: human CSF-1R fragment delD4

<400> SEQUENCE: 65

Ile Pro Val Ile Glu Pro Ser Val Pro Glu Leu Val Val Lys Pro Gly
1               5                   10                  15

Ala Thr Val Thr Leu Arg Cys Val Gly Asn Gly Ser Val Glu Trp Asp
                20                  25                  30

Gly Pro Pro Ser Pro His Trp Thr Leu Tyr Ser Asp Gly Ser Ser Ser
                35                  40                  45

Ile Leu Ser Thr Asn Asn Ala Thr Phe Gln Asn Thr Gly Thr Tyr Arg
    50                  55                  60

Cys Thr Glu Pro Gly Asp Pro Leu Gly Gly Ser Ala Ala Ile His Leu
65                  70                  75                  80

Tyr Val Lys Asp Pro Ala Arg Pro Trp Asn Val Leu Ala Gln Glu Val
                85                  90                  95

Val Val Phe Glu Asp Gln Asp Ala Leu Leu Pro Cys Leu Leu Thr Asp
                100                 105                 110

Pro Val Leu Glu Ala Gly Val Ser Leu Val Arg Val Arg Gly Arg Pro
                115                 120                 125

Leu Met Arg His Thr Asn Tyr Ser Phe Ser Pro Trp His Gly Phe Thr
    130                 135                 140

Ile His Arg Ala Lys Phe Ile Gln Ser Gln Asp Tyr Gln Cys Ser Ala
145                 150                 155                 160
```

```
Leu Met Gly Gly Arg Lys Val Met Ser Ile Ser Ile Arg Leu Lys Val
                165                 170                 175

Gln Lys Val Ile Pro Gly Pro Ala Leu Thr Leu Val Pro Ala Glu
            180                 185                 190

Leu Val Arg Ile Arg Gly Glu Ala Ala Gln Ile Val Cys Ser Ala Ser
            195                 200                 205

Ser Val Asp Val Asn Phe Asp Val Phe Leu Gln His Asn Asn Thr Lys
210                 215                 220

Leu Ala Ile Pro Gln Gln Ser Asp Phe His Asn Asn Arg Tyr Gln Lys
225                 230                 235                 240

Val Leu Thr Leu Asn Leu Asp Gln Val Asp Phe Gln His Ala Gly Asn
                245                 250                 255

Tyr Ser Cys Val Ala Ser Asn Val Gln Gly Lys His Ser Thr Ser Met
                260                 265                 270

Phe Phe Arg Tyr Pro Pro Glu Val Ser Val Ile Trp Thr Phe Ile Asn
            275                 280                 285

Gly Ser Gly Thr Leu Leu Cys Ala Ala Ser Gly Tyr Pro Gln Pro Asn
290                 295                 300

Val Thr Trp Leu Gln Cys Ser Gly His Thr Asp Arg Cys Asp Glu Ala
305                 310                 315                 320

Gln Val Leu Gln Val Trp Asp Asp Pro Tyr Pro Glu Val Leu Ser Gln
                325                 330                 335

Glu Pro Phe His Lys Val Thr Val Gln Ser Leu Leu Thr Val Glu Thr
            340                 345                 350

Leu Glu His Asn Gln Thr Tyr Glu Cys Arg Ala His Asn Ser Val Gly
            355                 360                 365

Ser Gly Ser Trp Ala Phe Ile Pro Ile Ser Ala Gly Ala His Thr His
370                 375                 380

Pro Pro Asp Glu
385

<210> SEQ ID NO 66
<211> LENGTH: 292
<212> TYPE: PRT
<213> ORGANISM: Artificial
<220> FEATURE:
<223> OTHER INFORMATION: human CSF-1R fragment D1-D3

<400> SEQUENCE: 66

Ile Pro Val Ile Glu Pro Ser Val Pro Glu Leu Val Val Lys Pro Gly
1               5                   10                  15

Ala Thr Val Thr Leu Arg Cys Val Gly Asn Gly Ser Val Glu Trp Asp
            20                  25                  30

Gly Pro Pro Ser Pro His Trp Thr Leu Tyr Ser Asp Gly Ser Ser Ser
        35                  40                  45

Ile Leu Ser Thr Asn Asn Ala Thr Phe Gln Asn Thr Gly Thr Tyr Arg
50                  55                  60

Cys Thr Glu Pro Gly Asp Pro Leu Gly Gly Ser Ala Ala Ile His Leu
65                  70                  75                  80

Tyr Val Lys Asp Pro Ala Arg Pro Trp Asn Val Leu Ala Gln Glu Val
                85                  90                  95

Val Val Phe Glu Asp Gln Asp Ala Leu Leu Pro Cys Leu Leu Thr Asp
            100                 105                 110

Pro Val Leu Glu Ala Gly Val Ser Leu Val Arg Val Arg Gly Arg Pro
        115                 120                 125
```

```
Leu Met Arg His Thr Asn Tyr Ser Phe Ser Pro Trp His Gly Phe Thr
            130                 135                 140

Ile His Arg Ala Lys Phe Ile Gln Ser Gln Asp Tyr Gln Cys Ser Ala
145                 150                 155                 160

Leu Met Gly Gly Arg Lys Val Met Ser Ile Ser Ile Arg Leu Lys Val
                165                 170                 175

Gln Lys Val Ile Pro Gly Pro Pro Ala Leu Thr Leu Val Pro Ala Glu
            180                 185                 190

Leu Val Arg Ile Arg Gly Glu Ala Ala Gln Ile Val Cys Ser Ala Ser
                195                 200                 205

Ser Val Asp Val Asn Phe Asp Val Phe Leu Gln His Asn Asn Thr Lys
210                 215                 220

Leu Ala Ile Pro Gln Gln Ser Asp Phe His Asn Asn Arg Tyr Gln Lys
225                 230                 235                 240

Val Leu Thr Leu Asn Leu Asp Gln Val Asp Phe Gln His Ala Gly Asn
                245                 250                 255

Tyr Ser Cys Val Ala Ser Asn Val Gln Gly Lys His Ser Thr Ser Met
            260                 265                 270

Phe Phe Arg Val Val Glu Ser Ala Tyr Leu Asn Leu Ser Ser Glu Gln
                275                 280                 285

Asn Leu Ile Gln
    290

<210> SEQ ID NO 67
<211> LENGTH: 21
<212> TYPE: PRT
<213> ORGANISM: Artificial
<220> FEATURE:
<223> OTHER INFORMATION: signal peptide

<400> SEQUENCE: 67

Met Gly Ser Gly Pro Gly Val Leu Leu Leu Leu Val Ala Thr Ala
1               5                   10                  15

Trp His Gly Gln Gly
            20

<210> SEQ ID NO 68
<211> LENGTH: 36
<212> TYPE: DNA
<213> ORGANISM: Artificial
<220> FEATURE:
<223> OTHER INFORMATION: Primer

<400> SEQUENCE: 68
cacctccatg ttcttccggt accccccaga ggtaag                         36

<210> SEQ ID NO 69
<211> LENGTH: 8
<212> TYPE: PRT
<213> ORGANISM: Mus musculus

<400> SEQUENCE: 69

Asp Leu Arg Leu Tyr Phe Asp Val
1               5

<210> SEQ ID NO 70
<211> LENGTH: 16
<212> TYPE: PRT
<213> ORGANISM: Mus musculus

<400> SEQUENCE: 70
```

```
Val Ile Trp Ser Gly Gly Thr Asn Tyr Asn Ser Pro Phe Met Ser
1               5                   10                  15
```

<210> SEQ ID NO 71
<211> LENGTH: 10
<212> TYPE: PRT
<213> ORGANISM: Mus musculus

<400> SEQUENCE: 71

```
Gly Phe Ser Leu Thr Ser Tyr Asp Ile Ser
1               5                   10
```

<210> SEQ ID NO 72
<211> LENGTH: 8
<212> TYPE: PRT
<213> ORGANISM: Mus musculus

<400> SEQUENCE: 72

```
Gly Gln Ser Phe Thr Tyr Pro Thr
1               5
```

<210> SEQ ID NO 73
<211> LENGTH: 7
<212> TYPE: PRT
<213> ORGANISM: Mus musculus

<400> SEQUENCE: 73

```
Gly Ser Ser Asn Arg Tyr Thr
1               5
```

<210> SEQ ID NO 74
<211> LENGTH: 11
<212> TYPE: PRT
<213> ORGANISM: Mus musculus

<400> SEQUENCE: 74

```
Lys Ala Ser Glu Asp Val Gly Thr Tyr Val Ser
1               5                   10
```

<210> SEQ ID NO 75
<211> LENGTH: 116
<212> TYPE: PRT
<213> ORGANISM: Mus musculus

<400> SEQUENCE: 75

```
Arg Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ser Tyr
                20                  25                  30

Asp Ile Ser Trp Ile Arg Gln Ser Pro Gly Lys Gly Leu Glu Trp Leu
            35                  40                  45

Gly Val Ile Trp Ser Gly Gly Thr Asn Tyr Asn Ser Pro Phe Met
        50                  55                  60

Ser Arg Leu Arg Ile Ser Lys Asp Asp Ser Arg Ser Gln Val Phe Leu
65                  70                  75                  80

Lys Val Asn Arg Leu Gln Thr Asp Asp Thr Ala Ile Tyr Tyr Cys Val
                85                  90                  95

Arg Asp Leu Arg Leu Tyr Phe Asp Val Trp Gly Ala Gly Thr Thr Val
            100                 105                 110

Thr Val Ser Ser
            115
```

<210> SEQ ID NO 76
<211> LENGTH: 106
<212> TYPE: PRT
<213> ORGANISM: Mus musculus

<400> SEQUENCE: 76

```
Lys Ile Val Met Thr Gln Ser Pro Lys Ser Met Ser Val Ser Val Gly
1               5                   10                  15

Glu Arg Val Ser Leu Ser Cys Lys Ala Ser Glu Asp Val Gly Thr Tyr
            20                  25                  30

Val Ser Trp Tyr Gln Gln Lys Pro Glu Gln Ser Pro Lys Leu Leu Ile
        35                  40                  45

Tyr Gly Ser Ser Asn Arg Tyr Thr Gly Val Pro Asp Arg Phe Thr Gly
    50                  55                  60

Ser Gly Ser Ala Thr Asp Phe Thr Leu Thr Ile Ser Ser Val Gln Ala
65                  70                  75                  80

Glu Asp Leu Ala Asp Tyr Ser Cys Gly Gln Ser Phe Thr Tyr Pro Thr
                85                  90                  95

Phe Gly Thr Gly Thr Lys Leu Glu Ile Lys
            100                 105
```

<210> SEQ ID NO 77
<211> LENGTH: 8
<212> TYPE: PRT
<213> ORGANISM: Mus musculus

<400> SEQUENCE: 77

```
Asp Pro Arg Leu Tyr Phe Asp Val
1               5
```

<210> SEQ ID NO 78
<211> LENGTH: 16
<212> TYPE: PRT
<213> ORGANISM: Mus musculus

<400> SEQUENCE: 78

```
Val Ile Trp Thr Gly Gly Gly Thr Asn Tyr Asn Ser Gly Phe Met Ser
1               5                   10                  15
```

<210> SEQ ID NO 79
<211> LENGTH: 10
<212> TYPE: PRT
<213> ORGANISM: Mus musculus

<400> SEQUENCE: 79

```
Gly Ser Ser Leu Asp Ser Phe Asp Ile Ser
1               5                   10
```

<210> SEQ ID NO 80
<211> LENGTH: 8
<212> TYPE: PRT
<213> ORGANISM: Mus musculus

<400> SEQUENCE: 80

```
Gly Gln Thr Phe Ser Tyr Pro Thr
1               5
```

<210> SEQ ID NO 81
<211> LENGTH: 7
<212> TYPE: PRT
<213> ORGANISM: Mus musculus

```
<400> SEQUENCE: 81

Gly Ala Ser Asn Arg Tyr Thr
1               5

<210> SEQ ID NO 82
<211> LENGTH: 11
<212> TYPE: PRT
<213> ORGANISM: Mus musculus

<400> SEQUENCE: 82

Lys Ala Ser Glu Asp Val Val Thr Tyr Val Ser
1               5                   10

<210> SEQ ID NO 83
<211> LENGTH: 116
<212> TYPE: PRT
<213> ORGANISM: Mus musculus

<400> SEQUENCE: 83

Gln Val Gln Leu Lys Glu Ser Gly Pro Gly Leu Val Ala Pro Ser Lys
1               5                   10                  15

Ser Leu Ser Ile Thr Cys Thr Val Ser Gly Ser Ser Leu Asp Ser Phe
            20                  25                  30

Asp Ile Ser Trp Ile Arg Gln Pro Pro Gly Lys Gly Leu Glu Trp Leu
        35                  40                  45

Gly Val Ile Trp Thr Gly Gly Thr Asn Tyr Asn Ser Gly Phe Met
    50                  55                  60

Ser Arg Leu Arg Ile Ser Lys Asp Asn Ser Lys Ser Gln Val Phe Leu
65                  70                  75                  80

Lys Met Ser Ser Leu Gln Ser Asp Asp Thr Ala Ile Tyr Tyr Cys Val
                85                  90                  95

Arg Asp Pro Arg Leu Tyr Phe Asp Val Trp Gly Ala Gly Thr Thr Val
            100                 105                 110

Thr Val Ser Ser
        115

<210> SEQ ID NO 84
<211> LENGTH: 106
<212> TYPE: PRT
<213> ORGANISM: Mus musculus

<400> SEQUENCE: 84

Asn Ile Val Met Thr Gln Ser Pro Lys Ser Met Ser Met Ser Val Gly
1               5                   10                  15

Glu Arg Val Thr Leu Ser Cys Lys Ala Ser Glu Asp Val Val Thr Tyr
            20                  25                  30

Val Ser Trp Tyr Gln Gln Lys Pro Glu Gln Ser Pro Lys Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Ser Ser Ile Gln Ala
65                  70                  75                  80

Glu Asp Leu Ala Asp Tyr Tyr Cys Gly Gln Thr Phe Ser Tyr Pro Thr
                85                  90                  95

Phe Gly Thr Gly Thr Lys Leu Glu Ile Lys
            100                 105
```

```
<210> SEQ ID NO 85
<211> LENGTH: 218
<212> TYPE: PRT
<213> ORGANISM: Artificial
<220> FEATURE:
<223> OTHER INFORMATION: human CSF-1R fragment domains D4-D5

<400> SEQUENCE: 85

Val Val Glu Ser Ala Tyr Leu Asn Leu Ser Ser Glu Gln Asn Leu Ile
1               5                   10                  15

Gln Glu Val Thr Val Gly Glu Gly Leu Asn Leu Lys Val Met Val Glu
            20                  25                  30

Ala Tyr Pro Gly Leu Gln Gly Phe Asn Trp Thr Tyr Leu Gly Pro Phe
        35                  40                  45

Ser Asp His Gln Pro Glu Pro Lys Leu Ala Asn Ala Thr Thr Lys Asp
    50                  55                  60

Thr Tyr Arg His Thr Phe Thr Leu Ser Leu Pro Arg Leu Lys Pro Ser
65                  70                  75                  80

Glu Ala Gly Arg Tyr Ser Phe Leu Ala Arg Asn Pro Gly Gly Trp Arg
                85                  90                  95

Ala Leu Thr Phe Glu Leu Thr Leu Arg Tyr Pro Pro Glu Val Ser Val
            100                 105                 110

Ile Trp Thr Phe Ile Asn Gly Ser Gly Thr Leu Leu Cys Ala Ala Ser
        115                 120                 125

Gly Tyr Pro Gln Pro Asn Val Thr Trp Leu Gln Cys Ser Gly His Thr
    130                 135                 140

Asp Arg Cys Asp Glu Ala Gln Val Leu Gln Val Trp Asp Asp Pro Tyr
145                 150                 155                 160

Pro Glu Val Leu Ser Gln Glu Pro Phe His Lys Val Thr Val Gln Ser
                165                 170                 175

Leu Leu Thr Val Glu Thr Leu Glu His Asn Gln Thr Tyr Glu Cys Arg
            180                 185                 190

Ala His Asn Ser Val Gly Ser Gly Ser Trp Ala Phe Ile Pro Ile Ser
        195                 200                 205

Ala Gly Ala His Thr His Pro Pro Asp Glu
    210                 215

<210> SEQ ID NO 86
<211> LENGTH: 554
<212> TYPE: PRT
<213> ORGANISM: homo sapiens

<400> SEQUENCE: 86

Met Thr Ala Pro Gly Ala Ala Gly Arg Cys Pro Pro Thr Thr Trp Leu
1               5                   10                  15

Gly Ser Leu Leu Leu Leu Val Cys Leu Leu Ala Ser Arg Ser Ile Thr
            20                  25                  30

Glu Glu Val Ser Glu Tyr Cys Ser His Met Ile Gly Ser Gly His Leu
        35                  40                  45

Gln Ser Leu Gln Arg Leu Ile Asp Ser Gln Met Glu Thr Ser Cys Gln
    50                  55                  60

Ile Thr Phe Glu Phe Val Asp Gln Glu Gln Leu Lys Asp Pro Val Cys
65                  70                  75                  80

Tyr Leu Lys Lys Ala Phe Leu Leu Val Gln Asp Ile Met Glu Asp Thr
                85                  90                  95

Met Arg Phe Arg Asp Asn Thr Pro Asn Ala Ile Ala Ile Val Gln Leu
            100                 105                 110
```

```
Gln Glu Leu Ser Leu Arg Leu Lys Ser Cys Phe Thr Lys Asp Tyr Glu
            115                 120                 125

Glu His Asp Lys Ala Cys Val Arg Thr Phe Tyr Glu Thr Pro Leu Gln
        130                 135                 140

Leu Leu Glu Lys Val Lys Asn Val Phe Asn Glu Thr Lys Asn Leu Leu
145                 150                 155                 160

Asp Lys Asp Trp Asn Ile Phe Ser Lys Asn Cys Asn Asn Ser Phe Ala
                165                 170                 175

Glu Cys Ser Ser Gln Asp Val Val Thr Lys Pro Asp Cys Asn Cys Leu
            180                 185                 190

Tyr Pro Lys Ala Ile Pro Ser Ser Asp Pro Ala Ser Val Ser Pro His
        195                 200                 205

Gln Pro Leu Ala Pro Ser Met Ala Pro Val Ala Gly Leu Thr Trp Glu
        210                 215                 220

Asp Ser Glu Gly Thr Glu Gly Ser Ser Leu Leu Pro Gly Glu Gln Pro
225                 230                 235                 240

Leu His Thr Val Asp Pro Gly Ser Ala Lys Gln Arg Pro Pro Arg Ser
                245                 250                 255

Thr Cys Gln Ser Phe Glu Pro Pro Glu Thr Pro Val Val Lys Asp Ser
            260                 265                 270

Thr Ile Gly Gly Ser Pro Gln Pro Arg Pro Ser Val Gly Ala Phe Asn
        275                 280                 285

Pro Gly Met Glu Asp Ile Leu Asp Ser Ala Met Gly Thr Asn Trp Val
        290                 295                 300

Pro Glu Glu Ala Ser Gly Glu Ala Ser Glu Ile Pro Val Pro Gln Gly
305                 310                 315                 320

Thr Glu Leu Ser Pro Ser Arg Pro Gly Gly Gly Ser Met Gln Thr Glu
                325                 330                 335

Pro Ala Arg Pro Ser Asn Phe Leu Ser Ala Ser Ser Pro Leu Pro Ala
            340                 345                 350

Ser Ala Lys Gly Gln Gln Pro Ala Asp Val Thr Gly Thr Ala Leu Pro
        355                 360                 365

Arg Val Gly Pro Val Arg Pro Thr Gly Gln Asp Trp Asn His Thr Pro
        370                 375                 380

Gln Lys Thr Asp His Pro Ser Ala Leu Leu Arg Asp Pro Pro Glu Pro
385                 390                 395                 400

Gly Ser Pro Arg Ile Ser Ser Leu Arg Pro Gln Gly Leu Ser Asn Pro
                405                 410                 415

Ser Thr Leu Ser Ala Gln Pro Gln Leu Ser Arg Ser His Ser Ser Gly
            420                 425                 430

Ser Val Leu Pro Leu Gly Glu Leu Glu Gly Arg Arg Ser Thr Arg Asp
        435                 440                 445

Arg Arg Ser Pro Ala Glu Pro Glu Gly Gly Pro Ala Ser Glu Gly Ala
450                 455                 460

Ala Arg Pro Leu Pro Arg Phe Asn Ser Val Pro Leu Thr Asp Thr Gly
465                 470                 475                 480

His Glu Arg Gln Ser Glu Gly Ser Phe Ser Pro Gln Leu Gln Glu Ser
                485                 490                 495

Val Phe His Leu Leu Val Pro Ser Val Ile Leu Val Leu Leu Ala Val
            500                 505                 510

Gly Gly Leu Leu Phe Tyr Arg Trp Arg Arg Arg Ser His Gln Glu Pro
        515                 520                 525
```

Gln Arg Ala Asp Ser Pro Leu Glu Gln Pro Glu Gly Ser Pro Leu Thr
            530                 535                 540

Gln Asp Asp Arg Gln Val Glu Leu Pro Val
545                 550

<210> SEQ ID NO 87
<211> LENGTH: 242
<212> TYPE: PRT
<213> ORGANISM: homo sapiens

<400> SEQUENCE: 87

Met Pro Arg Gly Phe Thr Trp Leu Arg Tyr Leu Gly Ile Phe Leu Gly
1               5                   10                  15

Val Ala Leu Gly Asn Glu Pro Leu Glu Met Trp Pro Leu Thr Gln Asn
                20                  25                  30

Glu Glu Cys Thr Val Thr Gly Phe Leu Arg Asp Lys Leu Gln Tyr Arg
            35                  40                  45

Ser Arg Leu Gln Tyr Met Lys His Tyr Phe Pro Ile Asn Tyr Lys Ile
        50                  55                  60

Ser Val Pro Tyr Glu Gly Val Phe Arg Ile Ala Asn Val Thr Arg Leu
65                  70                  75                  80

Gln Arg Ala Gln Val Ser Glu Arg Glu Leu Arg Tyr Leu Trp Val Leu
                85                  90                  95

Val Ser Leu Ser Ala Thr Glu Ser Val Gln Asp Val Leu Leu Glu Gly
            100                 105                 110

His Pro Ser Trp Lys Tyr Leu Gln Glu Val Glu Thr Leu Leu Leu Asn
        115                 120                 125

Val Gln Gln Gly Leu Thr Asp Val Glu Val Ser Pro Lys Val Glu Ser
    130                 135                 140

Val Leu Ser Leu Leu Asn Ala Pro Gly Pro Asn Leu Lys Leu Val Arg
145                 150                 155                 160

Pro Lys Ala Leu Leu Asp Asn Cys Phe Arg Val Met Glu Leu Leu Tyr
                165                 170                 175

Cys Ser Cys Cys Lys Gln Ser Ser Val Leu Asn Trp Gln Asp Cys Glu
            180                 185                 190

Val Pro Ser Pro Gln Ser Cys Ser Pro Glu Pro Ser Leu Gln Tyr Ala
        195                 200                 205

Ala Thr Gln Leu Tyr Pro Pro Pro Trp Ser Pro Ser Ser Pro
    210                 215                 220

His Ser Thr Gly Ser Val Arg Pro Val Arg Ala Gln Gly Glu Gly Leu
225                 230                 235                 240

Leu Pro

<210> SEQ ID NO 88
<211> LENGTH: 290
<212> TYPE: PRT
<213> ORGANISM: homo sapiens

<400> SEQUENCE: 88

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
                20                  25                  30

Gly Ser Asn Met Thr Ile Glu Cys Lys Phe Pro Val Glu Lys Gln Leu
            35                  40                  45

Asp Leu Ala Ala Leu Ile Val Tyr Trp Glu Met Glu Asp Lys Asn Ile

```
            50                  55                  60
Ile Gln Phe Val His Gly Glu Glu Asp Leu Lys Val Gln His Ser Ser
 65                  70                  75                  80

Tyr Arg Gln Arg Ala Arg Leu Leu Lys Asp Gln Leu Ser Leu Gly Asn
                 85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
            115                 120                 125

Lys Val Asn Ala Pro Tyr Asn Lys Ile Asn Gln Arg Ile Leu Val Val
        130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
        275                 280                 285

Glu Thr
    290

<210> SEQ ID NO 89
<211> LENGTH: 118
<212> TYPE: PRT
<213> ORGANISM: Artificial sequence
<220> FEATURE:
<223> OTHER INFORMATION: sequence is synthesized

<400> SEQUENCE: 89

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Asp Ser
             20                  25                  30

Trp Ile His Trp Val Arg Gln Ala Pro Gly Lys Gly Leu Glu Trp Val
         35                  40                  45

Ala Trp Ile Ser Pro Tyr Gly Gly Ser Thr Tyr Tyr Ala Asp Ser Val
     50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Arg His Trp Pro Gly Gly Phe Asp Tyr Trp Gly Gln Gly Thr
            100                 105                 110

Leu Val Thr Val Ser Ala
```

<210> SEQ ID NO 90
<211> LENGTH: 118
<212> TYPE: PRT
<213> ORGANISM: Artificial sequence
<220> FEATURE:
<223> OTHER INFORMATION: sequence is synthesized

<400> SEQUENCE: 90

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ala
        115

<210> SEQ ID NO 91
<211> LENGTH: 118
<212> TYPE: PRT
<213> ORGANISM: Artificial sequence
<220> FEATURE:
<223> OTHER INFORMATION: sequence is synthesized

<400> SEQUENCE: 91

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Gly Ser
            20                  25                  30

Trp Ile His Trp Val Arg Gln Ala Pro Gly Lys Gly Leu Glu Trp Val
        35                  40                  45

Ala Trp Ile Leu Pro Tyr Gly Gly Ser Ser Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ala
        115

<210> SEQ ID NO 92
<211> LENGTH: 108
<212> TYPE: PRT
<213> ORGANISM: Artificial sequence
<220> FEATURE:
<223> OTHER INFORMATION: sequence is synthesized

<400> SEQUENCE: 92

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg
            100                 105

<210> SEQ ID NO 93
<211> LENGTH: 108
<212> TYPE: PRT
<213> ORGANISM: Artificial sequence
<220> FEATURE:
<223> OTHER INFORMATION: sequence is synthesized

<400> SEQUENCE: 93

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Asn Val Pro Trp
                85                  90                  95

Thr Phe Gly Gln Gly Thr Lys Val Glu Ile Lys Arg
            100                 105

<210> SEQ ID NO 94
<211> LENGTH: 108
<212> TYPE: PRT
<213> ORGANISM: Artificial sequence
<220> FEATURE:
<223> OTHER INFORMATION: sequence is synthesized

<400> SEQUENCE: 94

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ala Pro Pro Trp

```
                    85                  90                  95

Thr Phe Gly Gln Gly Thr Lys Val Glu Ile Lys Arg
                100                 105

<210> SEQ ID NO 95
<211> LENGTH: 108
<212> TYPE: PRT
<213> ORGANISM: Artificial sequence
<220> FEATURE:
<223> OTHER INFORMATION: sequence is synthesized

<400> SEQUENCE: 95

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Thr Val Pro Trp
                85                  90                  95

Thr Phe Gly Gln Gly Thr Lys Val Glu Ile Lys Arg
                100                 105

<210> SEQ ID NO 96
<211> LENGTH: 108
<212> TYPE: PRT
<213> ORGANISM: Artificial sequence
<220> FEATURE:
<223> OTHER INFORMATION: sequence is synthesized

<400> SEQUENCE: 96

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Val Ile Asn Thr Phe
            20                  25                  30

Leu Ala Trp Tyr Gln Gln Lys Pro Gly Lys Ala Pro Lys Leu Leu Ile
        35                  40                  45

Tyr Ser Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Thr Val Pro Arg
                85                  90                  95

Thr Phe Gly Gln Gly Thr Lys Val Glu Ile Lys Arg
                100                 105

<210> SEQ ID NO 97
<211> LENGTH: 108
<212> TYPE: PRT
<213> ORGANISM: Artificial sequence
<220> FEATURE:
<223> OTHER INFORMATION: sequence is synthesized

<400> SEQUENCE: 97

Asp Ile Gln Met Thr Gln Ser Pro Ser Ser Leu Ser Ala Ser Val Gly
1               5                   10                  15
```

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Gly Val Pro Arg
                85                  90                  95

Thr Phe Gly Gln Gly Thr Lys Val Glu Ile Lys Arg
            100                 105

<210> SEQ ID NO 98
<211> LENGTH: 108
<212> TYPE: PRT
<213> ORGANISM: Artificial sequence
<220> FEATURE:
<223> OTHER INFORMATION: sequence is synthesized

<400> SEQUENCE: 98

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Phe Thr Pro Pro
                85                  90                  95

Thr Phe Gly Gln Gly Thr Lys Val Glu Ile Lys Arg
            100                 105

<210> SEQ ID NO 99
<211> LENGTH: 108
<212> TYPE: PRT
<213> ORGANISM: Artificial sequence
<220> FEATURE:
<223> OTHER INFORMATION: sequence is synthesized

<400> SEQUENCE: 99

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Phe Ile Thr Pro Thr
                85                  90                  95

Thr Phe Gly Gln Gly Thr Lys Val Glu Ile Lys Arg

-continued

<210> SEQ ID NO 100
<211> LENGTH: 108
<212> TYPE: PRT
<213> ORGANISM: Artificial sequence
<220> FEATURE:
<223> OTHER INFORMATION: sequence is synthesized

<400> SEQUENCE: 100

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Tyr Thr Pro Pro
                85                  90                  95

Thr Phe Gly Gln Gly Thr Lys Val Glu Ile Lys Arg
            100                 105

<210> SEQ ID NO 101
<211> LENGTH: 108
<212> TYPE: PRT
<213> ORGANISM: Artificial sequence
<220> FEATURE:
<223> OTHER INFORMATION: sequence is synthesized

<400> SEQUENCE: 101

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Phe Tyr Thr Pro Pro
                85                  90                  95

Thr Phe Gly Gln Gly Thr Lys Val Glu Ile Lys Arg
            100                 105

<210> SEQ ID NO 102
<211> LENGTH: 108
<212> TYPE: PRT
<213> ORGANISM: Artificial sequence
<220> FEATURE:
<223> OTHER INFORMATION: sequence is synthesized

<400> SEQUENCE: 102

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Leu Phe Thr Pro Pro
                85                  90                  95

Thr Phe Gly Gln Gly Thr Lys Val Glu Ile Lys Arg
                100                 105

<210> SEQ ID NO 103
<211> LENGTH: 108
<212> TYPE: PRT
<213> ORGANISM: Artificial sequence
<220> FEATURE:
<223> OTHER INFORMATION: sequence is synthesized

<400> SEQUENCE: 103

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Leu Tyr Thr Pro Pro
                85                  90                  95

Thr Phe Gly Gln Gly Thr Lys Val Glu Ile Lys Arg
                100                 105

<210> SEQ ID NO 104
<211> LENGTH: 108
<212> TYPE: PRT
<213> ORGANISM: Artificial sequence
<220> FEATURE:
<223> OTHER INFORMATION: sequence is synthesized

<400> SEQUENCE: 104

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Trp Tyr His Pro Pro
                85                  90                  95

Thr Phe Gly Gln Gly Thr Lys Val Glu Ile Lys Arg
                100                 105

```
<210> SEQ ID NO 105
<211> LENGTH: 108
<212> TYPE: PRT
<213> ORGANISM: Artificial sequence
<220> FEATURE:
<223> OTHER INFORMATION: sequence is synthesized

<400> SEQUENCE: 105

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Phe Tyr Ile Pro Pro
                85                  90                  95

Thr Phe Gly Gln Gly Thr Lys Val Glu Ile Lys Arg
            100                 105

<210> SEQ ID NO 106
<211> LENGTH: 108
<212> TYPE: PRT
<213> ORGANISM: Artificial sequence
<220> FEATURE:
<223> OTHER INFORMATION: sequence is synthesized

<400> SEQUENCE: 106

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Trp Tyr Thr Pro Thr
                85                  90                  95

Thr Phe Gly Gln Gly Thr Lys Val Glu Ile Lys Arg
            100                 105

<210> SEQ ID NO 107
<211> LENGTH: 108
<212> TYPE: PRT
<213> ORGANISM: Artificial sequence
<220> FEATURE:
<223> OTHER INFORMATION: sequence is synthesized

<400> SEQUENCE: 107

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45
```

```
Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65              70                  75                      80

Glu Asp Phe Ala Thr Tyr Tyr Cys Gln Gln Ser Tyr Phe Ile Pro Pro
                85              90                  95

Thr Phe Gly Gln Gly Thr Lys Val Glu Ile Lys Arg
            100             105
```